US011053486B2

(12) United States Patent
O'Connell et al.

(10) Patent No.: US 11,053,486 B2
(45) Date of Patent: *Jul. 6, 2021

(54) DETERGENT COMPOSITIONS COMPRISING POLYPEPTIDES HAVING XANTHAN DEGRADING ACTIVITY

(71) Applicant: Henkel AG & Co. KGaA, Duesseldorf (DE)

(72) Inventors: Timothy O'Connell, Landsberg am Lech (DE); Susanne Tondera, Duesseldorf (DE); Nina Mussmann, Willich (DE); Daniela Herbst, Duesseldorf (DE); Dorotea R. S. Raventos, Denmark (DK); Lars Anderson, Malmoe (SE); Lorena Palmén, Malmoe (SE); Liv Christiansen, Gentofte (DK); Peter Hallin, Alleroed (DK); Leigh Murphy, Roskilde (DK); Mette Louise Dissing Overgaard, Copenhagen S (DK); Rune Nygaard Monrad, Hilleroed (DK)

(73) Assignee: Henkel AG & Co. KGaA, Duesseldorf (DE)

( * ) Notice: Subject to any disclaimer, the term of this patent is extended or adjusted under 35 U.S.C. 154(b) by 73 days.

This patent is subject to a terminal disclaimer.

(21) Appl. No.: 15/760,425

(22) PCT Filed: Sep. 15, 2016

(86) PCT No.: PCT/EP2016/071801
§ 371 (c)(1),
(2) Date: Mar. 15, 2018

(87) PCT Pub. No.: WO2017/046232
PCT Pub. Date: Mar. 23, 2017

(65) Prior Publication Data
US 2018/0273881 A1    Sep. 27, 2018

(30) Foreign Application Priority Data

Sep. 17, 2015  (EP) .................................... 15185640

(51) Int. Cl.
| | |
|---|---|
| *C12N 9/26* | (2006.01) |
| *C07H 21/04* | (2006.01) |
| *C12N 15/00* | (2006.01) |
| *C11D 3/386* | (2006.01) |
| *C12N 9/24* | (2006.01) |
| *C12N 15/52* | (2006.01) |
| *C12N 15/09* | (2006.01) |

(52) U.S. Cl.
CPC ........ *C12N 9/2402* (2013.01); *C11D 3/38636* (2013.01); *C11D 3/38681* (2013.01); *C12N 15/00* (2013.01); *C12N 15/09* (2013.01); *C12N 15/52* (2013.01)

(58) Field of Classification Search
CPC .................................................... C12N 9/2402
See application file for complete search history.

(56) References Cited

U.S. PATENT DOCUMENTS

| | | | |
|---|---|---|---|
| 9,752,102 B2 | 9/2017 | Mussmann et al. | |
| 2013/0025073 A1* | 1/2013 | Souter .................... | C11D 3/166 8/137 |

FOREIGN PATENT DOCUMENTS

| | | |
|---|---|---|
| CN | 103987845 A | 8/2014 |
| WO | 2011077463 A1 | 6/2011 |
| WO | 2013167581 A1 | 11/2013 |
| WO | 2015001017 A2 | 1/2015 |

OTHER PUBLICATIONS

Studer. Residue mutations and their impact on protein structure and function: detecting beneficial and pathogenic changes. Biochem. J. (2013) 449, 581-594.*
Pena. M2V1S3. UniProtKB Database. 2013.*
EPO, International Search Report and Written Opinion issued in International Application No. PCT/EP2016/071801, dated Aug. 12, 2016.
Nankai Hirokazu et al., "Microbial system for polysaccharide depolymerization: Enzymatic route for xanthan depolymerization by *Bacillus* sp. strain GL1", Applied and Environmental Microbiology, American Society for Microbiology, US dated Jun. 1, 1999, vol. 65, No. 6.
Amino Acid Sequence related to XP002764509, dated May 1, 2013.
Henrik Aspeborg et al., "Evolution, substrate specificity and subfamily classification of glycoside hydrolase family 5 (GH5)", BMC Evolutionary Biology, dated Sep. 20, 2012, vol. 12, No. 1.
Bing Li et al., "Endoxanthanase, a Novel [beta]-d-Glucanase Hydrolyzing Backbone Linkage of Intact Xanthan from Newly Isolated *Microbacterium* sp. XT11", Applied Biochemistry and Biotechnology, dated Dec. 3, 2008, vol. 159, No. 1.

* cited by examiner

*Primary Examiner* — Yong D Pak
(74) *Attorney, Agent, or Firm* — Lorenz & Kopf, LLP

(57) ABSTRACT

The present disclosure relates to detergent compositions comprising polypeptides having xanthan degrading activity. The disclosure also relates to methods for producing said detergent compositions and to the use of said detergent compositions in cleaning applications.

18 Claims, No Drawings
Specification includes a Sequence Listing.

SEQUENCE LISTING

```
<160> NUMBER OF SEQ ID NOS: 25

<210> SEQ ID NO 1
<211> LENGTH: 2517
<212> TYPE: DNA
<213> ORGANISM: Opitutaceae sp
<220> FEATURE:
<221> NAME/KEY: CDS
<222> LOCATION: (1)..(2514)
<220> FEATURE:
<221> NAME/KEY: sig_peptide
<222> LOCATION: (1)..(108)
<220> FEATURE:
<221> NAME/KEY: mat_peptide
<222> LOCATION: (109)..(2514)

<400> SEQUENCE: 1
```

```
atg caa tca tca agc tca aat tcg gtc gta tcc gct tcc cgg ata ctc      48
Met Gln Ser Ser Ser Ser Asn Ser Val Val Ser Ala Ser Arg Ile Leu
    -35             -30             -25 cga cgc ttc tcc ctc ccg ctg ctc gcc gcc gcg ctg ggc ctc gcc gcg      96
Arg Arg Phe Ser Leu Pro Leu Leu Ala Ala Ala Leu Gly Leu Ala Ala
-20             -15             -10              -5 ccc gcc cgc gcc gcc gac tat tac ctg aag gcc agc caa ggc gca tcc     144
Pro Ala Arg Ala Ala Asp Tyr Tyr Leu Lys Ala Ser Gln Gly Ala Ser
        -1   1              5                  10 aac cac tgg tcc tcc cat ctc acc gac tgg acc gcc aac gcc gac ggc     192
Asn His Trp Ser Ser His Leu Thr Asp Trp Thr Ala Asn Ala Asp Gly
        15                  20                  25 acc ggc gcc aac ccg acg gtc atc ggc ctg gcc gac acc ttc gac acc     240
Thr Gly Ala Asn Pro Thr Val Ile Gly Leu Ala Asp Thr Phe Asp Thr
    30                  35                  40 aac aac cgc acg ctt cgc act ccc gcc gtc aac gcc acc acc acc tac     288
Asn Asn Arg Thr Leu Arg Thr Pro Ala Val Asn Ala Thr Thr Thr Tyr
45                  50                  55                  60 ccg ggc ggc gtg ctc cgc ctt tcc ggc ggc gcc ggc gtc atc ggc atg     336
Pro Gly Gly Val Leu Arg Leu Ser Gly Gly Ala Gly Val Ile Gly Met
                65                  70                  75 aag act ggc ggc acc gcc gtc gcc atc gtg ccc aag ctc gtc tcc acc     384
Lys Thr Gly Gly Thr Ala Val Ala Ile Val Pro Lys Leu Val Ser Thr
            80                  85                  90 gcc ggc acc gtg gac gcc tgg cac acc ggc acc caa tac ttc cgc gcc     432
Ala Gly Thr Val Asp Ala Trp His Thr Gly Thr Gln Tyr Phe Arg Ala
        95                 100                 105 gac gac tgg gag aac ctc gcc tcc ggc acc ggg ttc acc gcg ctc aag     480
Asp Asp Trp Glu Asn Leu Ala Ser Gly Thr Gly Phe Thr Ala Leu Lys
    110                 115                 120 gcc gtc gcc ggc cgc acg ctc aag gtc agc gtc ggc aag ctc acc ggc     528
Ala Val Ala Gly Arg Thr Leu Lys Val Ser Val Gly Lys Leu Thr Gly
125                 130                 135                 140 tcc ggc gag acc cgt ctt cac ggc ggc ggc gcc gtc cgc ctc gac gtc     576
Ser Gly Glu Thr Arg Leu His Gly Gly Gly Ala Val Arg Leu Asp Val
                145                 150                 155 acc gac ggc gaa cgc tac ctc ggc gtc gtc cgc gtc tcc tcc ggc gcg     624
Thr Asp Gly Glu Arg Tyr Leu Gly Val Val Arg Val Ser Ser Gly Ala
            160                 165                 170 gcc gac ttc gac aac aac gtg ttc gtc tcc ggc ccg ctc gtg atc gag     672
Ala Asp Phe Asp Asn Asn Val Phe Val Ser Gly Pro Leu Val Ile Glu
        175                 180                 185 acc ggc gcg acc gtc gtg ctc gac cag gcc gtc tcc ttc gcc ggc ctg     720
Thr Gly Ala Thr Val Val Leu Asp Gln Ala Val Ser Phe Ala Gly Leu
    190                 195                 200 acc gtc gcc ggc acc gag tat tcg ccc ggc aac tac acc ttc gcc gcg     768
Thr Val Ala Gly Thr Glu Tyr Ser Pro Gly Asn Tyr Thr Phe Ala Ala
205                 210                 215                 220 ctc cag gcc gcg cat cct acg gtg ttc acc tcc ggc acc gcc ggc ggc     816
Leu Gln Ala Ala His Pro Thr Val Phe Thr Ser Gly Thr Ala Gly Gly
                225                 230                 235 tcg atc acc gtc cgc gcc ccg cgc acc tgg tat ctc acc gtg aat cag     864
Ser Ile Thr Val Arg Ala Pro Arg Thr Trp Tyr Leu Thr Val Asn Gln
            240                 245                 250 ggc ggc gtg cag aac tgg acc gag acc tac ctt tcg aac tgg aac tcc     912
Gly Gly Val Gln Asn Trp Thr Glu Thr Tyr Leu Ser Asn Trp Asn Ser
        255                 260                 265 gcc gcc aat ggc tcc ggc gtc gcg ccg act tcg atc aac ggc tac gac     960
Ala Ala Asn Gly Ser Gly Val Ala Pro Thr Ser Ile Asn Gly Tyr Asp
```

```
                     270                 275                 280
ttc tac atc gat cag gtc tcc aac cgc gag atc cgc acg ccc tcc acc      1008
Phe Tyr Ile Asp Gln Val Ser Asn Arg Glu Ile Arg Thr Pro Ser Thr
285                 290                 295                 300 gcc tcc acc ttc ggc ggc ggc gcg ctc gcc ctc gcc agc ggc gcc aag      1056
Ala Ser Thr Phe Gly Gly Gly Ala Leu Ala Leu Ala Ser Gly Ala Lys
                305                 310                 315 ctc acc ctc aag agt tcg ccc ggc gtc gtc agc acc atc ccg gcg ttc      1104
Leu Thr Leu Lys Ser Ser Pro Gly Val Val Ser Thr Ile Pro Ala Phe
            320                 325                 330 gtg aac acg aac tcc ccg atc atc gtg aac ggc ggc ggt agc ttc cgc      1152
Val Asn Thr Asn Ser Pro Ile Ile Val Asn Gly Gly Gly Ser Phe Arg
        335                 340                 345 caa agt ctc gcc ctc ggt gac tgg gag atc gcc tcc ggc atc acc aag      1200
Gln Ser Leu Ala Leu Gly Asp Trp Glu Ile Ala Ser Gly Ile Thr Lys
    350                 355                 360 ctc tcc gcc ggc tcc ggt cgc agc ctc ggc ttc gac atc gac tac ctc      1248
Leu Ser Ala Gly Ser Gly Arg Ser Leu Gly Phe Asp Ile Asp Tyr Leu
365                 370                 375                 380 ggc ggc gcg ggt ggc ctt gtc acc caa aac ggc ggc tct tac ttc ctc      1296
Gly Gly Ala Gly Gly Leu Val Thr Gln Asn Gly Gly Ser Tyr Phe Leu
                385                 390                 395 agc ctc gac gac ggc tcc ggc tac acc ggc acg ctc aac cac gcg tcc      1344
Ser Leu Asp Asp Gly Ser Gly Tyr Thr Gly Thr Leu Asn His Ala Ser
            400                 405                 410 ggc gcg ctc cgc ttc gag tcc gtc ttc tcc acc gag ggc gcg ctc acc      1392
Gly Ala Leu Arg Phe Glu Ser Val Phe Ser Thr Glu Gly Ala Leu Thr
        415                 420                 425 atc ggc tcc tcg gcg acc gtc cac ctc gac caa cag gtt tac gtc acg      1440
Ile Gly Ser Ser Ala Thr Val His Leu Asp Gln Gln Val Tyr Val Thr
    430                 435                 440 tcg ttc tcc gtc gcc ggt gtc gcc aag gcc gcc ggc atc cac acc tac      1488
Ser Phe Ser Val Ala Gly Val Ala Lys Ala Ala Gly Ile His Thr Tyr
445                 450                 455                 460 gcc tcg ctg aac gcc gcg cat ccc gca cag ttc acc gcc ggc gcc gcg      1536
Ala Ser Leu Asn Ala Ala His Pro Ala Gln Phe Thr Ala Gly Ala Ala
                465                 470                 475 ccc gga ctc gtc gct gtt tac acg ccc gac acc gcc ggc ccc gtc cgc      1584
Pro Gly Leu Val Ala Val Tyr Thr Pro Asp Thr Ala Gly Pro Val Arg
            480                 485                 490 atg aac ggc gtc aat atc tcc ggc ccc gag agc aac acc gcc aac ctc      1632
Met Asn Gly Val Asn Ile Ser Gly Pro Glu Ser Asn Thr Ala Asn Leu
        495                 500                 505 ccc ggc acc tac ggc tac aac tac gtt tac ccc acc gag gcc gac ttc      1680
Pro Gly Thr Tyr Gly Tyr Asn Tyr Val Tyr Pro Thr Glu Ala Asp Phe
    510                 515                 520 gac tac tac gcc tcc aag ggc ctc aac ctc atc cgc att ccc ttc cgc      1728
Asp Tyr Tyr Ala Ser Lys Gly Leu Asn Leu Ile Arg Ile Pro Phe Arg
525                 530                 535                 540 tgg gag cgc atg cag cac ggc ctg aac gtt ccg ctc aac acc gcc cag      1776
Trp Glu Arg Met Gln His Gly Leu Asn Val Pro Leu Asn Thr Ala Gln
                545                 550                 555 ctc ggc tac atg gac acc gcc gtc gcc cgc gcc tcc gcg cgc ggc atg      1824
Leu Gly Tyr Met Asp Thr Ala Val Ala Arg Ala Ser Ala Arg Gly Met
            560                 565                 570 aag gtc atc ctc gat atg cac aac tac gcc cgc tgc aaa gtc ggc gga      1872
Lys Val Ile Leu Asp Met His Asn Tyr Ala Arg Cys Lys Val Gly Gly
        575                 580                 585 gtc acc tac aag ttc ggc gac gcg cag ctc ccc gcc tcg gcc tac gcc      1920
```

-continued

```
                Val Thr Tyr Lys Phe Gly Asp Ala Gln Leu Pro Ala Ser Ala Tyr Ala
                    590                 595                 600 gac gtc tgg cgc cgt ctc gcc gac cac tac aaa aac gag ccc gcc atc        1968
Asp Val Trp Arg Arg Leu Ala Asp His Tyr Lys Asn Glu Pro Ala Ile
605                 610                 615                 620 tac ggc ttc gac atc atg aac gag ccc aac ggc ctc tcc ggc ggc gtc        2016
Tyr Gly Phe Asp Ile Met Asn Glu Pro Asn Gly Leu Ser Gly Gly Val
                625                 630                 635 tgg ccc gcc tac gcc cag gcc gcg gtc aac gcc atc cgc gag gtc aat        2064
Trp Pro Ala Tyr Ala Gln Ala Ala Val Asn Ala Ile Arg Glu Val Asn
            640                 645                 650 ctg tcc acc tgg gtc atc gtc gag ggc gag ttt tgg gcc aac gct tgg        2112
Leu Ser Thr Trp Val Ile Val Glu Gly Glu Phe Trp Ala Asn Ala Trp
        655                 660                 665 ggc ttc gag acc aag aac ccg tat ctg cac aac gtc cgc gat ccc gtc        2160
Gly Phe Glu Thr Lys Asn Pro Tyr Leu His Asn Val Arg Asp Pro Val
    670                 675                 680 ggc cgc ctc atg ttc tcc gcc cac tcc tac tgg agc gac gcc ggc acc        2208
Gly Arg Leu Met Phe Ser Ala His Ser Tyr Trp Ser Asp Ala Gly Thr
685                 690                 695                 700 gat gtt tac aag acc tac gac gaa gag ggc gcc tat ccc gag atg ggc        2256
Asp Val Tyr Lys Thr Tyr Asp Glu Glu Gly Ala Tyr Pro Glu Met Gly
                705                 710                 715 gtg aac aac gtg aag ccc ttc atc gac tgg ctg aag aag cac gac gcc        2304
Val Asn Asn Val Lys Pro Phe Ile Asp Trp Leu Lys Lys His Asp Ala
            720                 725                 730 aag ggc ttc gtc ggc gaa tac ggc gtg ccc aac aac gac ccg cgc tgg        2352
Lys Gly Phe Val Gly Glu Tyr Gly Val Pro Asn Asn Asp Pro Arg Trp
        735                 740                 745 ctc gtc gtg ctg gac aac ttc ctc gcc tac ctc gcg gcc gag ggc gtg        2400
Leu Val Val Leu Asp Asn Phe Leu Ala Tyr Leu Ala Ala Glu Gly Val
    750                 755                 760 agc ggc acc tac tgg gcc ggc ggc gcc tgg tat tcg ggc agc ccg atc        2448
Ser Gly Thr Tyr Trp Ala Gly Gly Ala Trp Tyr Ser Gly Ser Pro Ile
765                 770                 775                 780 agc tgc cac ccg tcc tcc aac tac acc gtg gat cgc gcc gtc atg agc        2496
Ser Cys His Pro Ser Ser Asn Tyr Thr Val Asp Arg Ala Val Met Ser
                785                 790                 795 gtg ctc gaa gac cat cca tga                                            2517
Val Leu Glu Asp His Pro
            800
```

<210> SEQ ID NO 2
<211> LENGTH: 838
<212> TYPE: PRT
<213> ORGANISM: Opitutaceae sp

<400> SEQUENCE: 2

```
Met Gln Ser Ser Ser Asn Ser Val Val Ser Ala Ser Arg Ile Leu
    -35                 -30                 -25

Arg Arg Phe Ser Leu Pro Leu Leu Ala Ala Ala Leu Gly Leu Ala Ala
-20                 -15                 -10                  -5

Pro Ala Arg Ala Ala Asp Tyr Tyr Leu Lys Ala Ser Gln Gly Ala Ser
            -1  1                   5                  10

Asn His Trp Ser Ser His Leu Thr Asp Trp Thr Ala Asn Ala Asp Gly
                15                  20                  25

Thr Gly Ala Asn Pro Thr Val Ile Gly Leu Ala Asp Thr Phe Asp Thr
        30                  35                  40

Asn Asn Arg Thr Leu Arg Thr Pro Ala Val Asn Ala Thr Thr Thr Tyr
```

```
            45                  50                  55                  60
Pro Gly Gly Val Leu Arg Leu Ser Gly Gly Ala Gly Val Ile Gly Met
                     65                  70                  75
Lys Thr Gly Gly Thr Ala Val Ala Ile Val Pro Lys Leu Val Ser Thr
                 80                  85                  90
Ala Gly Thr Val Asp Ala Trp His Thr Gly Thr Gln Tyr Phe Arg Ala
             95                 100                 105
Asp Asp Trp Glu Asn Leu Ala Ser Gly Thr Gly Phe Thr Ala Leu Lys
        110                 115                 120
Ala Val Ala Gly Arg Thr Leu Lys Val Ser Val Gly Lys Leu Thr Gly
125                 130                 135                 140
Ser Gly Glu Thr Arg Leu His Gly Gly Ala Val Arg Leu Asp Val
                    145                 150                 155
Thr Asp Gly Glu Arg Tyr Leu Gly Val Val Arg Val Ser Ser Gly Ala
                160                 165                 170
Ala Asp Phe Asp Asn Asn Val Phe Val Ser Gly Pro Leu Val Ile Glu
            175                 180                 185
Thr Gly Ala Thr Val Val Leu Asp Gln Ala Val Ser Phe Ala Gly Leu
        190                 195                 200
Thr Val Ala Gly Thr Glu Tyr Ser Pro Gly Asn Tyr Thr Phe Ala Ala
205                 210                 215                 220
Leu Gln Ala Ala His Pro Thr Val Phe Thr Ser Gly Thr Ala Gly Gly
                    225                 230                 235
Ser Ile Thr Val Arg Ala Pro Arg Thr Trp Tyr Leu Thr Val Asn Gln
                240                 245                 250
Gly Gly Val Gln Asn Trp Thr Glu Thr Tyr Leu Ser Asn Trp Asn Ser
            255                 260                 265
Ala Ala Asn Gly Ser Gly Val Ala Pro Thr Ser Ile Asn Gly Tyr Asp
        270                 275                 280
Phe Tyr Ile Asp Gln Val Ser Asn Arg Glu Ile Arg Thr Pro Ser Thr
285                 290                 295                 300
Ala Ser Thr Phe Gly Gly Gly Ala Leu Ala Leu Ala Ser Gly Ala Lys
                    305                 310                 315
Leu Thr Leu Lys Ser Ser Pro Gly Val Ser Thr Ile Pro Ala Phe
                320                 325                 330
Val Asn Thr Asn Ser Pro Ile Ile Val Asn Gly Gly Ser Phe Arg
            335                 340                 345
Gln Ser Leu Ala Leu Gly Asp Trp Glu Ile Ala Ser Gly Ile Thr Lys
        350                 355                 360
Leu Ser Ala Gly Ser Gly Arg Ser Leu Gly Phe Asp Ile Asp Tyr Leu
365                 370                 375                 380
Gly Gly Ala Gly Gly Leu Val Thr Gln Asn Gly Ser Tyr Phe Leu
                    385                 390                 395
Ser Leu Asp Asp Gly Ser Gly Tyr Thr Gly Thr Leu Asn His Ala Ser
                400                 405                 410
Gly Ala Leu Arg Phe Glu Ser Val Phe Ser Thr Glu Gly Ala Leu Thr
            415                 420                 425
Ile Gly Ser Ser Ala Thr Val His Leu Asp Gln Val Tyr Val Thr
        430                 435                 440
Ser Phe Ser Val Ala Gly Val Ala Lys Ala Ala Gly Ile His Thr Tyr
445                 450                 455                 460
Ala Ser Leu Asn Ala Ala His Pro Ala Gln Phe Thr Ala Gly Ala Ala
                    465                 470                 475
```

Pro Gly Leu Val Ala Val Tyr Thr Pro Asp Thr Ala Gly Pro Val Arg
            480                 485                 490

Met Asn Gly Val Asn Ile Ser Gly Pro Glu Ser Asn Thr Ala Asn Leu
            495                 500                 505

Pro Gly Thr Tyr Gly Tyr Asn Tyr Val Tyr Pro Thr Glu Ala Asp Phe
510                 515                 520

Asp Tyr Tyr Ala Ser Lys Gly Leu Asn Leu Ile Arg Ile Pro Phe Arg
525                 530                 535                 540

Trp Glu Arg Met Gln His Gly Leu Asn Val Pro Leu Asn Thr Ala Gln
                545                 550                 555

Leu Gly Tyr Met Asp Thr Ala Val Ala Arg Ala Ser Ala Arg Gly Met
            560                 565                 570

Lys Val Ile Leu Asp Met His Asn Tyr Ala Arg Cys Lys Val Gly Gly
            575                 580                 585

Val Thr Tyr Lys Phe Gly Asp Ala Gln Leu Pro Ala Ser Ala Tyr Ala
    590                 595                 600

Asp Val Trp Arg Arg Leu Ala Asp His Tyr Lys Asn Glu Pro Ala Ile
605                 610                 615                 620

Tyr Gly Phe Asp Ile Met Asn Glu Pro Asn Gly Leu Ser Gly Gly Val
                625                 630                 635

Trp Pro Ala Tyr Ala Gln Ala Ala Val Asn Ala Ile Arg Glu Val Asn
            640                 645                 650

Leu Ser Thr Trp Val Ile Val Glu Gly Glu Phe Trp Ala Asn Ala Trp
            655                 660                 665

Gly Phe Glu Thr Lys Asn Pro Tyr Leu His Asn Val Arg Asp Pro Val
    670                 675                 680

Gly Arg Leu Met Phe Ser Ala His Ser Tyr Trp Ser Asp Ala Gly Thr
685                 690                 695                 700

Asp Val Tyr Lys Thr Tyr Asp Glu Glu Gly Ala Tyr Pro Glu Met Gly
                705                 710                 715

Val Asn Asn Val Lys Pro Phe Ile Asp Trp Leu Lys Lys His Asp Ala
            720                 725                 730

Lys Gly Phe Val Gly Glu Tyr Gly Val Pro Asn Asn Asp Pro Arg Trp
            735                 740                 745

Leu Val Val Leu Asp Asn Phe Leu Ala Tyr Leu Ala Ala Glu Gly Val
    750                 755                 760

Ser Gly Thr Tyr Trp Ala Gly Gly Ala Trp Tyr Ser Gly Ser Pro Ile
765                 770                 775                 780

Ser Cys His Pro Ser Ser Asn Tyr Thr Val Asp Arg Ala Val Met Ser
                785                 790                 795

Val Leu Glu Asp His Pro
            800

<210> SEQ ID NO 3
<211> LENGTH: 2496
<212> TYPE: DNA
<213> ORGANISM: Unknown
<220> FEATURE:
<223> OTHER INFORMATION: Environmental sample
<220> FEATURE:
<221> NAME/KEY: CDS
<222> LOCATION: (1)..(2493)
<220> FEATURE:
<221> NAME/KEY: sig_peptide
<222> LOCATION: (1)..(111)
<220> FEATURE:
<221> NAME/KEY: mat_peptide

<222> LOCATION: (112)..(2493)

<400> SEQUENCE: 3

| | | | | | | | | | | | | | | | | |
|---|---|---|---|---|---|---|---|---|---|---|---|---|---|---|---|---|
| atg | aac | acc | aca | cca | caa | ccc | acc | ccc | gcc | cgc | cgg | acg | cct | cga | cgc | 48 |
| Met | Asn | Thr | Thr | Pro | Gln | Pro | Thr | Pro | Ala | Arg | Arg | Thr | Pro | Arg | Arg | |
| | | -35 | | | | -30 | | | | | -25 | | | | | |
| ccg | ttc | ctc | gcc | acc | ctc | gct | acc | atc | ctc | ggc | ctc | gcc | gcc | tcc | gtc | 96 |
| Pro | Phe | Leu | Ala | Thr | Leu | Ala | Thr | Ile | Leu | Gly | Leu | Ala | Ala | Ser | Val | |
| | -20 | | | | | -15 | | | | | -10 | | | | | |
| tcc | tcc | gtc | tcc | gcc | gcc | gac | tgg | tat | ctc | gat | aaa | aac | cag | gcc | cgc | 144 |
| Ser | Ser | Val | Ser | Ala | Ala | Asp | Trp | Tyr | Leu | Asp | Lys | Asn | Gln | Ala | Arg | |
| -5 | | | | -1 | 1 | | | | 5 | | | | | 10 | | |
| tac | gcc | agc | tgg | gac | acc | ctc | gcc | gac | tgg | aaa | ccc | aac | ccc | gac | ggc | 192 |
| Tyr | Ala | Ser | Trp | Asp | Thr | Leu | Ala | Asp | Trp | Lys | Pro | Asn | Pro | Asp | Gly | |
| | | 15 | | | | | 20 | | | | | 25 | | | | |
| agc | ggc | tcc | aac | ccc | tcc | gcc | ctc | tcc | ccc | tcc | gac | acc | tac | cac | ctc | 240 |
| Ser | Gly | Ser | Asn | Pro | Ser | Ala | Leu | Ser | Pro | Ser | Asp | Thr | Tyr | His | Leu | |
| | | | 30 | | | | | 35 | | | | | 40 | | | |
| aac | ggc | ttc | atg | ctc | cgc | acc | ccc | gag | ggc | ggc | tcc | acc | tac | acc | ttc | 288 |
| Asn | Gly | Phe | Met | Leu | Arg | Thr | Pro | Glu | Gly | Gly | Ser | Thr | Tyr | Thr | Phe | |
| | 45 | | | | | 50 | | | | | 55 | | | | | |
| acc | ggc | ggc | ctc | ctc | agc | ctc | gcc | aac | aac | gcc | gac | aac | ttc | gcc | ctc | 336 |
| Thr | Gly | Gly | Leu | Leu | Ser | Leu | Ala | Asn | Asn | Ala | Asp | Asn | Phe | Ala | Leu | |
| 60 | | | | | 65 | | | | | 70 | | | | | 75 | |
| aag | acc | acc | ggc | tcc | ggc | gtc | tcc | atc | atc | ccc | gcc | ctg | cgc | acc | acc | 384 |
| Lys | Thr | Thr | Gly | Ser | Gly | Val | Ser | Ile | Ile | Pro | Ala | Leu | Arg | Thr | Thr | |
| | | | | 80 | | | | | 85 | | | | | 90 | | |
| gcc | ggc | ctc | gtc | caa | aac | gtc | ggc | tcc | ggc | acg | caa | aac | ctc | cag | gtt | 432 |
| Ala | Gly | Leu | Val | Gln | Asn | Val | Gly | Ser | Gly | Thr | Gln | Asn | Leu | Gln | Val | |
| | | | 95 | | | | | 100 | | | | | 105 | | | |
| ggc | cac | tac | caa | aac | ctc | tcc | ggc | acg | acc | tcc | tac | tac | gcc | cag | acc | 480 |
| Gly | His | Tyr | Gln | Asn | Leu | Ser | Gly | Thr | Thr | Ser | Tyr | Tyr | Ala | Gln | Thr | |
| | | 110 | | | | | 115 | | | | | 120 | | | | |
| ggg | cgc | ggc | ctc | aac | ctc | gcc | atc | acc | acc | ctc | gtg | ggc | tcc | ggc | cag | 528 |
| Gly | Arg | Gly | Leu | Asn | Leu | Ala | Ile | Thr | Thr | Leu | Val | Gly | Ser | Gly | Gln | |
| | 125 | | | | | 130 | | | | | 135 | | | | | |
| ttc | cgc | ttc | tac | ggc | ggc | ggc | acc | tac | tac | ctc | tcc | ctc | gcc | aac | tcc | 576 |
| Phe | Arg | Phe | Tyr | Gly | Gly | Gly | Thr | Tyr | Tyr | Leu | Ser | Leu | Ala | Asn | Ser | |
| 140 | | | | | 145 | | | | | 150 | | | | | 155 | |
| ccg | acc | tac | gac | ggc | gac | atc | tac | gtc | caa | tcc | ggc | acc | atc | gat | ttc | 624 |
| Pro | Thr | Tyr | Asp | Gly | Asp | Ile | Tyr | Val | Gln | Ser | Gly | Thr | Ile | Asp | Phe | |
| | | | | 160 | | | | | 165 | | | | | 170 | | |
| aac | aac | gac | ctc | gcc | acc | gcc | ggc | act | ctc | acc | gtc | aac | acc | ggt | gcc | 672 |
| Asn | Asn | Asp | Leu | Ala | Thr | Ala | Gly | Thr | Leu | Thr | Val | Asn | Thr | Gly | Ala | |
| | | | 175 | | | | | 180 | | | | | 185 | | | |
| aag | gtc | gcc | ctc | gac | cag | gcc | gtc | acc | ttc | acc | ggc | ctc | acc | ata | gcc | 720 |
| Lys | Val | Ala | Leu | Asp | Gln | Ala | Val | Thr | Phe | Thr | Gly | Leu | Thr | Ile | Ala | |
| | | 190 | | | | | 195 | | | | | 200 | | | | |
| ggc | aca | gcg | tat | cca | gtt | gga | aac | tac | agc | tac | gcc | gcg | ctt | cag | gcc | 768 |
| Gly | Thr | Ala | Tyr | Pro | Val | Gly | Asn | Tyr | Ser | Tyr | Ala | Ala | Leu | Gln | Ala | |
| | 205 | | | | | 210 | | | | | 215 | | | | | |
| gcc | cac | ccc | gcc | gtt | ttc | gtc | tcc | ggc | acc | tcc | ggc | gga | gcc | atc | aac | 816 |
| Ala | His | Pro | Ala | Val | Phe | Val | Ser | Gly | Thr | Ser | Gly | Gly | Ala | Ile | Asn | |
| 220 | | | | | 225 | | | | | 230 | | | | | 235 | |
| gtc | cgc | gcc | ccg | cgc | aac | tgg | tat | ctc | tcc | acc | cac | caa | ccc | gtc | ggc | 864 |
| Val | Arg | Ala | Pro | Arg | Asn | Trp | Tyr | Leu | Ser | Thr | His | Gln | Pro | Val | Gly | |
| | | | | 240 | | | | | 245 | | | | | 250 | | |
| gcc | agc | tgg | aac | acc | ctc | gcc | cat | tgg | cgc | gcc | aac | ccc | gac | ggc | acc | 912 |
| Ala | Ser | Trp | Asn | Thr | Leu | Ala | His | Trp | Arg | Ala | Asn | Pro | Asp | Gly | Thr | |
| | | | 255 | | | | | 260 | | | | | 265 | | | |

```
ggc gcc acc gcc gac tcc atc aac tcc ttc gac aac tac atc aac caa      960
Gly Ala Thr Ala Asp Ser Ile Asn Ser Phe Asp Asn Tyr Ile Asn Gln
            270                 275                 280 gtc tcc ggc cgc acc ctg cgc acc ccc gaa acc acc gcc acc ttc gcc     1008
Val Ser Gly Arg Thr Leu Arg Thr Pro Glu Thr Thr Ala Thr Phe Ala
285                 290                 295 ggc ggt tcc ctc gtc ctc gcc gac ggc ggc aac ctc tcg ctc aag gcc     1056
Gly Gly Ser Leu Val Leu Ala Asp Gly Gly Asn Leu Ser Leu Lys Ala
300                 305                 310                 315 ccc gcc ggc cac tcc agc acc atc ccc gcc ttc gcc aca tcg gga tcg     1104
Pro Ala Gly His Ser Ser Thr Ile Pro Ala Phe Ala Thr Ser Gly Ser
                320                 325                 330 att tcc atc acc aac ggc ttc agc agc atc acc cag ccc ctc gtc atc     1152
Ile Ser Ile Thr Asn Gly Phe Ser Ser Ile Thr Gln Pro Leu Val Ile
            335                 340                 345 ggc gac tgg cac ctc ggc gcc ggc acc gcc caa gtc tcc gtg cca agc     1200
Gly Asp Trp His Leu Gly Ala Gly Thr Ala Gln Val Ser Val Pro Ser
        350                 355                 360 acc agc acc gtg cag ctc acc gtc gat aaa ctc tcc ggc gac ggc acc     1248
Thr Ser Thr Val Gln Leu Thr Val Asp Lys Leu Ser Gly Asp Gly Thr
365                 370                 375 ctc cag ttc cag aac ggc ggc aaa tac acc ctc aac atc cgc ggc gcg     1296
Leu Gln Phe Gln Asn Gly Gly Lys Tyr Thr Leu Asn Ile Arg Gly Ala
380                 385                 390                 395 tcc gcc ttc acc ggc acc ctc cgc cac ctc tcc ggc acg ctc acc gta     1344
Ser Ala Phe Thr Gly Thr Leu Arg His Leu Ser Gly Thr Leu Thr Val
                400                 405                 410 gcc tcc cag atc ggc acc ggc ggc acc ctc gtc gtc gaa tcc acc ggc     1392
Ala Ser Gln Ile Gly Thr Gly Gly Thr Leu Val Val Glu Ser Thr Gly
            415                 420                 425 gcg gtg aaa ctc gac cac ccc ggc ttc ttc acc ggc gtc acc gtc gcc     1440
Ala Val Lys Leu Asp His Pro Gly Phe Phe Thr Gly Val Thr Val Ala
        430                 435                 440 ggc acg ccc ctc gcc ccc ggc tac cac acc tac gcc gcg ctc aaa gcc     1488
Gly Thr Pro Leu Ala Pro Gly Tyr His Thr Tyr Ala Ala Leu Lys Ala
445                 450                 455 gcc cac ccc gcg cgc ttc ccc acc ggc tcc acc aac gcc ttc ctc gcc     1536
Ala His Pro Ala Arg Phe Pro Thr Gly Ser Thr Asn Ala Phe Leu Ala
460                 465                 470                 475 gtc tat ccg ccc gac acc acc ggc ccc gcc cac atg ttc ggc gtc aac     1584
Val Tyr Pro Pro Asp Thr Thr Gly Pro Ala His Met Phe Gly Val Asn
                480                 485                 490 ctc gcc ggc ggc gaa ttc ggc acc ccg atg ccc ggc gtt tac ggc acc     1632
Leu Ala Gly Gly Glu Phe Gly Thr Pro Met Pro Gly Val Tyr Gly Thr
            495                 500                 505 gac tac atc tac ccg agc gcc gcc gcc ttc gat tac tac cac ggc aaa     1680
Asp Tyr Ile Tyr Pro Ser Ala Ala Ala Phe Asp Tyr Tyr His Gly Lys
        510                 515                 520 ggc ctc aaa ctc atc cgc ctc ccc ttt aag tgg gaa cgc ctc cag cac     1728
Gly Leu Lys Leu Ile Arg Leu Pro Phe Lys Trp Glu Arg Leu Gln His
525                 530                 535 acc ctc aac gcc ccc ctc aac gcc gcc gag ctc gcc cgc atc gac acc     1776
Thr Leu Asn Ala Pro Leu Asn Ala Ala Glu Leu Ala Arg Ile Asp Thr
540                 545                 550                 555 gtc gtc ggc tac gcc tcc gcg cgc ggc atg aag gtc gtc ctc gac atg     1824
Val Val Gly Tyr Ala Ser Ala Arg Gly Met Lys Val Val Leu Asp Met
                560                 565                 570 cac aac tac gcc cgc cgc aaa gaa agc ggc acc acc tac ctc atc ggc     1872
His Asn Tyr Ala Arg Arg Lys Glu Ser Gly Thr Thr Tyr Leu Ile Gly
```

```
                575                 580                 585
acc ggc ccc gtc acc atg gac gcc ttc ggc gac gtc tgg cgt cgc atc      1920
Thr Gly Pro Val Thr Met Asp Ala Phe Gly Asp Val Trp Arg Arg Ile
        590                 595                 600 gcc gat cac tac aag ggc aac ccc gcc atc tac ggc tac ggc atc atg      1968
Ala Asp His Tyr Lys Gly Asn Pro Ala Ile Tyr Gly Tyr Gly Ile Met
605                 610                 615 aac gag ccc tac tcc acc aac acc acc tgg ccc cag atg gcc cag acc      2016
Asn Glu Pro Tyr Ser Thr Asn Thr Thr Trp Pro Gln Met Ala Gln Thr
620                 625                 630                 635 gcc gtc aac gcc atc cgc acc gtt gac ctc acc acc cac gtc atc gtc      2064
Ala Val Asn Ala Ile Arg Thr Val Asp Leu Thr Thr His Val Ile Val
            640                 645                 650 gcc ggc gac ggc tgg tcc aac gcc acc ggc tgg cgc tcc aag aac ccc      2112
Ala Gly Asp Gly Trp Ser Asn Ala Thr Gly Trp Arg Ser Lys Asn Pro
            655                 660                 665 aac ctc gac acc cag gac ccc gtc ggc cgc ctc atc tac gaa gcc cac      2160
Asn Leu Asp Thr Gln Asp Pro Val Gly Arg Leu Ile Tyr Glu Ala His
            670                 675                 680 tgc tac ttc gat tcc aac ctc tcc ggc acc tac acc caa agc tac gat      2208
Cys Tyr Phe Asp Ser Asn Leu Ser Gly Thr Tyr Thr Gln Ser Tyr Asp
685                 690                 695 gcc gcc ggc gcc cac ccc atg atc ggc gtg gac cgt gtg cgc gaa ttc      2256
Ala Ala Gly Ala His Pro Met Ile Gly Val Asp Arg Val Arg Glu Phe
700                 705                 710                 715 gtc gag tgg ctt cag gaa acc ggc aac aaa ggc ttc atc ggc gaa tac      2304
Val Glu Trp Leu Gln Glu Thr Gly Asn Lys Gly Phe Ile Gly Glu Tyr
            720                 725                 730 ggc gtc ccc ggc aac gac ccc cgc tgg ctc gtc gtg ctc gac aac ttc      2352
Gly Val Pro Gly Asn Asp Pro Arg Trp Leu Val Val Leu Asp Asn Phe
            735                 740                 745 ctc gcc tac ctc gac gcc aac ggc gtc tcc ggc acc tac tgg gcc ggc      2400
Leu Ala Tyr Leu Asp Ala Asn Gly Val Ser Gly Thr Tyr Trp Ala Gly
            750                 755                 760 ggt cct tgg tgg ggc aac tac ccg ctc agc tgc gaa ccc acc tcc aac      2448
Gly Pro Trp Trp Gly Asn Tyr Pro Leu Ser Cys Glu Pro Thr Ser Asn
765                 770                 775 tac acc gtg gac aaa ccc cag atg agc gtc ctc gaa aac tac aac tga      2496
Tyr Thr Val Asp Lys Pro Gln Met Ser Val Leu Glu Asn Tyr Asn
780                 785                 790

<210> SEQ ID NO 4
<211> LENGTH: 831
<212> TYPE: PRT
<213> ORGANISM: Unknown
<220> FEATURE:
<223> OTHER INFORMATION: Synthetic Construct

<400> SEQUENCE: 4

Met Asn Thr Thr Pro Gln Pro Thr Pro Ala Arg Arg Thr Pro Arg Arg
            -35                 -30                 -25

Pro Phe Leu Ala Thr Leu Ala Thr Ile Leu Gly Leu Ala Ala Ser Val
        -20                 -15                 -10

Ser Ser Val Ser Ala Ala Asp Trp Tyr Leu Asp Lys Asn Gln Ala Arg
-5              -1  1               5                   10

Tyr Ala Ser Trp Asp Thr Leu Ala Asp Trp Lys Pro Asn Pro Asp Gly
                15                  20                  25

Ser Gly Ser Asn Pro Ser Ala Leu Ser Pro Ser Asp Thr Tyr His Leu
            30                  35                  40
```

```
Asn Gly Phe Met Leu Arg Thr Pro Glu Gly Gly Ser Thr Tyr Thr Phe
    45                  50                  55

Thr Gly Leu Leu Ser Leu Ala Asn Asn Ala Asp Asn Phe Ala Leu
60                  65                  70                  75

Lys Thr Thr Gly Ser Gly Val Ser Ile Ile Pro Ala Leu Arg Thr Thr
                80                  85                  90

Ala Gly Leu Val Gln Asn Val Gly Ser Gly Thr Gln Asn Leu Gln Val
                95                  100                 105

Gly His Tyr Gln Asn Leu Ser Gly Thr Thr Ser Tyr Tyr Ala Gln Thr
            110                 115                 120

Gly Arg Gly Leu Asn Leu Ala Ile Thr Thr Leu Val Gly Ser Gly Gln
            125                 130                 135

Phe Arg Phe Tyr Gly Gly Thr Tyr Tyr Leu Ser Leu Ala Asn Ser
140                 145                 150                 155

Pro Thr Tyr Asp Gly Asp Ile Tyr Val Gln Ser Gly Thr Ile Asp Phe
                160                 165                 170

Asn Asn Asp Leu Ala Thr Ala Gly Thr Leu Thr Val Asn Thr Gly Ala
                175                 180                 185

Lys Val Ala Leu Asp Gln Ala Val Thr Phe Thr Gly Leu Thr Ile Ala
        190                 195                 200

Gly Thr Ala Tyr Pro Val Gly Asn Tyr Ser Tyr Ala Ala Leu Gln Ala
        205                 210                 215

Ala His Pro Ala Val Phe Val Ser Gly Thr Ser Gly Gly Ala Ile Asn
220                 225                 230                 235

Val Arg Ala Pro Arg Asn Trp Tyr Leu Ser Thr His Gln Pro Val Gly
                240                 245                 250

Ala Ser Trp Asn Thr Leu Ala His Trp Arg Ala Asn Pro Asp Gly Thr
                255                 260                 265

Gly Ala Thr Ala Asp Ser Ile Asn Ser Phe Asp Asn Tyr Ile Asn Gln
            270                 275                 280

Val Ser Gly Arg Thr Leu Arg Thr Pro Glu Thr Thr Ala Thr Phe Ala
    285                 290                 295

Gly Gly Ser Leu Val Leu Ala Asp Gly Gly Asn Leu Ser Leu Lys Ala
300                 305                 310                 315

Pro Ala Gly His Ser Ser Thr Ile Pro Ala Phe Ala Thr Ser Gly Ser
                320                 325                 330

Ile Ser Ile Thr Asn Gly Phe Ser Ser Ile Thr Gln Pro Leu Val Ile
            335                 340                 345

Gly Asp Trp His Leu Gly Ala Gly Thr Ala Gln Val Ser Val Pro Ser
            350                 355                 360

Thr Ser Thr Val Gln Leu Thr Val Asp Lys Leu Ser Gly Asp Gly Thr
    365                 370                 375

Leu Gln Phe Gln Asn Gly Gly Lys Tyr Thr Leu Asn Ile Arg Gly Ala
380                 385                 390                 395

Ser Ala Phe Thr Gly Thr Leu Arg His Leu Ser Gly Thr Leu Thr Val
                400                 405                 410

Ala Ser Gln Ile Gly Thr Gly Gly Thr Leu Val Val Glu Ser Thr Gly
            415                 420                 425

Ala Val Lys Leu Asp His Pro Gly Phe Phe Thr Gly Thr Val Ala
            430                 435                 440

Gly Thr Pro Leu Ala Pro Gly Tyr His Thr Tyr Ala Ala Leu Lys Ala
    445                 450                 455

Ala His Pro Ala Arg Phe Pro Thr Gly Ser Thr Asn Ala Phe Leu Ala
```

```
                460                 465                 470                 475
        Val Tyr Pro Pro Asp Thr Thr Gly Pro Ala His Met Phe Gly Val Asn
                            480                 485                 490

Leu Ala Gly Gly Glu Phe Gly Thr Pro Met Pro Gly Val Tyr Gly Thr
                        495                 500                 505

Asp Tyr Ile Tyr Pro Ser Ala Ala Phe Asp Tyr His Gly Lys
                    510                 515                 520

Gly Leu Lys Leu Ile Arg Leu Pro Phe Lys Trp Glu Arg Leu Gln His
                525                 530                 535

Thr Leu Asn Ala Pro Leu Asn Ala Ala Glu Leu Ala Arg Ile Asp Thr
        540                 545                 550                 555

Val Val Gly Tyr Ala Ser Ala Arg Gly Met Lys Val Leu Asp Met
                            560                 565                 570

His Asn Tyr Ala Arg Arg Lys Glu Ser Gly Thr Thr Tyr Leu Ile Gly
                        575                 580                 585

Thr Gly Pro Val Thr Met Asp Ala Phe Gly Asp Val Trp Arg Arg Ile
                    590                 595                 600

Ala Asp His Tyr Lys Gly Asn Pro Ala Ile Tyr Gly Tyr Gly Ile Met
                605                 610                 615

Asn Glu Pro Tyr Ser Thr Asn Thr Thr Trp Pro Gln Met Ala Gln Thr
        620                 625                 630                 635

Ala Val Asn Ala Ile Arg Thr Val Asp Leu Thr Thr His Val Ile Val
                            640                 645                 650

Ala Gly Asp Gly Trp Ser Asn Ala Thr Gly Trp Arg Ser Lys Asn Pro
                        655                 660                 665

Asn Leu Asp Thr Gln Asp Pro Val Gly Arg Leu Ile Tyr Glu Ala His
                    670                 675                 680

Cys Tyr Phe Asp Ser Asn Leu Ser Gly Thr Tyr Thr Gln Ser Tyr Asp
                685                 690                 695

Ala Ala Gly Ala His Pro Met Ile Gly Val Asp Arg Val Arg Glu Phe
        700                 705                 710                 715

Val Glu Trp Leu Gln Glu Thr Gly Asn Lys Gly Phe Ile Gly Glu Tyr
                            720                 725                 730

Gly Val Pro Gly Asn Asp Pro Arg Trp Leu Val Val Leu Asp Asn Phe
                        735                 740                 745

Leu Ala Tyr Leu Asp Ala Asn Gly Val Ser Gly Thr Tyr Trp Ala Gly
                    750                 755                 760

Gly Pro Trp Trp Gly Asn Tyr Pro Leu Ser Cys Glu Pro Thr Ser Asn
                765                 770                 775

Tyr Thr Val Asp Lys Pro Gln Met Ser Val Leu Glu Asn Tyr Asn
        780                 785                 790

<210> SEQ ID NO 5
<211> LENGTH: 2508
<212> TYPE: DNA
<213> ORGANISM: Unknown
<220> FEATURE:
<223> OTHER INFORMATION: Environmental sample
<220> FEATURE:
<221> NAME/KEY: CDS
<222> LOCATION: (1)..(2505)
<220> FEATURE:
<221> NAME/KEY: sig_peptide
<222> LOCATION: (1)..(105)
<220> FEATURE:
<221> NAME/KEY: mat_peptide
<222> LOCATION: (106)..(2505)
```

<400> SEQUENCE: 5

```
atg aaa cac cac cac acc aca cca cac acc ccg cgt cgg acc ctg ctc    48
Met Lys His His His Thr Thr Pro His Thr Pro Arg Arg Thr Leu Leu
-35                 -30                 -25                 -20 cgc tcg ctt gcc ggc ctg ctg gct ctc gcc acc ggc ctc gcc tcc acc    96
Arg Ser Leu Ala Gly Leu Leu Ala Leu Ala Thr Gly Leu Ala Ser Thr
            -15                 -10                  -5 gcc cac gcc gcc gac tac tac ctc aaa gtc aac caa ccc cac ccc aac   144
Ala His Ala Ala Asp Tyr Tyr Leu Lys Val Asn Gln Pro His Pro Asn
        -1   1               5                  10 agc tgg gcc tca ccc gtc acc gat tgg gcc gcc aac ccc gac ggc acc   192
Ser Trp Ala Ser Pro Val Thr Asp Trp Ala Ala Asn Pro Asp Gly Thr
         15                  20                  25 gga gcc gct ccc gcc gcc atc gcc gcg ccc gac acc ttt tac acc aac   240
Gly Ala Ala Pro Ala Ala Ile Ala Ala Pro Asp Thr Phe Tyr Thr Asn
 30                  35                  40                  45 aac cgc acg ctc cgc acc ccc gcc gtc ggc gtc aac gcc acc ttc ccc   288
Asn Arg Thr Leu Arg Thr Pro Ala Val Gly Val Asn Ala Thr Phe Pro
                 50                  55                  60 ggc ggc gtc ctc ggc cta aac ggc ggc gtc atc ggc ata aaa acc ggc   336
Gly Gly Val Leu Gly Leu Asn Gly Gly Val Ile Gly Ile Lys Thr Gly
                     65                  70                  75 ccc tcc gcc ttc tcc atc gcc ccc aag ctc gtc tcc acc gcc ggc gcc   384
Pro Ser Ala Phe Ser Ile Ala Pro Lys Leu Val Ser Thr Ala Gly Ala
                 80                  85                  90 atc gag tcc tgg ggc aca ccc caa aac ttc cgc gcc gac gac tgg gag   432
Ile Glu Ser Trp Gly Thr Pro Gln Asn Phe Arg Ala Asp Asp Trp Glu
 95                 100                 105 agc aac gcc ccc ttc ccc acc ttc acc gga ctg agg acc gcc tcc aac   480
Ser Asn Ala Pro Phe Pro Thr Phe Thr Gly Leu Arg Thr Ala Ser Asn
110                 115                 120                 125 cat acg ctc aag gtc tcc gtc ggc aaa ctc tcc ggc acc ggc gaa atc   528
His Thr Leu Lys Val Ser Val Gly Lys Leu Ser Gly Thr Gly Glu Ile
                130                 135                 140 cgc gtc cac ggc ggc ggc acc gtc ctc ctc gac gtc acc gac gcc gaa   576
Arg Val His Gly Gly Gly Thr Val Leu Leu Asp Val Thr Asp Ala Glu
                145                 150                 155 aac tac ctc ggc acc ctc tgc gtc gcc tcc ggc gcg ttg aac ttc gac   624
Asn Tyr Leu Gly Thr Leu Cys Val Ala Ser Gly Ala Leu Asn Phe Asp
                160                 165                 170 aac gcc gtc ttc tcc tcc ggc ccc ctc gac atc aag acc ggc gcc acc   672
Asn Ala Val Phe Ser Ser Gly Pro Leu Asp Ile Lys Thr Gly Ala Thr
            175                 180                 185 gtc gtc ctc gac cag gcc gtc tcc ttc gcc ggc ctc gcc gtc gga gcc   720
Val Val Leu Asp Gln Ala Val Ser Phe Ala Gly Leu Ala Val Gly Ala
190                 195                 200                 205 acc gag tat cca ccc ggc aac tac acc ctc gcc gcc ctg caa gcc gcc   768
Thr Glu Tyr Pro Pro Gly Asn Tyr Thr Leu Ala Ala Leu Gln Ala Ala
                210                 215                 220 cac ccg ggc gtc ttc acc ggc acc gcc gcc ggc tcc atc acc gtc cgc   816
His Pro Gly Val Phe Thr Gly Thr Ala Ala Gly Ser Ile Thr Val Arg
            225                 230                 235 gcc ccg cgc acc tgg tat ctc acc gtc agc cag ggc tcc cag aac tgg   864
Ala Pro Arg Thr Trp Tyr Leu Thr Val Ser Gln Gly Ser Gln Asn Trp
                240                 245                 250 acc gag gcc ttc ctc tcc aac tgg aac tcc gcc gcc aac ggc tcc ggc   912
Thr Glu Ala Phe Leu Ser Asn Trp Asn Ser Ala Ala Asn Gly Ser Gly
255                 260                 265 gtc gcc ccg aac tac atc aac ggc cac gac atc tac ctc aac cag gtg   960
```

```
        Val Ala Pro Asn Tyr Ile Asn Gly His Asp Ile Tyr Leu Asn Gln Val
        270             275                 280                 285 aac aac cgc gag ctc cgc acg ccc tac acc gcc agc acc ttc acc ggc           1008
Asn Asn Arg Glu Leu Arg Thr Pro Tyr Thr Ala Ser Thr Phe Thr Gly
                    290                 295                 300 ggc acc ctc gcc ctc acc ttc ggc tcg aag ctc gtc gtc aag acc tca           1056
Gly Thr Leu Ala Leu Thr Phe Gly Ser Lys Leu Val Val Lys Thr Ser
            305                 310                 315 ccc aac ctc gtc agc acc atc ccc gcc ctc gtc acc tcc ggc acc ccg           1104
Pro Asn Leu Val Ser Thr Ile Pro Ala Leu Val Thr Ser Gly Thr Pro
            320                 325                 330 cag ttc gcc aac ggc agc ggc agc cgc caa aac ctc gcc atc ggc gac           1152
Gln Phe Ala Asn Gly Ser Gly Ser Arg Gln Asn Leu Ala Ile Gly Asp
        335                 340                 345 tgg gac atc atc tcc ggc acc agc cgc ctc gtc gcc ggc tcc acc cgg           1200
Trp Asp Ile Ile Ser Gly Thr Ser Arg Leu Val Ala Gly Ser Thr Arg
350                 355                 360                 365 tcc ctc ggc ttc gac atc ggc tgg ctc acc ggc gcg ggc aac ctc cag           1248
Ser Leu Gly Phe Asp Ile Gly Trp Leu Thr Gly Ala Gly Asn Leu Gln
                370                 375                 380 acc gaa ggc ggc ggc tcg ttc ttc ctc cgc ctc atc gac ggc tcc ggc           1296
Thr Glu Gly Gly Gly Ser Phe Phe Leu Arg Leu Ile Asp Gly Ser Gly
            385                 390                 395 tac acc ggc gcc atc aac cac aac tcc ggc gcc ctc cgc ttc gag tcc           1344
Tyr Thr Gly Ala Ile Asn His Asn Ser Gly Ala Leu Arg Phe Glu Ser
            400                 405                 410 gtc ttc tcc acc gcc ggt gcc ctc aac atc ggc gcc tcc gcg acc gtc           1392
Val Phe Ser Thr Ala Gly Ala Leu Asn Ile Gly Ala Ser Ala Thr Val
        415                 420                 425 cac ctc gac aag ccc gtc tat gtc agc ggc ctc tcc gtc gcc ggc gtc           1440
His Leu Asp Lys Pro Val Tyr Val Ser Gly Leu Ser Val Ala Gly Val
430                 435                 440                 445 gcc aaa ccc gcc ggc atc cac acc tac gcc tcg ctg aac gcc gcg cat           1488
Ala Lys Pro Ala Gly Ile His Thr Tyr Ala Ser Leu Asn Ala Ala His
                450                 455                 460 ccc gcg cag ttc aac gcc ggc gcc gcg ccc gga ctc gtc gcc gtt tac           1536
Pro Ala Gln Phe Asn Ala Gly Ala Ala Pro Gly Leu Val Ala Val Tyr
            465                 470                 475 aca ccc aac act gcc gcc ccc gtc cgc atg aac ggc gtc aac ctc tcc           1584
Thr Pro Asn Thr Ala Ala Pro Val Arg Met Asn Gly Val Asn Leu Ser
        480                 485                 490 ggc ccc gaa tcc gtc ggc ggc gcc ggc acg ccc ttt ccc ggc acc tac           1632
Gly Pro Glu Ser Val Gly Gly Ala Gly Thr Pro Phe Pro Gly Thr Tyr
    495                 500                 505 ggc ttc cag tgg att tac ccc acc gtc gcc gac tac gac tac tac gcc           1680
Gly Phe Gln Trp Ile Tyr Pro Thr Val Ala Asp Tyr Asp Tyr Tyr Ala
510                 515                 520                 525 gcc aag ggc ctt aac ctc atc cgc atc cca ttc cgc tgg gaa cgc atg           1728
Ala Lys Gly Leu Asn Leu Ile Arg Ile Pro Phe Arg Trp Glu Arg Met
                530                 535                 540 caa ggc acc ctt aac ggt ccc ctc atc gcc gcc gaa ctc gct cgc atg           1776
Gln Gly Thr Leu Asn Gly Pro Leu Ile Ala Ala Glu Leu Ala Arg Met
            545                 550                 555 gac aac gcc atc gcc ctc gcc tcc gcg cgc ggc atg aag gtc atc ctc           1824
Asp Asn Ala Ile Ala Leu Ala Ser Ala Arg Gly Met Lys Val Ile Leu
        560                 565                 570 gat atg cat aac tac gcg cgc tac cgc acc ccg acc gcg agc tac gtg           1872
Asp Met His Asn Tyr Ala Arg Tyr Arg Thr Pro Thr Ala Ser Tyr Val
    575                 580                 585
```

| | | | | | | | | | | | | | | | | |
|---|---|---|---|---|---|---|---|---|---|---|---|---|---|---|---|---|
| ttt | ggt | gac | gcc | cag | ctc | ccc | gcc | tcc | gcc | ttc | gcc | gac | gtc | tgg | cgc | 1920 |
| Phe | Gly | Asp | Ala | Gln | Leu | Pro | Ala | Ser | Ala | Phe | Ala | Asp | Val | Trp | Arg | |
| 590 | | | | 595 | | | | 600 | | | | 605 | | | | |
| aag | ctc | gcc | gat | cac | tac | aaa | aac | gaa | ccc | gcc | atc | tac | ggt | ttc | gac | 1968 |
| Lys | Leu | Ala | Asp | His | Tyr | Lys | Asn | Glu | Pro | Ala | Ile | Tyr | Gly | Phe | Asp | |
| | | | 610 | | | | | 615 | | | | | 620 | | | |
| atc | atg | aac | gag | ccg | cac | agc | atg | ccc | acc | ccc | acc | acc | tgg | ccc | acc | 2016 |
| Ile | Met | Asn | Glu | Pro | His | Ser | Met | Pro | Thr | Pro | Thr | Thr | Trp | Pro | Thr | |
| | | 625 | | | | | 630 | | | | | 635 | | | | |
| tac | gcc | caa | gcc | gcc | gtc | cac | gcc | atc | cgc | gag | gtc | aac | ctc | gac | acc | 2064 |
| Tyr | Ala | Gln | Ala | Ala | Val | His | Ala | Ile | Arg | Glu | Val | Asn | Leu | Asp | Thr | |
| | 640 | | | | | 645 | | | | | 650 | | | | | |
| tgg | atc | atc | gta | gag | ggc | gag | acc | tat | gcc | aac | tcc | tgg | aaa | ttc | ggg | 2112 |
| Trp | Ile | Ile | Val | Glu | Gly | Glu | Thr | Tyr | Ala | Asn | Ser | Trp | Lys | Phe | Gly | |
| | 655 | | | | | 660 | | | | | 665 | | | | | |
| gaa | aaa | aat | ccc | cac | ctc | cac | aac | gtg | cgc | gac | ccc | gtc | ggc | cgc | ctc | 2160 |
| Glu | Lys | Asn | Pro | His | Leu | His | Asn | Val | Arg | Asp | Pro | Val | Gly | Arg | Leu | |
| 670 | | | | 675 | | | | 680 | | | | 685 | | | | |
| atg | ttc | tcc | gcc | cac | tcc | tac | tgg | tgc | aaa | aac | ggc | gac | gac | aga | tac | 2208 |
| Met | Phe | Ser | Ala | His | Ser | Tyr | Trp | Cys | Lys | Asn | Gly | Asp | Asp | Arg | Tyr | |
| | | | | 690 | | | | | 695 | | | | | 700 | | |
| ggc | acc | tac | gac | gcg | gaa | aac | ggc | cac | ccc | cag | atg | ggc | gtg | gac | agc | 2256 |
| Gly | Thr | Tyr | Asp | Ala | Glu | Asn | Gly | His | Pro | Gln | Met | Gly | Val | Asp | Ser | |
| | | 705 | | | | | 710 | | | | | 715 | | | | |
| ctc | aag | cac | ttc | gtt | gac | tgg | ctc | cgc | aaa | cac | aac | gcc | cac | ggc | ttc | 2304 |
| Leu | Lys | His | Phe | Val | Asp | Trp | Leu | Arg | Lys | His | Asn | Ala | His | Gly | Phe | |
| | 720 | | | | | 725 | | | | | 730 | | | | | |
| gtc | ggc | gaa | tac | ggc | gtc | ccc | aac | aac | gac | ccc | cgc | tgg | ctc | gaa | gtc | 2352 |
| Val | Gly | Glu | Tyr | Gly | Val | Pro | Asn | Asn | Asp | Pro | Arg | Trp | Leu | Glu | Val | |
| | 735 | | | | | 740 | | | | | 745 | | | | | |
| ctt | gaa | aac | gcg | ctc | atc | tac | ctg | gcg | aat | gaa | aac | atc | agc | ggc | acc | 2400 |
| Leu | Glu | Asn | Ala | Leu | Ile | Tyr | Leu | Ala | Asn | Glu | Asn | Ile | Ser | Gly | Thr | |
| 750 | | | | 755 | | | | 760 | | | | 765 | | | | |
| tac | tgg | gcc | ggc | ggc | gcc | tgg | ctc | gcc | ggc | agc | cac | atc | agc | tgc | cac | 2448 |
| Tyr | Trp | Ala | Gly | Gly | Ala | Trp | Leu | Ala | Gly | Ser | His | Ile | Ser | Cys | His | |
| | | | 770 | | | | | 775 | | | | | 780 | | | |
| ccg | tcc | tcc | aac | tac | acc | gtg | gac | cgc | ccc | gtc | atg | agc | gtc | ctc | caa | 2496 |
| Pro | Ser | Ser | Asn | Tyr | Thr | Val | Asp | Arg | Pro | Val | Met | Ser | Val | Leu | Gln | |
| | | 785 | | | | | 790 | | | | | 795 | | | | |
| aac | tac | ccg | taa | | | | | | | | | | | | | 2508 |
| Asn | Tyr | Pro | | | | | | | | | | | | | | |
| | | 800 | | | | | | | | | | | | | | |

<210> SEQ ID NO 6
<211> LENGTH: 835
<212> TYPE: PRT
<213> ORGANISM: Unknown
<220> FEATURE:
<223> OTHER INFORMATION: Synthetic Construct

<400> SEQUENCE: 6

Met Lys His His His Thr Thr Pro His Thr Pro Arg Arg Thr Leu Leu
-35                 -30                 -25                 -20

Arg Ser Leu Ala Gly Leu Leu Ala Leu Ala Thr Gly Leu Ala Ser Thr
            -15                 -10                  -5

Ala His Ala Ala Asp Tyr Tyr Leu Lys Val Asn Gln Pro His Pro Asn
        -1   1               5                  10

Ser Trp Ala Ser Pro Val Thr Asp Trp Ala Ala Asn Pro Asp Gly Thr
            15                  20                  25

Gly Ala Ala Pro Ala Ala Ile Ala Ala Pro Asp Thr Phe Tyr Thr Asn

```
                30                  35                  40                  45

Asn Arg Thr Leu Arg Thr Pro Ala Val Gly Val Asn Ala Thr Phe Pro
                    50                  55                  60

Gly Gly Val Leu Gly Leu Asn Gly Gly Val Ile Gly Ile Lys Thr Gly
                65                  70                  75

Pro Ser Ala Phe Ser Ile Ala Pro Lys Leu Val Ser Thr Ala Gly Ala
            80                  85                  90

Ile Glu Ser Trp Gly Thr Pro Gln Asn Phe Arg Ala Asp Asp Trp Glu
        95                  100                 105

Ser Asn Ala Pro Phe Pro Thr Phe Thr Gly Leu Arg Thr Ala Ser Asn
110                 115                 120                 125

His Thr Leu Lys Val Ser Val Gly Lys Leu Ser Gly Thr Gly Glu Ile
                130                 135                 140

Arg Val His Gly Gly Gly Thr Val Leu Leu Asp Val Thr Asp Ala Glu
            145                 150                 155

Asn Tyr Leu Gly Thr Leu Cys Val Ala Ser Gly Ala Leu Asn Phe Asp
        160                 165                 170

Asn Ala Val Phe Ser Ser Gly Pro Leu Asp Ile Lys Thr Gly Ala Thr
    175                 180                 185

Val Val Leu Asp Gln Ala Val Ser Phe Ala Gly Leu Ala Val Gly Ala
190                 195                 200                 205

Thr Glu Tyr Pro Pro Gly Asn Tyr Thr Leu Ala Ala Leu Gln Ala Ala
                210                 215                 220

His Pro Gly Val Phe Thr Gly Thr Ala Ala Gly Ser Ile Thr Val Arg
            225                 230                 235

Ala Pro Arg Thr Trp Tyr Leu Thr Val Ser Gln Gly Ser Gln Asn Trp
        240                 245                 250

Thr Glu Ala Phe Leu Ser Asn Trp Asn Ser Ala Ala Asn Gly Ser Gly
    255                 260                 265

Val Ala Pro Asn Tyr Ile Asn Gly His Asp Ile Tyr Leu Asn Gln Val
270                 275                 280                 285

Asn Asn Arg Glu Leu Arg Thr Pro Tyr Thr Ala Ser Thr Phe Thr Gly
                290                 295                 300

Gly Thr Leu Ala Leu Thr Phe Gly Ser Lys Leu Val Val Lys Thr Ser
            305                 310                 315

Pro Asn Leu Val Ser Thr Ile Pro Ala Leu Val Thr Ser Gly Thr Pro
        320                 325                 330

Gln Phe Ala Asn Gly Ser Gly Ser Arg Gln Asn Leu Ala Ile Gly Asp
    335                 340                 345

Trp Asp Ile Ile Ser Gly Thr Ser Arg Leu Val Ala Gly Ser Thr Arg
350                 355                 360                 365

Ser Leu Gly Phe Asp Ile Gly Trp Leu Thr Gly Ala Gly Asn Leu Gln
                370                 375                 380

Thr Glu Gly Gly Gly Ser Phe Phe Leu Arg Leu Ile Asp Gly Ser Gly
            385                 390                 395

Tyr Thr Gly Ala Ile Asn His Asn Ser Gly Ala Leu Arg Phe Glu Ser
        400                 405                 410

Val Phe Ser Thr Ala Gly Ala Leu Asn Ile Gly Ala Ser Ala Thr Val
    415                 420                 425

His Leu Asp Lys Pro Val Tyr Val Ser Gly Leu Ser Val Ala Gly Val
430                 435                 440                 445

Ala Lys Pro Ala Gly Ile His Thr Tyr Ala Ser Leu Asn Ala Ala His
                450                 455                 460
```

Pro Ala Gln Phe Asn Ala Gly Ala Pro Gly Leu Val Ala Val Tyr
        465                 470                 475

Thr Pro Asn Thr Ala Ala Pro Val Arg Met Asn Gly Val Asn Leu Ser
        480                 485                 490

Gly Pro Glu Ser Val Gly Ala Gly Thr Pro Phe Pro Gly Thr Tyr
        495                 500                 505

Gly Phe Gln Trp Ile Tyr Pro Thr Val Ala Asp Tyr Asp Tyr Ala
510                 515                 520                 525

Ala Lys Gly Leu Asn Leu Ile Arg Ile Pro Phe Arg Trp Glu Arg Met
                530                 535                 540

Gln Gly Thr Leu Asn Gly Pro Leu Ile Ala Ala Glu Leu Ala Arg Met
            545                 550                 555

Asp Asn Ala Ile Ala Leu Ala Ser Ala Arg Gly Met Lys Val Ile Leu
        560                 565                 570

Asp Met His Asn Tyr Ala Arg Tyr Arg Thr Pro Thr Ala Ser Tyr Val
    575                 580                 585

Phe Gly Asp Ala Gln Leu Pro Ala Ser Ala Phe Ala Asp Val Trp Arg
590                 595                 600                 605

Lys Leu Ala Asp His Tyr Lys Asn Glu Pro Ala Ile Tyr Gly Phe Asp
                610                 615                 620

Ile Met Asn Glu Pro His Ser Met Pro Thr Pro Thr Thr Trp Pro Thr
            625                 630                 635

Tyr Ala Gln Ala Ala Val His Ala Ile Arg Glu Val Asn Leu Asp Thr
        640                 645                 650

Trp Ile Ile Val Glu Gly Glu Thr Tyr Ala Asn Ser Trp Lys Phe Gly
    655                 660                 665

Glu Lys Asn Pro His Leu His Asn Val Arg Asp Pro Val Gly Arg Leu
670                 675                 680                 685

Met Phe Ser Ala His Ser Tyr Trp Cys Lys Asn Gly Asp Asp Arg Tyr
                690                 695                 700

Gly Thr Tyr Asp Ala Glu Asn Gly His Pro Gln Met Gly Val Asp Ser
            705                 710                 715

Leu Lys His Phe Val Asp Trp Leu Arg Lys His Asn Ala His Gly Phe
        720                 725                 730

Val Gly Glu Tyr Gly Val Pro Asn Asn Asp Pro Arg Trp Leu Glu Val
    735                 740                 745

Leu Glu Asn Ala Leu Ile Tyr Leu Ala Asn Glu Asn Ile Ser Gly Thr
750                 755                 760                 765

Tyr Trp Ala Gly Gly Ala Trp Leu Ala Gly Ser His Ile Ser Cys His
                770                 775                 780

Pro Ser Asn Tyr Thr Val Asp Arg Pro Val Met Ser Val Leu Gln
            785                 790                 795

Asn Tyr Pro
        800

<210> SEQ ID NO 7
<211> LENGTH: 2082
<212> TYPE: DNA
<213> ORGANISM: Pseudomonas stutzeri
<220> FEATURE:
<221> NAME/KEY: CDS
<222> LOCATION: (1)..(2079)
<220> FEATURE:
<221> NAME/KEY: sig_peptide
<222> LOCATION: (1)..(108)
<220> FEATURE:

<221> NAME/KEY: mat_peptide
<222> LOCATION: (109)..(2079)

<400> SEQUENCE: 7

| | | | | | | | | | | | | | | | | |
|---|---|---|---|---|---|---|---|---|---|---|---|---|---|---|---|---|
| atg | tcc | acc | aac | ctg | ttt | tcc | ggt | gcc | cgc | aag | gca | ctc | gtc | gct | tcc | 48 |
| Met | Ser | Thr | Asn | Leu | Phe | Ser | Gly | Ala | Arg | Lys | Ala | Leu | Val | Ala | Ser | |
| | -35 | | | | -30 | | | | | -25 | | | | | | |
| atc | gct | gcc | gct | gtt | ctg | ctg | ggt | ggc | gcc | act | gtt | gta | acc | acg | cct | 96 |
| Ile | Ala | Ala | Ala | Val | Leu | Leu | Gly | Gly | Ala | Thr | Val | Val | Thr | Thr | Pro | |
| -20 | | | | -15 | | | | | -10 | | | | | -5 | | |
| tat | gcc | gct | gca | tcc | tcg | gtt | gcc | gct | gta | tcg | gtt | tcc | gcc | aag | atc | 144 |
| Tyr | Ala | Ala | Ala | Ser | Ser | Val | Ala | Ala | Val | Ser | Val | Ser | Ala | Lys | Ile | |
| | | | -1 | 1 | | | | 5 | | | | | | 10 | | |
| aac | gcg | ttc | acc | aac | agc | gat | tgg | ctg | aac | ggt | atc | tgg | cgc | acc | ggc | 192 |
| Asn | Ala | Phe | Thr | Asn | Ser | Asp | Trp | Leu | Asn | Gly | Ile | Trp | Arg | Thr | Gly | |
| | | 15 | | | | | 20 | | | | | 25 | | | | |
| gcc | ggc | ttc | tcg | atc | ccc | gcc | acc | tcc | gca | aac | cgc | gcc | gcg | ttc | gtg | 240 |
| Ala | Gly | Phe | Ser | Ile | Pro | Ala | Thr | Ser | Ala | Asn | Arg | Ala | Ala | Phe | Val | |
| | 30 | | | | | 35 | | | | | 40 | | | | | |
| gcc | ggc | gct | tcg | gta | cga | ctg | gca | gac | ggt | cag | gta | cgc | aag | atc | agc | 288 |
| Ala | Gly | Ala | Ser | Val | Arg | Leu | Ala | Asp | Gly | Gln | Val | Arg | Lys | Ile | Ser | |
| 45 | | | | | 50 | | | | | 55 | | | | | 60 | |
| cgc | gcg | caa | atc | gtc | ggc | agc | aac | atg | agc | atc | ttc | ctg | gaa | ggt | gca | 336 |
| Arg | Ala | Gln | Ile | Val | Gly | Ser | Asn | Met | Ser | Ile | Phe | Leu | Glu | Gly | Ala | |
| | | | | 65 | | | | | 70 | | | | | 75 | | |
| aag | ctg | gac | ggc | aac | aag | gtt | ggc | gca | ccg | caa | gtg | gtc | acc | atc | ggc | 384 |
| Lys | Leu | Asp | Gly | Asn | Lys | Val | Gly | Ala | Pro | Gln | Val | Val | Thr | Ile | Gly | |
| | | | 80 | | | | | 85 | | | | | 90 | | | |
| agc | acg | gcc | gta | acg | gcc | ccg | gac | act | tct | gct | ccg | atc | act | aca | ccg | 432 |
| Ser | Thr | Ala | Val | Thr | Ala | Pro | Asp | Thr | Ser | Ala | Pro | Ile | Thr | Thr | Pro | |
| | | 95 | | | | | 100 | | | | | 105 | | | | |
| cct | acc | gtt | act | gcg | cac | tcg | acc | agc | atc | aac | gca | ttc | acc | aac | aat | 480 |
| Pro | Thr | Val | Thr | Ala | His | Ser | Thr | Ser | Ile | Asn | Ala | Phe | Thr | Asn | Asn | |
| | | | 110 | | | | | 115 | | | | | 120 | | | |
| gat | tgg | ctc | aat | ggt | gta | tgg | cgt | aag | tcg | ccg | ggc | ttc | tcc | att | ccg | 528 |
| Asp | Trp | Leu | Asn | Gly | Val | Trp | Arg | Lys | Ser | Pro | Gly | Phe | Ser | Ile | Pro | |
| 125 | | | | | 130 | | | | | 135 | | | | | 140 | |
| gca | agc | gct | gcc | aac | aag | gct | gct | ttc | aaa | gtt | gga | gcg | aca | gca | aaa | 576 |
| Ala | Ser | Ala | Ala | Asn | Lys | Ala | Ala | Phe | Lys | Val | Gly | Ala | Thr | Ala | Lys | |
| | | | | 145 | | | | | 150 | | | | | 155 | | |
| ctg | gca | gat | ggc | cag | gtt | cgc | aaa | att | acc | cag | gta | caa | gtt | gtt | ggc | 624 |
| Leu | Ala | Asp | Gly | Gln | Val | Arg | Lys | Ile | Thr | Gln | Val | Gln | Val | Val | Gly | |
| | | | 160 | | | | | 165 | | | | | 170 | | | |
| gcc | aat | atg | agc | gtc | tat | ctg | gaa | ggt | gcg | gca | gtt | aac | gga | agt | gtc | 672 |
| Ala | Asn | Met | Ser | Val | Tyr | Leu | Glu | Gly | Ala | Ala | Val | Asn | Gly | Ser | Val | |
| | | 175 | | | | | 180 | | | | | 185 | | | | |
| gtc | ggc | gca | ccc | aac | aag | ttg | gcg | ctg | gct | aca | act | tcg | act | acc | agc | 720 |
| Val | Gly | Ala | Pro | Asn | Lys | Leu | Ala | Leu | Ala | Thr | Thr | Ser | Thr | Thr | Ser | |
| | 190 | | | | | 195 | | | | | 200 | | | | | |
| ccg | gct | ccg | act | ccg | gcg | ccc | agt | gct | ccg | acc | cct | tcg | gtc | atc | gcc | 768 |
| Pro | Ala | Pro | Thr | Pro | Ala | Pro | Ser | Ala | Pro | Thr | Pro | Ser | Val | Ile | Ala | |
| 205 | | | | | 210 | | | | | 215 | | | | | 220 | |
| acc | agc | aac | ctg | aac | aac | tac | acc | aat | gct | caa | tgg | ctc | aac | ggt | atg | 816 |
| Thr | Ser | Asn | Leu | Asn | Asn | Tyr | Thr | Asn | Ala | Gln | Trp | Leu | Asn | Gly | Met | |
| | | | | 225 | | | | | 230 | | | | | 235 | | |
| tac | cgt | acc | gct | gca | ggc | ttc | tcc | atc | cag | gca | agc | agc | gcc | aac | gtg | 864 |
| Tyr | Arg | Thr | Ala | Ala | Gly | Phe | Ser | Ile | Gln | Ala | Ser | Ser | Ala | Asn | Val | |
| | | | 240 | | | | | 245 | | | | | 250 | | | |
| gcg | gca | ttc | aag | gct | ggc | gct | ttg | gtg | agg | ctc | gct | gat | ggt | cag | acc | 912 |
| Ala | Ala | Phe | Lys | Ala | Gly | Ala | Leu | Val | Arg | Leu | Ala | Asp | Gly | Gln | Thr | |

-continued

| | | |
|---|---|---|
| 255 | 260 | 265 |

```
cgc aag gtg ctg cgc gct cag ctg gtc ggc agc aac atg agc gtc ttt    960
Arg Lys Val Leu Arg Ala Gln Leu Val Gly Ser Asn Met Ser Val Phe
    270             275             280 ctt gac ggc gcg gta atc aac ggt acg acc ctg ggc tat ccg aag acc   1008
Leu Asp Gly Ala Val Ile Asn Gly Thr Thr Leu Gly Tyr Pro Lys Thr
285             290             295             300 atc tcg gtg gtc agt acg tcg acc ggc act cct tcg tct cct gct ctg   1056
Ile Ser Val Val Ser Thr Ser Thr Gly Thr Pro Ser Ser Pro Ala Leu
        305             310             315 act acc cca ccg gta gag cca gca ccg gct ccg gtg ccc acc gca cct   1104
Thr Thr Pro Pro Val Glu Pro Ala Pro Ala Pro Val Pro Thr Ala Pro
            320             325             330 gac acc acc aat ggc aag ccg ctg ctg gtt ggc gtc aat ctg tcc ggc   1152
Asp Thr Thr Asn Gly Lys Pro Leu Leu Val Gly Val Asn Leu Ser Gly
                335             340             345 gcc ggc ttc ggt ccc tcg gtt gtt ccc ggc aag cat ggc acc aac tac   1200
Ala Gly Phe Gly Pro Ser Val Val Pro Gly Lys His Gly Thr Asn Tyr
350             355             360 acc tat cct gcc gag tcg tac tac aag aag tat tcc gac ctg ggc atg   1248
Thr Tyr Pro Ala Glu Ser Tyr Tyr Lys Lys Tyr Ser Asp Leu Gly Met
365             370             375             380 ccg ctg gtt cgc ctg ccg ttc ctc tgg gag cgt atc cag ccc aag ctg   1296
Pro Leu Val Arg Leu Pro Phe Leu Trp Glu Arg Ile Gln Pro Lys Leu
            385             390             395 aac tct ccg ctg aac gcc gag gag ttc gcc cgt ctg aag cag tcg ctg   1344
Asn Ser Pro Leu Asn Ala Glu Glu Phe Ala Arg Leu Lys Gln Ser Leu
                400             405             410 gat ttc gcg cag aag cac aac gtc aag gtg att ctc gac ctg cac aac   1392
Asp Phe Ala Gln Lys His Asn Val Lys Val Ile Leu Asp Leu His Asn
            415             420             425 tac tac cgt tat tac ggc aag ctg atc ggc tcc aaa gaa gtg ccc atc   1440
Tyr Tyr Arg Tyr Tyr Gly Lys Leu Ile Gly Ser Lys Glu Val Pro Ile
        430             435             440 agt tcc ttc gcc gcg gta tgg aag cag atc gtg cag caa gta gtg aac   1488
Ser Ser Phe Ala Ala Val Trp Lys Gln Ile Val Gln Gln Val Val Asn
445             450             455             460 cac ccg gcc gtc gaa ggc tac ggc ctg atg aac gag ccg cac tcg acc   1536
His Pro Ala Val Glu Gly Tyr Gly Leu Met Asn Glu Pro His Ser Thr
            465             470             475 aac ggg ctc tgg ccg cag gct gcc ctg gcg gct gct cag gca atc cgc   1584
Asn Gly Leu Trp Pro Gln Ala Ala Leu Ala Ala Ala Gln Ala Ile Arg
                480             485             490 acc gtc gac tcc aag cgc tgg atc tac gta gca ggc gat cgc tgg tcg   1632
Thr Val Asp Ser Lys Arg Trp Ile Tyr Val Ala Gly Asp Arg Trp Ser
        495             500             505 agc gct ttc cac tgg ccg cac tac aac act cag ctg gtc acc aac ccg   1680
Ser Ala Phe His Trp Pro His Tyr Asn Thr Gln Leu Val Thr Asn Pro
510             515             520 tgg atg cgc gat ccg aag aac aat ctg gtt tac gaa gcg cac atg tac   1728
Trp Met Arg Asp Pro Lys Asn Asn Leu Val Tyr Glu Ala His Met Tyr
525             530             535             540 gtg gac aag gat ttc tcg ggc aac tac ttc gac aag gcc gag aag ttc   1776
Val Asp Lys Asp Phe Ser Gly Asn Tyr Phe Asp Lys Ala Glu Lys Phe
            545             550             555 gac ccg atg att ggc gtc aac cgc gtc aag ccc ttc gtc gac tgg ctc   1824
Asp Pro Met Ile Gly Val Asn Arg Val Lys Pro Phe Val Asp Trp Leu
                560             565             570 aag cag cac aaa ctg cgc ggc tac atc ggt gag cac ggc gta ccg gat   1872
Lys Gln His Lys Leu Arg Gly Tyr Ile Gly Glu His Gly Val Pro Asp
```

-continued

```
Lys Gln His Lys Leu Arg Gly Tyr Ile Gly Glu His Gly Val Pro Asp
        575                 580                 585 ttc tcg ccc tcg gcc atc gtc gca acc gat aac ctg ctg gcc tac ctg      1920
Phe Ser Pro Ser Ala Ile Val Ala Thr Asp Asn Leu Leu Ala Tyr Leu
        590                 595                 600 cgt cag aac tgc atc ccg agc acc tat tgg gct gcc ggt ccc tgg tgg      1968
Arg Gln Asn Cys Ile Pro Ser Thr Tyr Trp Ala Ala Gly Pro Trp Trp
605                 610                 615                 620 ggc gag tac gcg atg tcc ctg gac gta agc agc ggc aag cac cgt ccg      2016
Gly Glu Tyr Ala Met Ser Leu Asp Val Ser Ser Gly Lys His Arg Pro
                625                 630                 635 cag ctg ccg gtt ctg cag aag cac gcc aaa acc gca aac agc tgc acc      2064
Gln Leu Pro Val Leu Gln Lys His Ala Lys Thr Ala Asn Ser Cys Thr
            640                 645                 650 agc atc ggt ccg ctg taa                                              2082
Ser Ile Gly Pro Leu
            655

<210> SEQ ID NO 8
<211> LENGTH: 693
<212> TYPE: PRT
<213> ORGANISM: Pseudomonas stutzeri

<400> SEQUENCE: 8

Met Ser Thr Asn Leu Phe Ser Gly Ala Arg Lys Ala Leu Val Ala Ser
    -35                 -30                 -25

Ile Ala Ala Ala Val Leu Leu Gly Gly Ala Thr Val Val Thr Thr Pro
-20                 -15                 -10                  -5

Tyr Ala Ala Ala Ser Ser Val Ala Val Ser Val Ser Ala Lys Ile
                -1   1               5                  10

Asn Ala Phe Thr Asn Ser Asp Trp Leu Asn Gly Ile Trp Arg Thr Gly
            15                  20                  25

Ala Gly Phe Ser Ile Pro Ala Thr Ser Ala Asn Arg Ala Ala Phe Val
        30                  35                  40

Ala Gly Ala Ser Val Arg Leu Ala Asp Gly Gln Val Arg Lys Ile Ser
45                  50                  55                  60

Arg Ala Gln Ile Val Gly Ser Asn Met Ser Ile Phe Leu Glu Gly Ala
                65                  70                  75

Lys Leu Asp Gly Asn Lys Val Gly Ala Pro Gln Val Val Thr Ile Gly
            80                  85                  90

Ser Thr Ala Val Thr Ala Pro Asp Thr Ser Ala Pro Ile Thr Thr Pro
        95                  100                 105

Pro Thr Val Thr Ala His Ser Thr Ser Ile Asn Ala Phe Thr Asn Asn
    110                 115                 120

Asp Trp Leu Asn Gly Val Trp Arg Lys Ser Pro Gly Phe Ser Ile Pro
125                 130                 135                 140

Ala Ser Ala Ala Asn Lys Ala Ala Phe Lys Val Gly Ala Thr Ala Lys
                145                 150                 155

Leu Ala Asp Gly Gln Val Arg Lys Ile Thr Gln Val Gln Val Val Gly
            160                 165                 170

Ala Asn Met Ser Val Tyr Leu Glu Gly Ala Val Asn Gly Ser Val
        175                 180                 185

Val Gly Ala Pro Asn Lys Leu Ala Leu Ala Thr Thr Ser Thr Thr Ser
    190                 195                 200

Pro Ala Pro Thr Pro Ala Pro Ser Ala Pro Thr Pro Ser Val Ile Ala
205                 210                 215                 220
```

```
Thr Ser Asn Leu Asn Asn Tyr Thr Asn Ala Gln Trp Leu Asn Gly Met
            225                 230                 235

Tyr Arg Thr Ala Ala Gly Phe Ser Ile Gln Ala Ser Ser Ala Asn Val
        240                 245                 250

Ala Ala Phe Lys Ala Gly Ala Leu Val Arg Leu Ala Asp Gly Gln Thr
            255                 260                 265

Arg Lys Val Leu Arg Ala Gln Leu Val Gly Ser Asn Met Ser Val Phe
        270                 275                 280

Leu Asp Gly Ala Val Ile Asn Gly Thr Thr Leu Gly Tyr Pro Lys Thr
285                 290                 295                 300

Ile Ser Val Val Ser Thr Ser Thr Gly Thr Pro Ser Ser Pro Ala Leu
                305                 310                 315

Thr Thr Pro Pro Val Glu Pro Ala Pro Ala Pro Val Pro Thr Ala Pro
            320                 325                 330

Asp Thr Thr Asn Gly Lys Pro Leu Leu Val Gly Val Asn Leu Ser Gly
        335                 340                 345

Ala Gly Phe Gly Pro Ser Val Val Pro Gly Lys His Gly Thr Asn Tyr
    350                 355                 360

Thr Tyr Pro Ala Glu Ser Tyr Tyr Lys Lys Tyr Ser Asp Leu Gly Met
365                 370                 375                 380

Pro Leu Val Arg Leu Pro Phe Leu Trp Glu Arg Ile Gln Pro Lys Leu
                385                 390                 395

Asn Ser Pro Leu Asn Ala Glu Glu Phe Ala Arg Leu Lys Gln Ser Leu
            400                 405                 410

Asp Phe Ala Gln Lys His Asn Val Lys Val Ile Leu Asp Leu His Asn
        415                 420                 425

Tyr Tyr Arg Tyr Tyr Gly Lys Leu Ile Gly Ser Lys Glu Val Pro Ile
    430                 435                 440

Ser Ser Phe Ala Ala Val Trp Lys Gln Ile Val Gln Gln Val Val Asn
445                 450                 455                 460

His Pro Ala Val Glu Gly Tyr Gly Leu Met Asn Glu Pro His Ser Thr
                465                 470                 475

Asn Gly Leu Trp Pro Gln Ala Ala Leu Ala Ala Ala Gln Ala Ile Arg
            480                 485                 490

Thr Val Asp Ser Lys Arg Trp Ile Tyr Val Ala Gly Asp Arg Trp Ser
        495                 500                 505

Ser Ala Phe His Trp Pro His Tyr Asn Thr Gln Leu Val Thr Asn Pro
    510                 515                 520

Trp Met Arg Asp Pro Lys Asn Asn Leu Val Tyr Glu Ala His Met Tyr
525                 530                 535                 540

Val Asp Lys Asp Phe Ser Gly Asn Tyr Phe Asp Lys Ala Glu Lys Phe
                545                 550                 555

Asp Pro Met Ile Gly Val Asn Arg Val Lys Pro Phe Val Asp Trp Leu
            560                 565                 570

Lys Gln His Lys Leu Arg Gly Tyr Ile Gly Glu His Gly Val Pro Asp
        575                 580                 585

Phe Ser Pro Ser Ala Ile Val Ala Thr Asp Asn Leu Leu Ala Tyr Leu
    590                 595                 600

Arg Gln Asn Cys Ile Pro Ser Tyr Trp Ala Ala Gly Pro Trp Trp
605                 610                 615                 620

Gly Glu Tyr Ala Met Ser Leu Asp Val Ser Ser Gly Lys His Arg Pro
                625                 630                 635

Gln Leu Pro Val Leu Gln Lys His Ala Lys Thr Ala Asn Ser Cys Thr
```

```
                640             645             650
Ser Ile Gly Pro Leu
        655

<210> SEQ ID NO 9
<211> LENGTH: 2409
<212> TYPE: DNA
<213> ORGANISM: Artificial
<220> FEATURE:
<223> OTHER INFORMATION: Codon optimized

<400> SEQUENCE: 9
gcagactatt atctgaaagc atcacaaggc gcatcaaatc attggtcatc acatctgaca      60
gattggacag caaatgcaga tggcacaggc gcaaatccga cagttattgg cctggcagat    120
acatttgata caataatcg cacactgaga acaccggcag ttaatgcaac aacaacatat     180
cctggcggag ttctgagact gtcaggcgga gcaggcgtta ttggcatgaa acaggcgga    240
acagcagttg caattgttcc gaaactggtt caacagcag gcacagttga tgcatggcat    300
acaggcacac agtattttag agcagatgat tgggaaaatc ttgcatcagg cacaggcttt   360
acagcactga agcagtcgc aggcagaaca cttaaagttt cagttggcaa actgacaggc    420
tcaggcgaaa caagactgca tggcggaggc gcagttagac tggatgttac agatggcgaa   480
agatatctgg gcgttgttag agtttcatca ggcgcagcag attttgataa taacgttttt    540
gtttcaggac cgctggttat tgaaacaggc gctacagttg ttctggatca gcagtttca    600
tttgcaggcc ttacagttgc tggcacagaa tattcaccgg gaattataca atttgcagca   660
cttcaagcag cacatccgac ggttttttaca agcggcacag caggcggatc aattacagtt   720
agagcaccga aacatggta tctgacagtt aatcaaggcg gagtccaaaa ttggacagaa    780
acatatctga gcaattggaa ttcagcagca aatggatcag gcgttgcacc gacatcaatt    840
aatggctatg actttttatat cgatcaggtc agcaatcgcg aaattagaac accgtcaaca   900
gcatcaacat ttgaggcgg agcgctggca ctggcatctg gcgcaaaact gacactgaaa    960
tcatcacctg gcgttgtttc aacaattccg gcatttgtta atacaaacag cccgattatt   1020
gttaatggcg gtggctcatt tagacaatca ctggcacttg gcgactggga aattgcaagc   1080
ggcattacaa aactgtcagc aggcagcggc agatcactgg gctttgatat tgattatctt   1140
ggcggagctg gcggactggt tacacaaaat ggcggatcat actttctgtc actggatgat   1200
ggctcaggct atacgggcac actgaatcat gcgtcaggcg cactgagatt tgaatcagtt   1260
tttagcacag aaggcgcact tacaattggc tcatcagcaa cagttcatct tgatcaacaa   1320
gtctatgtca caagctttag cgttgcaggc gtcgcaaaag cagcaggcat tcatacatat   1380
gcatcactga atgcagcgca tccggcacaa tttacagctg gcgcagcacc ggactggtt    1440
gcagtttata caccggatac agcaggaccg gttagaatga atggcgtcaa tattagcgga   1500
ccggaatcaa atacagcaaa tcttccggga acatatggct ataactatgt ctatccgaca   1560
gaagcggact ttgattatta tgcatcaaaa ggcctgaacc tgattagaat tccgtttaga   1620
tgggaaagaa tgcagcatgg cctgaatgtt ccgctgaata cagcacaact gggctatatg   1680
gatacagcgg ttgcaagagc atcagcaaga ggcatgaaag ttattctgga catgcataac   1740
tatgcacgct gcaaagttgg aggcgttaca tacaaatttg agatgcaca acttccggca    1800
agcgcatatg cagatgtttg cgcagacttc tcagaccact ataaaaacga accggcaatt   1860
tatggctttg acattatgaa tgaaccgaat ggcctgagcg gaggcgtttg gcctgcgtat   1920
```

```
gcacaagcag cagtcaatgc aattagagaa gttaatctga gcacatgggt tattgtcgaa    1980
ggcgaatttt gggcaaatgc atggggcttt gaaacgaaaa atccgtatct gcataatgtg    2040
agagatccgg ttggcagact gatgttttca gcacattcat attggtcaga tgcaggcacg    2100
gatgtctata aaacatatga tgaagaaggc gcttatccgg aaatgggcgt taataatgtt    2160
aaaccgttta tcgattggct gaaaaaacat gacgcaaaag ctttgttgg cgaatatggc     2220 gttccgaata atgatccgag atggctggtt gtcctggata ttttctggc atatctggca     2280 gcagaaggcg tttcaggcac atattgggct ggcggagcat ggtattcagg ctcaccgatt    2340
agctgccatc cgtcaagcaa ctatacagtt gatagagcag ttatgagcgt cctggaagat    2400
catccgtaa                                                            2409

<210> SEQ ID NO 10
<211> LENGTH: 2452
<212> TYPE: DNA
<213> ORGANISM: Artificial
<220> FEATURE:
<223> OTHER INFORMATION: Codon optimized

<400> SEQUENCE: 10
gcttttagtt catcgatagc atcagcacat catcatcacc atcatccgag agcagattgg      60
tatctggata aaaatcaagc aagatatgcg agctgggata cactggcaga ttggaaaccg     120
aatccggatg gctcaggctc aaatccgtca gcactgtcac cgtcagatac atatcatctg     180
aatggcttta tgctgagaac accggaaggc ggatcaacat atacatttac aggcggactg     240
ctgagcctgg caataatgc agataatttt gcgctgaaaa caacaggctc aggcgtttca     300
attattccgg cactgagaac aacagcaggc ctggttcaaa atgttggcag cggcacacaa     360
aatctgcaag ttggccatta tcaaaatctg tcaggcacaa caagctatta tgcacaaaca     420
ggcagaggcc tgaatctggc aattacaaca ctggttggct caggacagtt tagatttat     480 ggcggaggca catattatct gtctctggca aattcaccga catatgatgg cgatatttat     540
gtccaaagcg gcacaattga ttttaacaat gatctggcga cagcaggcac actgacagtt     600
aatacaggcg caaaagttgc actggatcaa gcagttacgt ttacaggact gacaattgca     660
ggcacagcat atccggttgg caattattca tatgcagcac tgcaagcagc acatccggca     720 gttttgtt  ctggcacatc aggcggagca attaatgtta gagcaccgag aaattggtac     780
ttgtcaacac atcagccggt tggcgcatca tggaatacac ttgcgcattg gagagcaaac     840
ccggatggaa caggcgctac agcagattca attaatagct ttgacaacta tatcaaccag     900
gtcagcggca gaacactgcg cacaccggaa acaacagcga catttgctgg cggatcactg     960
gttctggcag atggcggaaa tcttttcactg aaagcaccgg caggccattc atcaacaatt    1020
ccggcatttg caacatcagg cagcatttca attacaaacg ctttagctc aattacacaa    1080 ccgctggtta ttggcgattg gcatcttggc gctggcacag cacaagtttc agttccgtca    1140
acatcaacag ttcaactgac agtcgataaa ctgagcggag atggcacact gcaatttcaa    1200
aatggcggta atatacgct gaacattaga ggcgcatcag cttttacagg cacattaaga    1260
catctgagcg gaacacttac agttgcatca caaattggca caggcggaac attagttgtt    1320
gaatcaacag gcgcagttaa actggatcat ccgggatttt ttacaggtgt tacagtggct    1380
ggcacaccgc tggcaccggg atatcataca tatgcggcac ttaaagcggc tcatcctgcg    1440
agatttccga caggctcaac aaatgcgttt cttgcagttt atcctccgga tacaacagga    1500
ccggcacata tgtttggcgt taatctggct ggcggagaat ttggaacacc gatgcctggc    1560
```

```
gtttatggca cagattatat ctatccgagc gcagcagcat ttgattatta tcatggcaaa    1620
ggccttaaac tgattcgcct gccgtttaaa tgggaaagac tgcaacatac acttaatgca    1680
ccgctgaatg cagcagaact ggcaagaatt gatacagttg ttggctatgc atcagcaaga    1740
ggcatgaaag ttgttctgga tatgcataac tatgcgcgta gaaaagaatc aggcacgaca    1800
tatctgatcg gcacaggccc tgttacaatg gatgcatttg gagatgtttg gagaagaatc    1860
gcggatcatt ataaaggcaa tccggcaatt tatggctacg gcattatgaa tgaaccgtat    1920
agcacaaata caacgtggcc tcaaatggcg caaacagcag ttaatgcaat tagaacagtt    1980
gatctgacaa cgcatgttat tgttgcaggc gacggctggt caaatgcaac aggctggcgc    2040
tcaaaaaatc cgaatctgga tacacaagat ccggtcggca gactgattta tgaagcacat    2100
tgctattttg acagcaacct ttcaggcacg tatacacaaa gctatgatgc agcaggcgca    2160
catccgatga ttggcgttga tagagttaga gaatttgtcg aatggcttca agaaacaggc    2220
aacaaaggct ttattggaga atatggcgtt ccgggaaatg atccgagatg ctggttgtt     2280 cttgataatt ttctggcata tctggatgca aatggcgtta gcggaacata ttgggcaggc    2340
ggaccgtggt ggggcaatta tccgctgtca tgcgaaccga catcaaatta cacagttgat    2400
aaaccgcaaa tgagcgtcct ggaaaactac aactaaacgc gttaatcaat aa            2452

<210> SEQ ID NO 11
<211> LENGTH: 2403
<212> TYPE: DNA
<213> ORGANISM: Artificial
<220> FEATURE:
<223> OTHER INFORMATION: Codon optimized

<400> SEQUENCE: 11
gcagattatt atctgaaagt taatcaaccg catccgaatt catgggcatc accggttaca      60
gattgggcag caaatccgga tgccacaggc gcagcaccgg cagcaattgc ggcaccggat     120 acatttata  caaataatag aacacttcgc acaccggctg ttggcgttaa tgcaacattt     180
cctggcggag ttctgggcct gaatggcgga gtcattggca ttaaaacagg accgtcagca     240
ttttcaattg caccgaaact ggtttcaaca gcaggcgcaa ttgaatcatg gggcacaccg     300
cagaatttta gagcagatga ttggaatca  aatgcaccgt ttccgacatt tacaggcctg     360
agaacagcat caaatcatac acttaaagtt agcgttggca aactgagcgg aacaggcgaa     420
attagagttc atggcggagg cacagttctg ctggatgtta cagatgcaga aaattatctg     480
ggcacactgt gcgttgcatc aggcgcactg aattttgata tgcagttttt tcatcagga     540 ccgctggata tcaaaacagg cgcaacagtt gttctggatc aagcagtttc atttgcaggc     600
cttgcagttg gagcaacaga atatccgcct ggcaattata cactggcagc actgcaagca     660
gcacatcctg gcgtttttac aggcacagca gcaggatcaa ttacagttag agcaccgaga     720
acatggtatc tgacagtttc acaaggctca caaaattgga cagaagcatt tctgtcaaat     780
tggaattcag cagcaaatgg ctcaggcgtc gcaccgaatt atatcaatgg acatgatatc     840
tatctgaacc aggtcaataa tcgcgaactg agaacaccgt atacagcaag cacgtttaca     900
ggcggaacac tggcactgac atttggctca aaactggttg ttaaaacaag cccgaatctg     960
gttagcacaa ttccggcact ggttacatct ggaacaccgc aatttgcgaa tggcagcggc    1020
tcaagacaaa atctggcaat tggcgattgg atattatct  caggcacatc aagactggtt    1080
gcaggctcaa caagatcact gggctttgat attggctggc tgacaggcgc tggcaatctg    1140
```

| | |
|---|---|
| caaacagaag gcggaggctc atttttctg agactgattg atggatcagg ctatacaggc | 1200 |
| gctattaacc ataattctgg cgctctgaga ttgaaagcg tttttagcac agctggcgca | 1260 |
| cttaatattg gcgcatcagc aacagttcat cttgataaac cggtctatgt tcaggcctt | 1320 |
| agcgttgcag gcgttgcgaa accggcaggc attcatacat atgcatcact taatgcagcg | 1380 |
| catccggcac aatttaatgc aggcgctgct ccgggacttg ttgcagttta tacaccgaac | 1440 |
| acagcagctc cggttagaat gaatggcgtc aatctgtcag gaccggaatc agttggcgga | 1500 |
| gcaggtacac cttttccggg aacatatggc tttcaatgga tttatccgac agtcgcggat | 1560 |
| tatgattatt atgcagcaaa aggccttaac ctgattagaa ttccgtttag atgggaaaga | 1620 |
| atgcaaggca cactgaatgg accgctgatt gcagcggaac tggcaagaat ggataatgca | 1680 |
| attgcgctgg catcagcgag aggcatgaaa gttattctgg atatgcataa ctatgcacgc | 1740 |
| tatagaacac cgacagcatc atatgttttt ggagatgcgc aacttccggc atcagcattt | 1800 |
| gcagatgttt ggagaaaact ggcggatcac tataaaaacg aaccggcaat ttatggcttt | 1860 |
| gacattatga atgaaccgca ttcaatgccg acaccgacaa cgtggccgac atatgcacaa | 1920 |
| gcagcagttc atgcaattag agaagtcaat ctggatacat ggattatcgt tgaaggcgaa | 1980 |
| acatatgcga actcatggaa atttggcgaa aaaaatccgc atctgcataa tgttagagat | 2040 |
| ccggttggca gactgatgtt ttcagcacat tcatattggt gcaaaaatgg cgacgatcgc | 2100 |
| tatggcacgt atgatgcgga aaatggccat ccgcaaatgg gcgttgattc actgaaacat | 2160 |
| tttgttgatt ggctgcgcaa acataatgca catggctttg ttggcgaata tggcgttccg | 2220 |
| aataatgatc cgagatggct ggaagttctg gaaaatgcac tgatttatct ggcgaacgaa | 2280 |
| aacattagcg gcacatattg ggcaggcgga gcatggctgg caggctcaca tatttcatgc | 2340 |
| catccgtcat ctaactatac agttgatcgt ccggttatga gcgtcctgca aaattatccg | 2400 |
| taa | 2403 |

<210> SEQ ID NO 12
<211> LENGTH: 1974
<212> TYPE: DNA
<213> ORGANISM: Artificial
<220> FEATURE:
<223> OTHER INFORMATION: Codon optimized

<400> SEQUENCE: 12

| | |
|---|---|
| tcatcagttg cagcagtttc agtttcagca aaaatcaatg cgtttacgaa tagcgattgg | 60 |
| ctgaatggca tttggagaac aggcgcaggc ttttcaattc cggcaacatc agcaaataga | 120 |
| gcagcatttg ttgcaggcgc atcagttaga ctggcagatg gccaagttag aaaaattagc | 180 |
| agagcacaaa ttgtcggcag caacatgtca atttttctgg aaggcgcaaa actggatggc | 240 |
| aataaagttg gcgcaccgca agttgttaca attggctcaa cagcagttac agcaccggat | 300 |
| acatcagcac cgattacaac accgcctaca gtcacagcac attcaacatc aattaacgcc | 360 |
| tttacaaata tgactggct taacggcgtt tggcgcaaat caccgggatt tagcattccg | 420 |
| gcatctgcag cgaataaagc ggcttttaaa gttggagcaa cagcaaaact gcggatgga | 480 |
| caggttcgca aaattacaca agttcaagtt gttggcgcta acatgagcgt ttatcttgaa | 540 |
| ggcgcagcag tcaatggctc agttgttgga gcaccgaata aactggcact ggcaacaaca | 600 |
| agcacaaacat caccggcacc gacaccggct ccgtcagctc cgacaccgtc agttattgca | 660 |
| acatcaaatc tgaacaacta tacaaatgcg cagtggctga acggaatgta tagaacagca | 720 |
| gcgggatttt ctattcaagc atcaagcgca aatgtcgcag catttaaagc aggcgcactg | 780 |

-continued

```
gtcagacttg ctgatggcca gacaagaaaa gttctgagag cacaactggt tggctcaaat    840
atgtcagtct ttcttgatgg cgctgtcatt aatggcacaa cactgggcta tccgaaaaca    900
atttcagttg ttagcacatc aacaggcaca ccgtcatctc cggcactgac aacacctccg    960
gttgaaccgg ctcctgcacc ggttccgaca gcgcctgata caacaaatgg caaaccgctg   1020
ctggttggcg ttaatctgag cggagcaggc tttggaccga gcgttgttcc gggaaaacat   1080
ggcacaaatt atacatatcc ggcagaaagc tactacaaaa aatactcaga tctgggcatg   1140
ccgctggtta gactgccgtt tctgtgggaa agaattcaac cgaaactgaa ttcaccgctg   1200
aatgcagaag aatttgcaag actgaaacag agcctggatt ttgcgcagaa acataacgtt   1260
aaagtcatcc tggatctgca taactattat cgctattacg gcaaactgat tggcagcaaa   1320
gaagttccga tttcaagctt tgcggcagtc tggaaacaaa ttgttcaaca gttgtcaat    1380
catccggcag ttgaaggcta tggcctgatg aatgaaccgc atagcacaaa tggcctgtgg   1440
cctcaagcag cactggcagc agcacaagca attagaacag ttgatagcaa acgctggatt   1500
tatgtcgcag gcgatagatg gtcatcagca tttcattggc ctcattataa cacacagctg   1560
gttacaaatc cgtggatgag agatccgaaa aataacctgg tttatgaagc gcatatgtat   1620
gtcgacaaag atttagcgg caactacttt gacaaagcgg aaaaatttga tccgatgatt   1680
ggcgtcaatc gcgttaaacc gtttgttgat tggcttaaac agcataaact gcgtggctat   1740
attggcgaac atggcgttcc ggatttttca ccgtcagcaa ttgttgcgac agataatctg   1800
ctggcatatc tgagacaaaa ttgcattccg tcaacatatt gggcagcagg accgtggtgg   1860
ggagaatatg caatgtcact ggatgtttca agcggcaaac atagaccgca acttccggtt   1920
cttcaaaaac atgcaaaaac agcgaatagc tgcacatcaa ttggaccgct gtaa         1974
```

<210> SEQ ID NO 13  
<211> LENGTH: 811  
<212> TYPE: PRT  
<213> ORGANISM: Artificial  
<220> FEATURE:  
<223> OTHER INFORMATION: HISTAG'ed  
<220> FEATURE:  
<221> NAME/KEY: MISC_FEATURE  
<222> LOCATION: (1)..(9)  
<223> OTHER INFORMATION: His tag

<400> SEQUENCE: 13

```
Met His His His His His Pro Arg Ala Asp Tyr Tyr Leu Lys Ala
1               5                   10                  15

Ser Gln Gly Ala Ser Asn His Trp Ser Ser His Leu Thr Asp Trp Thr
            20                  25                  30

Ala Asn Ala Asp Gly Thr Gly Ala Asn Pro Thr Val Ile Gly Leu Ala
        35                  40                  45

Asp Thr Phe Asp Thr Asn Asn Arg Thr Leu Arg Thr Pro Ala Val Asn
    50                  55                  60

Ala Thr Thr Thr Tyr Pro Gly Gly Val Leu Arg Leu Ser Gly Gly Ala
65                  70                  75                  80

Gly Val Ile Gly Met Lys Thr Gly Gly Thr Ala Val Ala Ile Val Pro
                85                  90                  95

Lys Leu Val Ser Thr Ala Gly Thr Val Asp Ala Trp His Thr Gly Thr
            100                 105                 110

Gln Tyr Phe Arg Ala Asp Asp Trp Glu Asn Leu Ala Ser Gly Thr Gly
        115                 120                 125
```

```
Phe Thr Ala Leu Lys Ala Val Ala Gly Arg Thr Leu Lys Val Ser Val
    130                 135                 140

Gly Lys Leu Thr Gly Ser Gly Glu Thr Arg Leu His Gly Gly Gly Ala
145                 150                 155                 160

Val Arg Leu Asp Val Thr Asp Gly Glu Arg Tyr Leu Gly Val Val Arg
                165                 170                 175

Val Ser Ser Gly Ala Ala Asp Phe Asp Asn Asn Val Phe Val Ser Gly
            180                 185                 190

Pro Leu Val Ile Glu Thr Gly Ala Thr Val Val Leu Asp Gln Ala Val
        195                 200                 205

Ser Phe Ala Gly Leu Thr Val Ala Gly Thr Glu Tyr Ser Pro Gly Asn
210                 215                 220

Tyr Thr Phe Ala Ala Leu Gln Ala Ala His Pro Thr Val Phe Thr Ser
225                 230                 235                 240

Gly Thr Ala Gly Gly Ser Ile Thr Val Arg Ala Pro Arg Thr Trp Tyr
                245                 250                 255

Leu Thr Val Asn Gln Gly Gly Val Gln Asn Trp Thr Glu Thr Tyr Leu
            260                 265                 270

Ser Asn Trp Asn Ser Ala Ala Asn Gly Ser Gly Val Ala Pro Thr Ser
        275                 280                 285

Ile Asn Gly Tyr Asp Phe Tyr Ile Asp Gln Val Ser Asn Arg Glu Ile
290                 295                 300

Arg Thr Pro Ser Thr Ala Ser Thr Phe Gly Gly Ala Leu Ala Leu
305                 310                 315                 320

Ala Ser Gly Ala Lys Leu Thr Leu Lys Ser Pro Gly Val Val Ser
                325                 330                 335

Thr Ile Pro Ala Phe Val Asn Thr Asn Ser Pro Ile Ile Val Asn Gly
            340                 345                 350

Gly Gly Ser Phe Arg Gln Ser Leu Ala Leu Gly Asp Trp Glu Ile Ala
        355                 360                 365

Ser Gly Ile Thr Lys Leu Ser Ala Gly Ser Gly Arg Ser Leu Gly Phe
370                 375                 380

Asp Ile Asp Tyr Leu Gly Gly Ala Gly Gly Leu Val Thr Gln Asn Gly
385                 390                 395                 400

Gly Ser Tyr Phe Leu Ser Leu Asp Asp Gly Ser Gly Tyr Thr Gly Thr
                405                 410                 415

Leu Asn His Ala Ser Gly Ala Leu Arg Phe Glu Ser Val Phe Ser Thr
            420                 425                 430

Glu Gly Ala Leu Thr Ile Gly Ser Ser Ala Thr Val His Leu Asp Gln
        435                 440                 445

Gln Val Tyr Val Thr Ser Phe Ser Val Ala Gly Val Ala Lys Ala Ala
450                 455                 460

Gly Ile His Thr Tyr Ala Ser Leu Asn Ala Ala His Pro Ala Gln Phe
465                 470                 475                 480

Thr Ala Gly Ala Ala Pro Gly Leu Val Ala Val Tyr Thr Pro Asp Thr
                485                 490                 495

Ala Gly Pro Val Arg Met Asn Gly Val Asn Ile Ser Gly Pro Glu Ser
            500                 505                 510

Asn Thr Ala Asn Leu Pro Gly Thr Gly Tyr Asn Tyr Val Tyr Pro
        515                 520                 525

Thr Glu Ala Asp Phe Asp Tyr Tyr Ala Ser Lys Gly Leu Asn Leu Ile
530                 535                 540

Arg Ile Pro Phe Arg Trp Glu Arg Met Gln His Gly Leu Asn Val Pro
```

```
                545                 550                 555                 560
Leu Asn Thr Ala Gln Leu Gly Tyr Met Asp Thr Ala Val Ala Arg Ala
                565                 570                 575

Ser Ala Arg Gly Met Lys Val Ile Leu Asp Met His Asn Tyr Ala Arg
            580                 585                 590

Cys Lys Val Gly Gly Val Thr Tyr Lys Phe Gly Asp Ala Gln Leu Pro
        595                 600                 605

Ala Ser Ala Tyr Ala Asp Val Trp Arg Arg Leu Ala Asp His Tyr Lys
    610                 615                 620

Asn Glu Pro Ala Ile Tyr Gly Phe Asp Ile Met Asn Glu Pro Asn Gly
625                 630                 635                 640

Leu Ser Gly Gly Val Trp Pro Ala Tyr Ala Gln Ala Ala Val Asn Ala
                645                 650                 655

Ile Arg Glu Val Asn Leu Ser Thr Trp Val Ile Val Glu Gly Glu Phe
            660                 665                 670

Trp Ala Asn Ala Trp Gly Phe Glu Thr Lys Asn Pro Tyr Leu His Asn
        675                 680                 685

Val Arg Asp Pro Val Gly Arg Leu Met Phe Ser Ala His Ser Tyr Trp
    690                 695                 700

Ser Asp Ala Gly Thr Asp Val Tyr Lys Thr Tyr Asp Glu Glu Gly Ala
705                 710                 715                 720

Tyr Pro Glu Met Gly Val Asn Asn Val Lys Pro Phe Ile Asp Trp Leu
                725                 730                 735

Lys Lys His Asp Ala Lys Gly Phe Val Gly Glu Tyr Gly Val Pro Asn
            740                 745                 750

Asn Asp Pro Arg Trp Leu Val Val Leu Asp Asn Phe Leu Ala Tyr Leu
        755                 760                 765

Ala Ala Glu Gly Val Ser Gly Thr Tyr Trp Ala Gly Ala Trp Tyr
    770                 775                 780

Ser Gly Ser Pro Ile Ser Cys His Pro Ser Ser Asn Tyr Thr Val Asp
785                 790                 795                 800

Arg Ala Val Met Ser Val Leu Glu Asp His Pro
                805                 810

<210> SEQ ID NO 14
<211> LENGTH: 803
<212> TYPE: PRT
<213> ORGANISM: Artificial
<220> FEATURE:
<223> OTHER INFORMATION: His tag'ed
<220> FEATURE:
<221> NAME/KEY: MISC_FEATURE
<222> LOCATION: (1)..(9)
<223> OTHER INFORMATION: His tag

<400> SEQUENCE: 14

Met His His His His His Pro Arg Ala Asp Trp Tyr Leu Asp Lys
1               5                   10                  15

Asn Gln Ala Arg Tyr Ala Ser Trp Asp Thr Leu Ala Asp Trp Lys Pro
            20                  25                  30

Asn Pro Asp Gly Ser Gly Ser Asn Pro Ser Ala Leu Ser Pro Ser Asp
        35                  40                  45

Thr Tyr His Leu Asn Gly Phe Met Leu Arg Thr Pro Glu Gly Gly Ser
    50                  55                  60

Thr Tyr Thr Phe Thr Gly Gly Leu Leu Ser Leu Ala Asn Asn Ala Asp
65                  70                  75                  80
```

```
Asn Phe Ala Leu Lys Thr Thr Gly Ser Gly Val Ser Ile Ile Pro Ala
                 85                  90                  95

Leu Arg Thr Thr Ala Gly Leu Val Gln Asn Val Gly Ser Gly Thr Gln
            100                 105                 110

Asn Leu Gln Val Gly His Tyr Gln Asn Leu Ser Gly Thr Thr Ser Tyr
            115                 120                 125

Tyr Ala Gln Thr Gly Arg Gly Leu Asn Leu Ala Ile Thr Thr Leu Val
        130                 135                 140

Gly Ser Gly Gln Phe Arg Phe Tyr Gly Gly Thr Tyr Tyr Leu Ser
145                 150                 155                 160

Leu Ala Asn Ser Pro Thr Tyr Asp Gly Asp Ile Tyr Val Gln Ser Gly
                165                 170                 175

Thr Ile Asp Phe Asn Asn Asp Leu Ala Thr Ala Gly Thr Leu Thr Val
                180                 185                 190

Asn Thr Gly Ala Lys Val Ala Leu Asp Gln Ala Val Thr Phe Thr Gly
            195                 200                 205

Leu Thr Ile Ala Gly Thr Ala Tyr Pro Val Gly Asn Tyr Ser Tyr Ala
        210                 215                 220

Ala Leu Gln Ala Ala His Pro Ala Val Phe Val Ser Gly Thr Ser Gly
225                 230                 235                 240

Gly Ala Ile Asn Val Arg Ala Pro Arg Asn Trp Tyr Leu Ser Thr His
                245                 250                 255

Gln Pro Val Gly Ala Ser Trp Asn Thr Leu Ala His Trp Arg Ala Asn
            260                 265                 270

Pro Asp Gly Thr Gly Ala Thr Ala Asp Ser Ile Asn Ser Phe Asp Asn
        275                 280                 285

Tyr Ile Asn Gln Val Ser Gly Arg Thr Leu Arg Thr Pro Glu Thr Thr
290                 295                 300

Ala Thr Phe Ala Gly Gly Ser Leu Val Leu Ala Asp Gly Gly Asn Leu
305                 310                 315                 320

Ser Leu Lys Ala Pro Ala Gly His Ser Ser Thr Ile Pro Ala Phe Ala
            325                 330                 335

Thr Ser Gly Ser Ile Ser Ile Thr Asn Gly Phe Ser Ser Ile Thr Gln
        340                 345                 350

Pro Leu Val Ile Gly Asp Trp His Leu Gly Ala Gly Thr Ala Gln Val
        355                 360                 365

Ser Val Pro Ser Thr Ser Thr Val Gln Leu Thr Val Asp Lys Leu Ser
        370                 375                 380

Gly Asp Gly Thr Leu Gln Phe Gln Asn Gly Gly Lys Tyr Thr Leu Asn
385                 390                 395                 400

Ile Arg Gly Ala Ser Ala Phe Thr Gly Thr Leu Arg His Leu Ser Gly
                405                 410                 415

Thr Leu Thr Val Ala Ser Gln Ile Gly Thr Gly Gly Thr Leu Val Val
            420                 425                 430

Glu Ser Thr Gly Ala Val Lys Leu Asp His Pro Gly Phe Phe Thr Gly
        435                 440                 445

Val Thr Val Ala Gly Thr Pro Leu Ala Pro Gly Tyr His Thr Tyr Ala
        450                 455                 460

Ala Leu Lys Ala Ala His Pro Ala Arg Phe Pro Thr Gly Ser Thr Asn
465                 470                 475                 480

Ala Phe Leu Ala Val Tyr Pro Pro Asp Thr Thr Gly Pro Ala His Met
                485                 490                 495

Phe Gly Val Asn Leu Ala Gly Gly Glu Phe Gly Thr Pro Met Pro Gly
```

```
                500             505             510
Val Tyr Gly Thr Asp Tyr Ile Tyr Pro Ser Ala Ala Ala Phe Asp Tyr
            515             520             525

Tyr His Gly Lys Gly Leu Lys Leu Ile Arg Leu Pro Phe Lys Trp Glu
            530             535             540

Arg Leu Gln His Thr Leu Asn Ala Pro Leu Asn Ala Ala Glu Leu Ala
545             550             555             560

Arg Ile Asp Thr Val Val Gly Tyr Ala Ser Ala Arg Gly Met Lys Val
            565             570             575

Val Leu Asp Met His Asn Tyr Ala Arg Arg Lys Glu Ser Gly Thr Thr
            580             585             590

Tyr Leu Ile Gly Thr Gly Pro Val Thr Met Asp Ala Phe Gly Asp Val
            595             600             605

Trp Arg Arg Ile Ala Asp His Tyr Lys Gly Asn Pro Ala Ile Tyr Gly
            610             615             620

Tyr Gly Ile Met Asn Glu Pro Tyr Ser Thr Asn Thr Thr Trp Pro Gln
625             630             635             640

Met Ala Gln Thr Ala Val Asn Ala Ile Arg Thr Val Asp Leu Thr Thr
            645             650             655

His Val Ile Val Ala Gly Asp Gly Trp Ser Asn Ala Thr Gly Trp Arg
            660             665             670

Ser Lys Asn Pro Asn Leu Asp Thr Gln Asp Pro Val Gly Arg Leu Ile
            675             680             685

Tyr Glu Ala His Cys Tyr Phe Asp Ser Asn Leu Ser Gly Thr Tyr Thr
            690             695             700

Gln Ser Tyr Asp Ala Ala Gly Ala His Pro Met Ile Gly Val Asp Arg
705             710             715             720

Val Arg Glu Phe Val Glu Trp Leu Gln Glu Thr Gly Asn Lys Gly Phe
            725             730             735

Ile Gly Glu Tyr Gly Val Pro Gly Asn Asp Pro Arg Trp Leu Val Val
            740             745             750

Leu Asp Asn Phe Leu Ala Tyr Leu Asp Ala Asn Gly Val Ser Gly Thr
            755             760             765

Tyr Trp Ala Gly Gly Pro Trp Trp Gly Asn Tyr Pro Leu Ser Cys Glu
            770             775             780

Pro Thr Ser Asn Tyr Thr Val Asp Lys Pro Gln Met Ser Val Leu Glu
785             790             795             800

Asn Tyr Asn

<210> SEQ ID NO 15
<211> LENGTH: 809
<212> TYPE: PRT
<213> ORGANISM: Artificial
<220> FEATURE:
<223> OTHER INFORMATION: HISTAG'ed
<220> FEATURE:
<221> NAME/KEY: MISC_FEATURE
<222> LOCATION: (1)..(9)
<223> OTHER INFORMATION: His tag

<400> SEQUENCE: 15

Met His His His His His Pro Arg Ala Asp Tyr Tyr Leu Lys Val
1               5                   10                  15

Asn Gln Pro His Pro Asn Ser Trp Ala Ser Pro Val Thr Asp Trp Ala
            20              25                  30

Ala Asn Pro Asp Gly Thr Gly Ala Ala Pro Ala Ala Ile Ala Ala Pro
```

-continued

```
             35                  40                  45
Asp Thr Phe Tyr Thr Asn Asn Arg Thr Leu Arg Thr Pro Ala Val Gly
 50                  55                  60

Val Asn Ala Thr Phe Pro Gly Gly Val Leu Gly Leu Asn Gly Gly Val
 65                  70                  75                  80

Ile Gly Ile Lys Thr Gly Pro Ser Ala Phe Ser Ile Ala Pro Lys Leu
                 85                  90                  95

Val Ser Thr Ala Gly Ala Ile Glu Ser Trp Gly Thr Pro Gln Asn Phe
                100                 105                 110

Arg Ala Asp Asp Trp Glu Ser Asn Ala Pro Phe Pro Thr Phe Thr Gly
            115                 120                 125

Leu Arg Thr Ala Ser Asn His Thr Leu Lys Val Ser Val Gly Lys Leu
        130                 135                 140

Ser Gly Thr Gly Glu Ile Arg Val His Gly Gly Thr Val Leu Leu
145                 150                 155                 160

Asp Val Thr Asp Ala Glu Asn Tyr Leu Gly Thr Leu Cys Val Ala Ser
                165                 170                 175

Gly Ala Leu Asn Phe Asp Asn Ala Val Phe Ser Ser Gly Pro Leu Asp
            180                 185                 190

Ile Lys Thr Gly Ala Thr Val Val Leu Asp Gln Ala Val Ser Phe Ala
        195                 200                 205

Gly Leu Ala Val Gly Ala Thr Glu Tyr Pro Pro Gly Asn Tyr Thr Leu
210                 215                 220

Ala Ala Leu Gln Ala Ala His Pro Gly Val Phe Thr Gly Thr Ala Ala
225                 230                 235                 240

Gly Ser Ile Thr Val Arg Ala Pro Arg Thr Trp Tyr Leu Thr Val Ser
                245                 250                 255

Gln Gly Ser Gln Asn Trp Thr Glu Ala Phe Leu Ser Asn Trp Asn Ser
            260                 265                 270

Ala Ala Asn Gly Ser Gly Val Ala Pro Asn Tyr Ile Asn Gly His Asp
        275                 280                 285

Ile Tyr Leu Asn Gln Val Asn Asn Arg Glu Leu Arg Thr Pro Tyr Thr
290                 295                 300

Ala Ser Thr Phe Thr Gly Gly Thr Leu Ala Leu Thr Phe Gly Ser Lys
305                 310                 315                 320

Leu Val Val Lys Thr Ser Pro Asn Leu Val Ser Thr Ile Pro Ala Leu
                325                 330                 335

Val Thr Ser Gly Thr Pro Gln Phe Ala Asn Gly Ser Gly Ser Arg Gln
            340                 345                 350

Asn Leu Ala Ile Gly Asp Trp Asp Ile Ile Ser Gly Thr Ser Arg Leu
        355                 360                 365

Val Ala Gly Ser Thr Arg Ser Leu Gly Phe Asp Ile Gly Trp Leu Thr
370                 375                 380

Gly Ala Gly Asn Leu Gln Thr Glu Gly Gly Ser Phe Phe Leu Arg
385                 390                 395                 400

Leu Ile Asp Gly Ser Gly Tyr Thr Gly Ala Ile Asn His Asn Ser Gly
                405                 410                 415

Ala Leu Arg Phe Glu Ser Val Phe Ser Thr Ala Gly Ala Leu Asn Ile
            420                 425                 430

Gly Ala Ser Ala Thr Val His Leu Asp Lys Pro Val Tyr Val Ser Gly
        435                 440                 445

Leu Ser Val Ala Gly Val Ala Lys Pro Ala Gly Ile His Thr Tyr Ala
450                 455                 460
```

Ser Leu Asn Ala Ala His Pro Ala Gln Phe Asn Ala Gly Ala Ala Pro
465                 470                 475                 480

Gly Leu Val Ala Val Tyr Thr Pro Asn Thr Ala Ala Pro Val Arg Met
            485                 490                 495

Asn Gly Val Asn Leu Ser Gly Pro Glu Ser Val Gly Gly Ala Gly Thr
        500                 505                 510

Pro Phe Pro Gly Thr Tyr Gly Phe Gln Trp Ile Tyr Pro Thr Val Ala
    515                 520                 525

Asp Tyr Asp Tyr Tyr Ala Ala Lys Gly Leu Asn Leu Ile Arg Ile Pro
    530                 535                 540

Phe Arg Trp Glu Arg Met Gln Gly Thr Leu Asn Gly Pro Leu Ile Ala
545                 550                 555                 560

Ala Glu Leu Ala Arg Met Asp Asn Ala Ile Ala Leu Ala Ser Ala Arg
                565                 570                 575

Gly Met Lys Val Ile Leu Asp Met His Asn Tyr Ala Arg Tyr Arg Thr
            580                 585                 590

Pro Thr Ala Ser Tyr Val Phe Gly Asp Ala Gln Leu Pro Ala Ser Ala
        595                 600                 605

Phe Ala Asp Val Trp Arg Lys Leu Ala Asp His Tyr Lys Asn Glu Pro
    610                 615                 620

Ala Ile Tyr Gly Phe Asp Ile Met Asn Glu Pro His Ser Met Pro Thr
625                 630                 635                 640

Pro Thr Thr Trp Pro Thr Tyr Ala Gln Ala Ala Val His Ala Ile Arg
                645                 650                 655

Glu Val Asn Leu Asp Thr Trp Ile Ile Val Glu Gly Glu Thr Tyr Ala
            660                 665                 670

Asn Ser Trp Lys Phe Gly Glu Lys Asn Pro His Leu His Asn Val Arg
        675                 680                 685

Asp Pro Val Gly Arg Leu Met Phe Ser Ala His Ser Tyr Trp Cys Lys
    690                 695                 700

Asn Gly Asp Asp Arg Tyr Gly Thr Tyr Asp Ala Glu Asn Gly His Pro
705                 710                 715                 720

Gln Met Gly Val Asp Ser Leu Lys His Phe Val Asp Trp Leu Arg Lys
                725                 730                 735

His Asn Ala His Gly Phe Val Gly Glu Tyr Gly Val Pro Asn Asn Asp
            740                 745                 750

Pro Arg Trp Leu Glu Val Leu Glu Asn Ala Leu Ile Tyr Leu Ala Asn
        755                 760                 765

Glu Asn Ile Ser Gly Thr Tyr Trp Ala Gly Gly Ala Trp Leu Ala Gly
    770                 775                 780

Ser His Ile Ser Cys His Pro Ser Ser Asn Tyr Thr Val Asp Arg Pro
785                 790                 795                 800

Val Met Ser Val Leu Gln Asn Tyr Pro
                805

<210> SEQ ID NO 16
<211> LENGTH: 802
<212> TYPE: PRT
<213> ORGANISM: Artificial
<220> FEATURE:
<223> OTHER INFORMATION: HISTAG'ed
<220> FEATURE:
<221> NAME/KEY: MISC_FEATURE
<222> LOCATION: (1)..(8)
<220> FEATURE:
<221> NAME/KEY: MISC_FEATURE
<222> LOCATION: (1)..(8)
<223> OTHER INFORMATION: His tag

<400> SEQUENCE: 16

```
His His His His His Pro Arg Ala Asp Trp Tyr Leu Asp Lys Asn
1               5                   10                  15

Gln Ala Arg Tyr Ala Ser Trp Asp Thr Leu Ala Asp Trp Lys Pro Asn
            20                  25                  30

Pro Asp Gly Ser Gly Ser Asn Pro Ser Ala Leu Ser Pro Ser Asp Thr
        35                  40                  45

Tyr His Leu Asn Gly Phe Met Leu Arg Thr Pro Glu Gly Gly Ser Thr
    50                  55                  60

Tyr Thr Phe Thr Gly Gly Leu Leu Ser Leu Ala Asn Asn Ala Asp Asn
65                  70                  75                  80

Phe Ala Leu Lys Thr Thr Gly Ser Gly Val Ser Ile Ile Pro Ala Leu
            85                  90                  95

Arg Thr Thr Ala Gly Leu Val Gln Asn Val Gly Ser Gly Thr Gln Asn
        100                 105                 110

Leu Gln Val Gly His Tyr Gln Asn Leu Ser Gly Thr Thr Ser Tyr Tyr
    115                 120                 125

Ala Gln Thr Gly Arg Gly Leu Asn Leu Ala Ile Thr Thr Leu Val Gly
    130                 135                 140

Ser Gly Gln Phe Arg Phe Tyr Gly Gly Thr Tyr Tyr Leu Ser Leu
145                 150                 155                 160

Ala Asn Ser Pro Thr Tyr Asp Gly Asp Ile Tyr Val Gln Ser Gly Thr
            165                 170                 175

Ile Asp Phe Asn Asn Asp Leu Ala Thr Ala Gly Thr Leu Thr Val Asn
        180                 185                 190

Thr Gly Ala Lys Val Ala Leu Asp Gln Ala Val Thr Phe Thr Gly Leu
    195                 200                 205

Thr Ile Ala Gly Thr Ala Tyr Pro Val Gly Asn Tyr Ser Tyr Ala Ala
    210                 215                 220

Leu Gln Ala Ala His Pro Ala Val Phe Val Ser Gly Thr Ser Gly Gly
225                 230                 235                 240

Ala Ile Asn Val Arg Ala Pro Arg Asn Trp Tyr Leu Ser Thr His Gln
            245                 250                 255

Pro Val Gly Ala Ser Trp Asn Thr Leu Ala His Trp Arg Ala Asn Pro
        260                 265                 270

Asp Gly Thr Gly Ala Thr Ala Asp Ser Ile Asn Ser Phe Asp Asn Tyr
    275                 280                 285

Ile Asn Gln Val Ser Gly Arg Thr Leu Arg Thr Pro Glu Thr Thr Ala
    290                 295                 300

Thr Phe Ala Gly Gly Ser Leu Val Leu Ala Asp Gly Gly Asn Leu Ser
305                 310                 315                 320

Leu Lys Ala Pro Ala Gly His Ser Ser Thr Ile Pro Ala Phe Ala Thr
            325                 330                 335

Ser Gly Ser Ile Ser Ile Thr Asn Gly Phe Ser Ser Ile Thr Gln Pro
        340                 345                 350

Leu Val Ile Gly Asp Trp His Leu Gly Ala Gly Thr Ala Gln Val Ser
    355                 360                 365

Val Pro Ser Thr Ser Thr Val Gln Leu Thr Val Asp Lys Leu Ser Gly
    370                 375                 380

Asp Gly Thr Leu Gln Phe Gln Asn Gly Gly Lys Tyr Thr Leu Asn Ile
385                 390                 395                 400
```

```
Arg Gly Ala Ser Ala Phe Thr Gly Thr Leu Arg His Leu Ser Gly Thr
                    405                 410                 415

Leu Thr Val Ala Ser Gln Ile Gly Thr Gly Thr Leu Val Val Glu
                420                 425                 430

Ser Thr Gly Ala Val Lys Leu Asp His Pro Gly Phe Phe Thr Gly Val
            435                 440                 445

Thr Val Ala Gly Thr Pro Leu Ala Pro Gly Tyr His Thr Tyr Ala Ala
        450                 455                 460

Leu Lys Ala Ala His Pro Ala Arg Phe Pro Thr Gly Ser Thr Asn Ala
465                 470                 475                 480

Phe Leu Ala Val Tyr Pro Pro Asp Thr Thr Gly Pro Ala His Met Phe
                485                 490                 495

Gly Val Asn Leu Ala Gly Gly Glu Phe Gly Thr Pro Met Pro Gly Val
            500                 505                 510

Tyr Gly Thr Asp Tyr Ile Tyr Pro Ser Ala Ala Phe Asp Tyr Tyr
        515                 520                 525

His Gly Lys Gly Leu Lys Leu Ile Arg Leu Pro Phe Lys Trp Glu Arg
        530                 535                 540

Leu Gln His Thr Leu Asn Ala Pro Leu Asn Ala Ala Glu Leu Ala Arg
545                 550                 555                 560

Ile Asp Thr Val Val Gly Tyr Ala Ser Ala Arg Gly Met Lys Val Val
                565                 570                 575

Leu Asp Met His Asn Tyr Ala Arg Arg Lys Glu Ser Gly Thr Thr Tyr
                580                 585                 590

Leu Ile Gly Thr Gly Pro Val Thr Met Asp Ala Phe Gly Asp Val Trp
            595                 600                 605

Arg Arg Ile Ala Asp His Tyr Lys Gly Asn Pro Ala Ile Tyr Gly Tyr
            610                 615                 620

Gly Ile Met Asn Glu Pro Tyr Ser Thr Asn Thr Thr Trp Pro Gln Met
625                 630                 635                 640

Ala Gln Thr Ala Val Asn Ala Ile Arg Thr Val Asp Leu Thr Thr His
                    645                 650                 655

Val Ile Val Ala Gly Asp Gly Trp Ser Asn Ala Thr Gly Trp Arg Ser
                660                 665                 670

Lys Asn Pro Asn Leu Asp Thr Gln Asp Pro Val Gly Arg Leu Ile Tyr
            675                 680                 685

Glu Ala His Cys Tyr Phe Asp Ser Asn Leu Ser Gly Thr Tyr Thr Gln
        690                 695                 700

Ser Tyr Asp Ala Ala Gly Ala His Pro Met Ile Gly Val Asp Arg Val
705                 710                 715                 720

Arg Glu Phe Val Glu Trp Leu Gln Glu Thr Gly Asn Lys Gly Phe Ile
                725                 730                 735

Gly Glu Tyr Gly Val Pro Gly Asn Asp Pro Arg Trp Leu Val Val Leu
            740                 745                 750

Asp Asn Phe Leu Ala Tyr Leu Asp Ala Asn Gly Val Ser Gly Thr Tyr
            755                 760                 765

Trp Ala Gly Gly Pro Trp Trp Gly Asn Tyr Pro Leu Ser Cys Glu Pro
        770                 775                 780

Thr Ser Asn Tyr Thr Val Asp Lys Pro Gln Met Ser Val Leu Glu Asn
785                 790                 795                 800

Tyr Asn
```

```
<210> SEQ ID NO 17
<211> LENGTH: 808
<212> TYPE: PRT
<213> ORGANISM: Artificial
<220> FEATURE:
<223> OTHER INFORMATION: HASTAG'ed
<220> FEATURE:
<221> NAME/KEY: MISC_FEATURE
<222> LOCATION: (1)..(8)
<223> OTHER INFORMATION: Has tag

<400> SEQUENCE: 17
```

His His His His His Pro Arg Ala Asp Tyr Tyr Leu Lys Val Asn
1               5                   10                  15

Gln Pro His Pro Asn Ser Trp Ala Ser Pro Val Thr Asp Trp Ala Ala
            20                  25                  30

Asn Pro Asp Gly Thr Gly Ala Ala Pro Ala Ala Ile Ala Ala Pro Asp
        35                  40                  45

Thr Phe Tyr Thr Asn Asn Arg Thr Leu Arg Thr Pro Ala Val Gly Val
    50                  55                  60

Asn Ala Thr Phe Pro Gly Gly Val Leu Gly Leu Asn Gly Gly Val Ile
65                  70                  75                  80

Gly Ile Lys Thr Gly Pro Ser Ala Phe Ser Ile Ala Pro Lys Leu Val
                85                  90                  95

Ser Thr Ala Gly Ala Ile Glu Ser Trp Gly Thr Pro Gln Asn Phe Arg
            100                 105                 110

Ala Asp Asp Trp Glu Ser Asn Ala Pro Phe Pro Thr Phe Thr Gly Leu
        115                 120                 125

Arg Thr Ala Ser Asn His Thr Leu Lys Val Ser Val Gly Lys Leu Ser
    130                 135                 140

Gly Thr Gly Glu Ile Arg Val His Gly Gly Thr Val Leu Leu Asp
145                 150                 155                 160

Val Thr Asp Ala Glu Asn Tyr Leu Gly Thr Leu Cys Val Ala Ser Gly
                165                 170                 175

Ala Leu Asn Phe Asp Asn Ala Val Phe Ser Ser Gly Pro Leu Asp Ile
            180                 185                 190

Lys Thr Gly Ala Thr Val Val Leu Asp Gln Ala Val Ser Phe Ala Gly
        195                 200                 205

Leu Ala Val Gly Ala Thr Glu Tyr Pro Pro Gly Asn Tyr Thr Leu Ala
    210                 215                 220

Ala Leu Gln Ala Ala His Pro Gly Val Phe Thr Gly Thr Ala Ala Gly
225                 230                 235                 240

Ser Ile Thr Val Arg Ala Pro Arg Thr Trp Tyr Leu Thr Val Ser Gln
                245                 250                 255

Gly Ser Gln Asn Trp Thr Glu Ala Phe Leu Ser Asn Trp Asn Ser Ala
            260                 265                 270

Ala Asn Gly Ser Gly Val Ala Pro Asn Tyr Ile Asn Gly His Asp Ile
        275                 280                 285

Tyr Leu Asn Gln Val Asn Asn Arg Glu Leu Arg Thr Pro Tyr Thr Ala
    290                 295                 300

Ser Thr Phe Thr Gly Gly Thr Leu Ala Leu Thr Phe Gly Ser Lys Leu
305                 310                 315                 320

Val Val Lys Thr Ser Pro Asn Leu Val Ser Thr Ile Pro Ala Leu Val
                325                 330                 335

Thr Ser Gly Thr Pro Gln Phe Ala Asn Gly Ser Gly Ser Arg Gln Asn
            340                 345                 350

-continued

Leu Ala Ile Gly Asp Trp Asp Ile Ser Gly Thr Ser Arg Leu Val
            355                 360                 365
Ala Gly Ser Thr Arg Ser Leu Gly Phe Asp Ile Gly Trp Leu Thr Gly
370                 375                 380
Ala Gly Asn Leu Gln Thr Glu Gly Gly Gly Ser Phe Phe Leu Arg Leu
385                 390                 395                 400
Ile Asp Gly Ser Gly Tyr Thr Gly Ala Ile Asn His Asn Ser Gly Ala
                405                 410                 415
Leu Arg Phe Glu Ser Val Phe Ser Thr Ala Gly Ala Leu Asn Ile Gly
            420                 425                 430
Ala Ser Ala Thr Val His Leu Asp Lys Pro Val Tyr Val Ser Gly Leu
        435                 440                 445
Ser Val Ala Gly Val Ala Lys Pro Ala Gly Ile His Thr Tyr Ala Ser
450                 455                 460
Leu Asn Ala Ala His Pro Ala Gln Phe Asn Ala Gly Ala Ala Pro Gly
465                 470                 475                 480
Leu Val Ala Val Tyr Thr Pro Asn Thr Ala Pro Val Arg Met Asn
                485                 490                 495
Gly Val Asn Leu Ser Gly Pro Glu Ser Val Gly Gly Ala Gly Thr Pro
            500                 505                 510
Phe Pro Gly Thr Tyr Gly Phe Gln Trp Ile Tyr Pro Thr Val Ala Asp
        515                 520                 525
Tyr Asp Tyr Tyr Ala Ala Lys Gly Leu Asn Leu Ile Arg Ile Pro Phe
    530                 535                 540
Arg Trp Glu Arg Met Gln Gly Thr Leu Asn Gly Pro Leu Ile Ala Ala
545                 550                 555                 560
Glu Leu Ala Arg Met Asp Asn Ala Ile Ala Leu Ala Ser Ala Arg Gly
                565                 570                 575
Met Lys Val Ile Leu Asp Met His Asn Tyr Ala Arg Tyr Arg Thr Pro
            580                 585                 590
Thr Ala Ser Tyr Val Phe Gly Asp Ala Gln Leu Pro Ala Ser Ala Phe
        595                 600                 605
Ala Asp Val Trp Arg Lys Leu Ala Asp His Tyr Lys Asn Glu Pro Ala
610                 615                 620
Ile Tyr Gly Phe Asp Ile Met Asn Glu Pro His Ser Met Pro Thr Pro
625                 630                 635                 640
Thr Thr Trp Pro Thr Tyr Ala Gln Ala Ala Val His Ala Ile Arg Glu
                645                 650                 655
Val Asn Leu Asp Thr Trp Ile Ile Val Glu Gly Glu Thr Tyr Ala Asn
            660                 665                 670
Ser Trp Lys Phe Gly Glu Lys Asn Pro His Leu His Asn Val Arg Asp
        675                 680                 685
Pro Val Gly Arg Leu Met Phe Ser Ala His Ser Tyr Trp Cys Lys Asn
    690                 695                 700
Gly Asp Asp Arg Tyr Gly Thr Tyr Asp Ala Glu Asn Gly His Pro Gln
705                 710                 715                 720
Met Gly Val Asp Ser Leu Lys His Phe Val Asp Trp Leu Arg Lys His
                725                 730                 735
Asn Ala His Gly Phe Val Gly Glu Tyr Gly Val Pro Asn Asn Asp Pro
            740                 745                 750
Arg Trp Leu Glu Val Leu Glu Asn Ala Leu Ile Tyr Leu Ala Asn Glu
        755                 760                 765
Asn Ile Ser Gly Thr Tyr Trp Ala Gly Gly Ala Trp Leu Ala Gly Ser

```
                    770                 775                 780
His Ile Ser Cys His Pro Ser Ser Asn Tyr Thr Val Asp Arg Pro Val
785                 790                 795                 800

Met Ser Val Leu Gln Asn Tyr Pro
                805

<210> SEQ ID NO 18
<211> LENGTH: 665
<212> TYPE: PRT
<213> ORGANISM: Artificial
<220> FEATURE:
<223> OTHER INFORMATION: HASTAG'ed
<220> FEATURE:
<221> NAME/KEY: MISC_FEATURE
<222> LOCATION: (1)..(8)
<223> OTHER INFORMATION: Has tag

<400> SEQUENCE: 18

His His His His His Pro Arg Ser Ser Val Ala Ala Val Ser Val
1               5                  10                  15

Ser Ala Lys Ile Asn Ala Phe Thr Asn Ser Asp Trp Leu Asn Gly Ile
                20                  25                  30

Trp Arg Thr Gly Ala Gly Phe Ser Ile Pro Ala Thr Ser Ala Asn Arg
        35                  40                  45

Ala Ala Phe Val Ala Gly Ala Ser Val Arg Leu Ala Asp Gly Gln Val
    50                  55                  60

Arg Lys Ile Ser Arg Ala Gln Ile Val Gly Ser Asn Met Ser Ile Phe
65                  70                  75                  80

Leu Glu Gly Ala Lys Leu Asp Gly Asn Lys Val Gly Ala Pro Gln Val
                85                  90                  95

Val Thr Ile Gly Ser Thr Ala Val Thr Ala Pro Asp Thr Ser Ala Pro
            100                 105                 110

Ile Thr Thr Pro Pro Thr Val Thr Ala His Ser Thr Ser Ile Asn Ala
        115                 120                 125

Phe Thr Asn Asn Asp Trp Leu Asn Gly Val Trp Arg Lys Ser Pro Gly
    130                 135                 140

Phe Ser Ile Pro Ala Ser Ala Ala Asn Lys Ala Ala Phe Lys Val Gly
145                 150                 155                 160

Ala Thr Ala Lys Leu Ala Asp Gly Gln Val Arg Lys Ile Thr Gln Val
                165                 170                 175

Gln Val Val Gly Ala Asn Met Ser Val Tyr Leu Glu Gly Ala Ala Val
            180                 185                 190

Asn Gly Ser Val Val Gly Ala Pro Asn Lys Leu Ala Leu Ala Thr Thr
        195                 200                 205

Ser Thr Thr Ser Pro Ala Pro Thr Pro Ala Pro Ser Ala Pro Thr Pro
    210                 215                 220

Ser Val Ile Ala Thr Ser Asn Leu Asn Asn Tyr Thr Asn Ala Gln Trp
225                 230                 235                 240

Leu Asn Gly Met Tyr Arg Thr Ala Ala Gly Phe Ser Ile Gln Ala Ser
                245                 250                 255

Ser Ala Asn Val Ala Ala Phe Lys Ala Gly Ala Leu Val Arg Leu Ala
            260                 265                 270

Asp Gly Gln Thr Arg Lys Val Leu Arg Ala Gln Leu Val Gly Ser Asn
        275                 280                 285

Met Ser Val Phe Leu Asp Gly Ala Val Ile Asn Gly Thr Thr Leu Gly
    290                 295                 300
```

Tyr Pro Lys Thr Ile Ser Val Val Ser Thr Ser Gly Thr Pro Ser
305                 310                 315                 320

Ser Pro Ala Leu Thr Thr Pro Val Glu Pro Ala Pro Ala Pro Val
                325                 330                 335

Pro Thr Ala Pro Asp Thr Thr Asn Gly Lys Pro Leu Leu Val Gly Val
                340                 345                 350

Asn Leu Ser Gly Ala Gly Phe Gly Pro Ser Val Val Pro Gly Lys His
            355                 360                 365

Gly Thr Asn Tyr Thr Tyr Pro Ala Glu Ser Tyr Tyr Lys Lys Tyr Ser
        370                 375                 380

Asp Leu Gly Met Pro Leu Val Arg Leu Pro Phe Leu Trp Glu Arg Ile
385                 390                 395                 400

Gln Pro Lys Leu Asn Ser Pro Leu Asn Ala Glu Glu Phe Ala Arg Leu
                405                 410                 415

Lys Gln Ser Leu Asp Phe Ala Gln Lys His Asn Val Lys Val Ile Leu
                420                 425                 430

Asp Leu His Asn Tyr Tyr Arg Tyr Tyr Gly Lys Leu Ile Gly Ser Lys
            435                 440                 445

Glu Val Pro Ile Ser Ser Phe Ala Ala Val Trp Lys Gln Ile Val Gln
450                 455                 460

Gln Val Val Asn His Pro Ala Val Glu Gly Tyr Gly Leu Met Asn Glu
465                 470                 475                 480

Pro His Ser Thr Asn Gly Leu Trp Pro Gln Ala Leu Ala Ala Ala
                485                 490                 495

Gln Ala Ile Arg Thr Val Asp Ser Lys Arg Trp Ile Tyr Val Ala Gly
            500                 505                 510

Asp Arg Trp Ser Ser Ala Phe His Trp Pro His Tyr Asn Thr Gln Leu
            515                 520                 525

Val Thr Asn Pro Trp Met Arg Asp Pro Lys Asn Asn Leu Val Tyr Glu
530                 535                 540

Ala His Met Tyr Val Asp Lys Asp Phe Ser Gly Asn Tyr Phe Asp Lys
545                 550                 555                 560

Ala Glu Lys Phe Asp Pro Met Ile Gly Val Asn Arg Val Lys Pro Phe
                565                 570                 575

Val Asp Trp Leu Lys Gln His Lys Leu Arg Gly Tyr Ile Gly Glu His
            580                 585                 590

Gly Val Pro Asp Phe Ser Pro Ser Ala Ile Val Ala Thr Asp Asn Leu
        595                 600                 605

Leu Ala Tyr Leu Arg Gln Asn Cys Ile Pro Ser Thr Tyr Trp Ala Ala
610                 615                 620

Gly Pro Trp Trp Gly Glu Tyr Ala Met Ser Leu Asp Val Ser Ser Gly
625                 630                 635                 640

Lys His Arg Pro Gln Leu Pro Val Leu Gln Lys His Ala Lys Thr Ala
                645                 650                 655

Asn Ser Cys Thr Ser Ile Gly Pro Leu
                660                 665

<210> SEQ ID NO 19
<211> LENGTH: 8
<212> TYPE: PRT
<213> ORGANISM: Artificial
<220> FEATURE:
<223> OTHER INFORMATION: Has tag

<400> SEQUENCE: 19

His His His His His Pro Arg
1               5

<210> SEQ ID NO 20
<211> LENGTH: 27
<212> TYPE: PRT
<213> ORGANISM: Bacillus clausii

<400> SEQUENCE: 20

Met Lys Lys Pro Leu Gly Lys Ile Val Ala Ser Thr Ala Leu Leu Ile
1               5                   10                  15

Ser Val Ala Phe Ser Ser Ser Ile Ala Ser Ala
            20                  25

<210> SEQ ID NO 21
<211> LENGTH: 795
<212> TYPE: PRT
<213> ORGANISM: Paenibacillus sp
<220> FEATURE:
<221> NAME/KEY: mat_peptide
<222> LOCATION: (28)..(795)

<400> SEQUENCE: 21

Met Lys Lys Pro Leu Gly Lys Ile Val Ala Ser Thr Ala Leu Leu Ile
        -25                 -20                 -15

Ser Val Ala Phe Ser Ser Ser Ile Ala Ser Ala His His His His
        -10                 -5                  -1  1               5

His Pro Arg Ala Glu Ala Ser Asp Met Phe Asp Glu Leu Arg Glu Lys
            10                  15                  20

Tyr Ala Thr Met Leu Thr Gly Gly Thr Ala Tyr Ser Leu Ser Asp Pro
            25                  30                  35

Asp Ile Ala Ala Arg Val Ala Ser Ile Thr Thr Asn Ala Gln Thr Leu
            40                  45                  50

Trp Thr Ser Met Lys Lys Asp Ala Asn Arg Val Arg Leu Trp Asp Asn
        55                  60                  65

Ala Pro Leu Gly Asn Asp Ser Ala Ser Ile Thr Thr Ser Tyr Arg Gln
70                  75                  80                  85

Leu Ala Ala Met Ala Leu Ala Tyr Arg Thr Tyr Gly Ser Ser Leu Met
                90                  95                  100

Gly Asp Pro Asp Leu Arg Asp Ile Ile Asp Gly Leu Asp Trp Ile
                105                 110                 115

Asn Thr Phe Gln His Gly Phe Cys Glu Gly Cys Ser Met Tyr Gln Asn
                120                 125                 130

Trp Trp His Trp Gln Ile Gly Gly Pro Ile Ala Leu Asn Glu Val Ile
            135                 140                 145

Ala Leu Met Tyr Asp Glu Leu Thr Gln Thr Gln Ile Asp Ser Tyr Ile
150                 155                 160                 165

Ala Ala Ile Asn Tyr Ala Gln Pro Ser Val Asn Met Thr Gly Ala Asn
                170                 175                 180

Arg Leu Trp Glu Ser Gln Val Ile Ala Leu Ala Gly Ile Asn Gly Lys
            185                 190                 195

Asn Gly Asp Lys Ile Ala His Ala Arg Asp Gly Leu Ser Ala Leu Leu
            200                 205                 210

Thr Tyr Val Val Gln Gly Asp Gly Phe Tyr Glu Asp Gly Ser Phe Val
        215                 220                 225

Gln His Ser Tyr Tyr Ser Tyr Asn Gly Gly Tyr Gly Leu Asp Leu Leu
230                 235                 240                 245

```
Lys Gly Ile Ala Asp Leu Thr Tyr Leu Leu His Asp Ser Asn Trp Glu
            250                 255                 260

Val Val Asp Pro Asn Lys Gln Asn Ile Phe Asn Trp Val Tyr Asp Ser
            265                 270                 275

Phe Glu Pro Phe Ile Tyr Asn Gly Asn Leu Met Asp Met Val Arg Gly
            280                 285                 290

Arg Glu Ile Ser Arg His Ala Arg Gln Ser Asn Val Val Gly Val Glu
            295                 300                 305

Ala Val Ala Ala Ile Leu Arg Leu Ser His Val Ala Pro Pro Ala Asp
310                 315                 320                 325

Ala Ala Ala Phe Lys Ser Met Val Lys His Trp Leu Gln Glu Gly Gly
            330                 335                 340

Gly Ser Gln Phe Leu Gln Gln Ala Ser Ile Thr His Ile Leu Ser Ala
            345                 350                 355

Gln Asp Val Leu Asn Asp Ser Gly Ile Val Pro Arg Gly Glu Leu Glu
            360                 365                 370

Ala Tyr Arg Gln Phe Ala Gly Met Asp Arg Ala Leu Gln Leu Arg Gln
            375                 380                 385

Gly Tyr Gly Phe Gly Ile Ser Met Phe Ser Ser Arg Ile Gly Gly His
390                 395                 400                 405

Glu Ala Ile Asn Ala Glu Asn Asn Lys Gly Trp His Thr Gly Ala Gly
            410                 415                 420

Met Thr Tyr Leu Tyr Asn Asn Asp Leu Ser Gln Phe Asn Asp His Phe
            425                 430                 435

Trp Pro Thr Val Asn Ser Tyr Arg Leu Pro Gly Thr Thr Val Leu Arg
            440                 445                 450

Asp Thr Pro Gln Ala Ala Asn Thr Arg Gly Asp Arg Ser Trp Ala Gly
            455                 460                 465

Gly Thr Asp Met Leu Gly Leu Tyr Gly Ile Thr Gly Met Glu Tyr His
470                 475                 480                 485

Ala Ile Gly Lys Ser Leu Thr Ala Lys Lys Ser Trp Phe Met Phe Asp
            490                 495                 500

Asp Glu Ile Val Ala Leu Gly Ala Asp Ile Thr Ser Gly Asp Gly Val
            505                 510                 515

Ala Val Glu Thr Ile Val Glu Asn Arg Lys Leu Asn Gly Ala Gly Asp
            520                 525                 530

Asn Ser Leu Thr Val Asn Gly Thr Ala Lys Pro Ala Thr Leu Gly Trp
            535                 540                 545

Ser Glu Thr Met Gly Thr Thr Ser Tyr Ala His Leu Gly Gly Ser Val
550                 555                 560                 565

Ala Asp Ser Asp Ile Gly Tyr Tyr Phe Pro Asp Gly Gly Ala Thr Leu
            570                 575                 580

His Ala Leu Arg Glu Ala Arg Thr Gly Asn Trp Arg Gln Ile Asn Ser
            585                 590                 595

Ala Gln Gly Ser Pro Asn Ala Pro His Thr Arg Asn Tyr Leu Thr Met
            600                 605                 610

Trp Leu Glu His Gly Val Asn Pro Ser Asn Gly Ala Tyr Ser Tyr Val
            615                 620                 625

Leu Leu Pro Asn Lys Thr Ser Ala Ala Thr Ala Ser Tyr Ala Ala Ser
630                 635                 640                 645

Pro Asp Ile Thr Ile Glu Asn Ser Ser Ala Gln Ala Val Lys
            650                 655                 660

Glu Asn Gly Leu Asn Met Ile Gly Val Asn Phe Trp Asn Asn Glu Arg
```

```
                    665                 670                 675
Lys Thr Ala Gly Gly Ile Thr Ser Asn Ala Lys Ala Ser Val Met Thr
                680                 685                 690

Arg Glu Thr Ala Ser Glu Leu Asn Val Ser Val Ser Asp Pro Thr Gln
695                 700                 705

Ser Asn Val Gly Met Ile Tyr Ile Glu Ile Asp Lys Ser Ala Thr Gly
710                 715                 720                 725

Leu Ile Ala Lys Asp Asp Ala Val Thr Val Leu Gln Tyr Ser Pro Thr
                730                 735                 740

Ile Lys Phe Lys Val Asp Val Asn Lys Ala Arg Gly Lys Ser Phe Lys
                745                 750                 755

Ala Ala Phe Ser Leu Thr Gly Ala Gln Gln Pro
                760                 765

<210> SEQ ID NO 22
<211> LENGTH: 1073
<212> TYPE: PRT
<213> ORGANISM: Paenibacillus sp
<220> FEATURE:
<221> NAME/KEY: mat_peptide
<222> LOCATION: (28)..(1973)

<400> SEQUENCE: 22

Met Lys Lys Pro Leu Gly Lys Ile Val Ala Ser Thr Ala Leu Leu Ile
        -25                 -20                 -15

Ser Val Ala Phe Ser Ser Ile Ala Ser Ala His His His His
    -10                  -5                 -1   1               5

His Pro Arg Ala Asp Glu Phe Asp Thr Leu Arg Glu Lys Tyr Lys Ala
                10                  15                  20

Met Leu Asn Gly Gly Thr Thr Tyr Asn Leu Ser Asp Pro Asp Ile Ala
            25                  30                  35

Ala Arg Val Asn Ala Ile Thr Val Thr Ala Gln Gly Tyr Trp Asp Ser
        40                  45                  50

Met Leu Lys Asp Pro Asn Arg Asn Arg Leu Trp Asn Asp Ala Pro Phe
55                  60                  65

Gly Ser Asp Ser Thr Ser Ile Thr Thr Thr Tyr Arg His Leu Tyr Asp
70                  75                  80                  85

Met Ala Leu Ala Tyr Thr Thr Tyr Gly Ser Ser Leu Gln Gly Asn Ala
                90                  95                 100

Ala Leu Lys Ala Asp Ile Ile Ser Gly Leu Asp Trp Met Asn Ala Asn
            105                 110                 115

Gln Phe Tyr Asn Gly Cys Ser Gln Tyr Gln Asn Trp Trp His Trp Gln
        120                 125                 130

Ile Gly Gly Pro Met Ala Leu Asn Asp Ile Val Ala Leu Met Tyr Thr
    135                 140                 145

Glu Leu Thr Ala Thr Gln Ile Ser Asn Tyr Met Ala Ile Tyr Tyr
150                 155                 160                 165

Thr Gln Ala Ser Val Thr Met Thr Gly Ala Asn Arg Leu Trp Glu Ser
                170                 175                 180

Gln Val Ile Ala Ile Ser Gly Ile Leu Asn Lys Asp Ser Ala Arg Val
            185                 190                 195

Ala Ala Gly Arg Asp Gly Ile Ser Ala Leu Leu Pro Tyr Val Ala Lys
        200                 205                 210

Gly Asp Gly Phe Tyr Asn Asp Gly Ser Phe Val Gln His Thr Tyr Tyr
    215                 220                 225
```

```
Ala Tyr Asn Gly Gly Tyr Gly Ser Glu Leu Leu Ser Gly Ile Ala Asp
230                 235                 240                 245

Leu Ile Phe Ile Leu Asn Gly Ser Ser Trp Gln Val Thr Asp Pro Asn
        250                 255                 260

Lys Asn Asn Val Tyr Arg Trp Ile Tyr Asp Ser Tyr Glu Pro Phe Ile
            265                 270                 275

Tyr Lys Gly Asn Leu Met Asp Met Val Arg Gly Arg Glu Ile Ser Arg
        280                 285                 290

His Gly Leu Gln Asp Asp Lys Ala Ala Val Thr Val Met Ala Ser Ile
295                 300                 305

Ile Arg Leu Ser Gln Thr Ala Ala Ser Ala Asp Ala Thr Ala Phe Lys
310                 315                 320                 325

Arg Met Val Lys Tyr Trp Leu Leu Leu Asp Thr Asp Lys Thr Phe Leu
            330                 335                 340

Lys Ala Val Ser Ile Asp Leu Ile Ile Ala Ala Asn Gln Leu Val Asn
            345                 350                 355

Asp Ser Thr Val Thr Ser Arg Gly Glu Leu Val Lys Tyr Lys Gln Phe
        360                 365                 370

Ser Gly Met Asp Arg Ala Val Gln Leu Arg Pro Gly Phe Gly Phe Gly
    375                 380                 385

Leu Ser Met Phe Ser Ser Arg Ile Gly Asn Tyr Glu Ser Ile Asn Ala
390                 395                 400                 405

Glu Asn Asn Lys Gly Trp His Thr Gly Asp Gly Met Thr Tyr Leu Tyr
                410                 415                 420

Asn Thr Asp Leu Ser Gln Phe Asn Asp His Phe Trp Ala Thr Val Asp
            425                 430                 435

Asn Tyr Arg Leu Pro Gly Thr Thr Val Leu Gln Asn Thr Thr Gln Thr
        440                 445                 450

Ala Asn Ser Arg Ser Asp Lys Ser Trp Ala Gly Gly Thr Asp Ile Leu
455                 460                 465

Gly Gln Tyr Gly Val Ser Gly Met Glu Leu His Thr Val Gly Lys Ser
470                 475                 480                 485

Leu Thr Ala Lys Lys Ser Trp Phe Met Phe Asp Asp Glu Ile Val Ala
            490                 495                 500

Leu Gly Ser Gly Ile Ala Ser Thr Asp Gly Ile Ala Thr Glu Thr Ile
        505                 510                 515

Val Glu Asn Arg Lys Leu Asn Ser Ser Gly Asn Asn Ala Leu Ile Val
            520                 525                 530

Asn Gly Thr Ala Lys Pro Gly Ser Leu Gly Trp Ser Glu Thr Met Thr
535                 540                 545

Gly Thr Asn Tyr Ile His Leu Ala Gly Ser Val Pro Gly Ser Asp Ile
550                 555                 560                 565

Gly Tyr Tyr Phe Pro Gly Gly Ala Ala Val Lys Gly Leu Arg Glu Ala
            570                 575                 580

Arg Ser Gly Ser Trp Ser Ser Leu Asn Ser Ser Ala Ser Trp Lys Asp
            585                 590                 595

Ser Thr Leu His Thr Arg Asn Phe Met Thr Leu Trp Phe Asp His Gly
        600                 605                 610

Met Asn Pro Thr Asn Gly Ser Tyr Ser Tyr Val Leu Leu Pro Asn Lys
            615                 620                 625

Thr Ser Ser Ala Val Ala Ser Tyr Ala Ala Thr Pro Gln Ile Ser Ile
630                 635                 640                 645

Leu Glu Asn Ser Ser Ser Ala Gln Ala Val Lys Glu Thr Gln Leu Asn
```

```
                650                 655                 660
Val Thr Gly Ile Asn Phe Trp Asn Asp Glu Pro Thr Thr Val Gly Leu
            665                 670                 675
Val Thr Ser Asn Arg Lys Ala Ser Val Met Thr Lys Glu Thr Ala Ser
            680                 685                 690
Asp Phe Glu Ile Ser Val Ser Asp Pro Thr Gln Ser Asn Val Gly Thr
            695                 700                 705
Ile Tyr Ile Asp Val Asn Lys Ser Ala Thr Gly Leu Ile Ser Lys Asp
710                 715                 720                 725
Asn Glu Ile Thr Val Ile Gln Tyr Tyr Pro Thr Met Lys Phe Lys Val
                730                 735                 740
Asn Val Asn Asn Ser Gly Gly Lys Ser Tyr Lys Val Lys Phe Ser Leu
            745                 750                 755
Thr Gly Thr Pro Gly Ser Asn Pro Ser Pro Ile Pro Ile Pro Asn Pro
            760                 765                 770
Tyr Glu Ala Glu Ala Leu Pro Ile Asn Ala Leu Thr Asp Thr Pro Val
            775                 780                 785
Val Tyr Asn Asp Ala Asn Ala Ser Gly Gly Lys Lys Leu Gly Phe Asn
790                 795                 800                 805
Asn Asn Ala Val Asp Asp Tyr Val Glu Phe Ser Leu Asp Val Thr Gln
                810                 815                 820
Pro Gly Thr Tyr Asp Val Lys Ser Arg Ile Met Lys Ser Thr Asn Ser
            825                 830                 835
Gly Ile Tyr Gln Leu Ser Ile Asn Gly Thr Asn Val Gly Ser Ala Gln
            840                 845                 850
Asp Met Phe Trp Thr Thr Ser Glu Leu Ser Lys Glu Phe Thr Met Gly
            855                 860                 865
Ser Tyr Ser Phe Ser Thr Pro Gly Ser Tyr Leu Phe Arg Leu Lys Thr
870                 875                 880                 885
Thr Gly Lys Asn Val Ser Ser Ser Gly Tyr Lys Leu Met Leu Asp Asn
                890                 895                 900
Phe Ser Leu Val Ser Thr Gly Ile Asp Thr Thr Val Ile Val Asp Asn
            905                 910                 915
Ala Asp Ala Ala Gly Val Thr Lys Val Gly Thr Trp Thr Gly Thr Asn
            920                 925                 930
Thr Gln Thr Asp Arg Tyr Gly Ala Asp Tyr Ile His Asp Gly Asn Thr
            935                 940                 945
Gly Lys Gly Thr Lys Ser Val Thr Phe Thr Pro Asn Val Pro Ile Ser
950                 955                 960                 965
Gly Thr Tyr Gln Val Tyr Met Met Trp Ala Ala His Thr Asn Arg Ala
                970                 975                 980
Thr Asn Val Pro Val Asp Val Thr His Ser Gly Gly Thr Ala Thr Leu
            985                 990                 995
Asn Val Asn Gln Gln Gly Asn Gly Gly Val Trp Asn Leu Leu Gly
            1000                1005                1010
Thr Tyr Ser Phe Asn Ala Gly Ser Thr Gly Ala Ile Lys Ile Arg
            1015                1020                1025
Thr Asp Ala Thr Asn Gly Tyr Val Val Ala Asp Ala Val Lys Leu
            1030                1035                1040
Val Lys Val Pro
            1045

<210> SEQ ID NO 23
```

```
<211> LENGTH: 1078
<212> TYPE: PRT
<213> ORGANISM: Paenibacillus sp
<220> FEATURE:
<221> NAME/KEY: mat_peptide
<222> LOCATION: (28)..(1078)

<400> SEQUENCE: 23

Met Lys Lys Pro Leu Gly Lys Ile Val Ala Ser Thr Ala Leu Leu Ile
        -25                 -20                 -15

Ser Val Ala Phe Ser Ser Ile Ala Ser Ala His His His His
        -10                  -5              -1   1                   5

His Pro Arg Ala Glu Ala Ser Asp Met Phe Asp Glu Leu Arg Glu Lys
                     10                  15                  20

Tyr Ala Thr Met Leu Thr Gly Gly Thr Ala Tyr Ser Leu Ser Asp Pro
             25                  30                  35

Asp Ile Ala Ala Arg Val Ala Ser Ile Thr Thr Asn Ala Gln Thr Leu
         40                  45                  50

Trp Thr Ser Met Lys Lys Asp Ala Asn Arg Val Arg Leu Trp Asp Asn
 55                  60                  65

Ala Pro Leu Gly Asn Asp Ser Ala Ser Ile Thr Thr Ser Tyr Arg Gln
 70                  75                  80                  85

Leu Ala Ala Met Ala Leu Ala Tyr Arg Thr Tyr Gly Ser Ser Leu Met
             90                  95                 100

Gly Asp Pro Asp Leu Arg Asp Asp Ile Ile Asp Gly Leu Asp Trp Ile
                 105                 110                 115

Asn Thr Phe Gln His Gly Phe Cys Glu Gly Cys Ser Met Tyr Gln Asn
         120                 125                 130

Trp Trp His Trp Gln Ile Gly Gly Pro Ile Ala Leu Asn Glu Val Ile
135                 140                 145

Ala Leu Met Tyr Asp Glu Leu Thr Gln Thr Gln Ile Asp Ser Tyr Ile
150                 155                 160                 165

Ala Ala Ile Asn Tyr Ala Gln Pro Ser Val Asn Met Thr Gly Ala Asn
                 170                 175                 180

Arg Leu Trp Glu Ser Gln Val Ile Ala Leu Ala Gly Ile Asn Gly Lys
             185                 190                 195

Asn Gly Asp Lys Ile Ala His Ala Arg Asp Gly Leu Ser Ala Leu Leu
         200                 205                 210

Thr Tyr Val Val Gln Gly Asp Gly Phe Tyr Glu Asp Gly Ser Phe Val
     215                 220                 225

Gln His Ser Tyr Tyr Ser Tyr Asn Gly Gly Tyr Gly Leu Asp Leu Leu
230                 235                 240                 245

Lys Gly Ile Ala Asp Leu Thr Tyr Leu Leu His Asp Ser Asn Trp Glu
                 250                 255                 260

Val Val Asp Pro Asn Lys Gln Asn Ile Phe Asn Trp Val Tyr Asp Ser
             265                 270                 275

Phe Glu Pro Phe Ile Tyr Asn Gly Asn Leu Met Asp Met Val Arg Gly
         280                 285                 290

Arg Glu Ile Ser Arg His Ala Arg Gln Ser Asn Val Val Gly Val Glu
     295                 300                 305

Ala Val Ala Ala Ile Leu Arg Leu Ser His Val Ala Pro Pro Ala Asp
310                 315                 320                 325

Ala Ala Ala Phe Lys Ser Met Val Lys His Trp Leu Gln Glu Gly Gly
                 330                 335                 340

Gly Ser Gln Phe Leu Gln Gln Ala Ser Ile Thr His Ile Leu Ser Ala
```

```
            345             350             355
Gln Asp Val Leu Asn Asp Ser Gly Ile Val Pro Arg Gly Glu Leu Glu
            360             365             370
Ala Tyr Arg Gln Phe Ala Gly Met Asp Arg Ala Leu Gln Leu Arg Gln
            375             380             385
Gly Tyr Gly Phe Gly Ile Ser Met Phe Ser Ser Arg Ile Gly Gly His
390             395             400             405
Glu Ala Ile Asn Ala Glu Asn Asn Lys Gly Trp His Thr Gly Ala Gly
            410             415             420
Met Thr Tyr Leu Tyr Asn Asn Asp Leu Ser Gln Phe Asn Asp His Phe
            425             430             435
Trp Pro Thr Val Asn Ser Tyr Arg Leu Pro Gly Thr Val Leu Arg
            440             445             450
Asp Thr Pro Gln Ala Ala Asn Thr Arg Gly Asp Arg Ser Trp Ala Gly
            455             460             465
Gly Thr Asp Met Leu Gly Leu Tyr Gly Ile Thr Gly Met Glu Tyr His
470             475             480             485
Ala Ile Gly Lys Ser Leu Thr Ala Lys Lys Ser Trp Phe Met Phe Asp
            490             495             500
Asp Glu Ile Val Ala Leu Gly Ala Asp Ile Thr Ser Gly Asp Gly Val
            505             510             515
Ala Val Glu Thr Ile Val Glu Asn Arg Lys Leu Asn Gly Ala Gly Asp
            520             525             530
Asn Ser Leu Thr Val Asn Gly Thr Ala Lys Pro Ala Thr Leu Gly Trp
            535             540             545
Ser Glu Thr Met Gly Thr Thr Ser Tyr Ala His Leu Gly Gly Ser Val
550             555             560             565
Ala Asp Ser Asp Ile Gly Tyr Tyr Phe Pro Asp Gly Gly Ala Thr Leu
            570             575             580
His Ala Leu Arg Glu Ala Arg Thr Gly Asn Trp Arg Gln Ile Asn Ser
            585             590             595
Ala Gln Gly Ser Pro Asn Ala Pro His Thr Arg Asn Tyr Leu Thr Met
            600             605             610
Trp Leu Glu His Gly Val Asn Pro Ser Asn Gly Ala Tyr Ser Tyr Val
            615             620             625
Leu Leu Pro Asn Lys Thr Ser Ala Ala Thr Ala Ser Tyr Ala Ala Ser
630             635             640             645
Pro Asp Ile Thr Ile Glu Asn Ser Ser Ala Gln Ala Val Lys
            650             655             660
Glu Asn Gly Leu Asn Met Ile Gly Val Asn Phe Trp Asn Asn Glu Arg
            665             670             675
Lys Thr Ala Gly Gly Ile Thr Ser Asn Ala Lys Ala Ser Val Met Thr
            680             685             690
Arg Glu Thr Ala Ser Glu Leu Asn Val Ser Val Ser Asp Pro Thr Gln
            695             700             705
Ser Asn Val Gly Met Ile Tyr Ile Glu Ile Asp Lys Ser Ala Thr Gly
710             715             720             725
Leu Ile Ala Lys Asp Asp Ala Val Thr Val Leu Gln Tyr Ser Pro Thr
            730             735             740
Ile Lys Phe Lys Val Asp Val Asn Lys Ala Arg Gly Lys Ser Phe Lys
            745             750             755
Ala Ala Phe Ser Leu Thr Gly Ala Gln Gln Pro Asn Pro Ala Pro Ile
            760             765             770
```

```
Pro Ile Pro Asn Pro Tyr Glu Ala Glu Leu Pro Ile Ser Ala Thr
    775                 780                 785

Thr Lys Thr Pro Thr Leu Ser Asn Asp Ser Asn Ala Ser Gly Gly Lys
790                 795                 800                 805

Lys Leu Gly Leu Asn Ser Ser Val Val Gly Asp Tyr Thr Glu Phe Ser
            810                 815                 820

Leu Asp Val Thr Gln Pro Gly Thr Tyr Asp Ile Ala Ala Lys Ile Met
                825                 830                 835

Lys Val Ser Asn Asn Gly Ile Tyr Gln Phe Ser Ile Asn Gly Glu Pro
            840                 845                 850

Val Gly Asp Pro Val Asp Met Tyr Trp Asn Thr Ser Glu Ser Thr Lys
    855                 860                 865

Ser Phe Ser Pro Gly Ser Tyr Thr Phe Ser Glu Pro Gly Ser Tyr Leu
870                 875                 880                 885

Leu Arg Val Thr Val Thr Gly Lys His Pro Ser Ser Gly Tyr Lys
                890                 895                 900

Leu Met Leu Asp His Phe Thr Leu Glu Glu Ile Pro Val Ser Leu Pro
            905                 910                 915

Asn Pro Tyr Glu Ala Glu Thr Leu Pro Ile His Arg Thr Gln Thr
    920                 925                 930

Val Thr Ile Tyr Asn Asp Ser Asn Thr Ser Gly Gly Gln Arg Leu Gly
935                 940                 945

Leu Asn His Lys Val Val Gly Asp Tyr Thr Glu Phe Ile Leu Asp Val
950                 955                 960                 965

Pro Gln Ala Gly Thr Tyr Asp Ile Thr Ala Arg Val Leu Lys Phe Ser
            970                 975                 980

Asp Asn Gly Ile Tyr Gln Phe Ser Ile Asp Gly Asn Pro Val Gly Ala
            985                 990                 995

Pro Ile Asp Thr Tyr Trp Asn Thr Ala Gly Tyr Ile Arg Asp Phe
    1000                1005                1010

Thr Pro Gly Ser Tyr Thr Phe Ser Glu Pro Gly Ser Tyr Leu Leu
    1015                1020                1025

Arg Leu Thr Ala Thr Gly Lys Asn Pro Ser Ala Ser Gly Leu Lys
    1030                1035                1040

Ile Met Leu Asp Tyr Ile Trp Leu Asp
    1045                1050
```

<210> SEQ ID NO 24
<211> LENGTH: 968
<212> TYPE: PRT
<213> ORGANISM: Paenibacillus sp
<220> FEATURE:
<221> NAME/KEY: mat_peptide
<222> LOCATION: (28)..(968)

<400> SEQUENCE: 24

```
Met Lys Lys Pro Leu Gly Lys Ile Val Ala Ser Thr Ala Leu Leu Ile
        -25                 -20                 -15

Ser Val Ala Phe Ser Ser Ser Ile Ala Ser Ala His His His His
        -10                 -5              -1  1               5

His Pro Arg Gly Gly Glu Ala Ser Gly Ser Ala Asp Asp Ala Ala Glu
                10                  15                  20

Thr Ala Glu Ala Ala Glu Gly Glu Asn Ile Glu Asp Lys Met Val Ser
            25                  30                  35

Ala Tyr Asn Met Asp Ala Phe Asp Ile Met Arg Glu Val Arg Arg Thr
```

```
                40                  45                  50
    Met Leu Thr Gly Gly Ala Ala Leu Asn Pro Ala Asp Pro Ala Ala
    55                  60                  65

Ala Ala Val Ala Ala Leu Ala Ser Glu Ala Asn Gln Tyr Trp Gln Thr
    70                  75                  80                  85

Met Asp Asp Ser Pro Gly Arg Thr Ser Leu Trp Ser Asp Asn Pro Gly
                        90                  95                  100

Thr Gly Asn Ser Ile His Ile Arg Ile Thr Tyr Glu Arg Leu Lys Thr
                    105                 110                 115

Met Ala Leu Ala Tyr Ala Ala Gly Ser Pro Leu His Ser Asn Ala
                    120                 125                 130

Ser Leu Glu Ala Asp Ile Val Asp Ala Leu Asp Tyr Met Tyr Ala Thr
        135                 140                 145

Arg Tyr His Glu Asn Val Thr Thr Pro Ser Gly Thr Ser Asn Trp
    150                 155                 160                 165

Trp Asp Trp Gln Ile Gly Ile Pro Met Gln Leu Asn Asp Thr Val Val
                    170                 175                 180

Leu Met Tyr Asp Ser Leu Thr Pro Ala Gln Ile Ala Asn Tyr Met Asn
                    185                 190                 195

Ala Val Glu Arg Phe Thr Pro Thr Val Asn Leu Thr Gly Ala Asn Arg
                200                 205                 210

Ser Trp Lys Ala Ile Val Val Ala Val Arg Gly Ile Leu Val Lys Asp
        215                 220                 225

Gly Ala Lys Ile Ala Ala Ala Arg Asp Gly Leu Ser Gln Ile Phe Asn
    230                 235                 240                 245

Tyr Ala Val Ser Gly Asp Gly Phe Tyr Arg Asp Gly Ser Phe Ile Gln
                    250                 255                 260

His Gly Asn Ile Pro Tyr Asn Gly Gly Tyr Gly Leu Asp Leu Leu Leu
                    265                 270                 275

Ala Val Ser Asp Leu Met Thr Leu Leu His Gly Ser Ala Trp Gln Val
                280                 285                 290

Thr Asp Pro Asn Gln Ala Asn Val Trp Glu Trp Val Tyr Arg Ala Tyr
        295                 300                 305

Gln Pro Leu Ile Tyr Lys Gly Ala Met Met Asp Met Val Arg Gly Arg
    310                 315                 320                 325

Glu Ile Ser Arg Val Tyr Arg Gln Asp His Ala Ala Gly His Ile Ala
                    330                 335                 340

Met Gln Gly Ile Leu Arg Leu Ser Ala Val Ala Pro Ala Gln Ala
                    345                 350                 355

Glu Asp Phe Lys Arg Met Val Lys Gly Trp Met Val Val Asp Gly Phe
                360                 365                 370

Met Arg Phe Tyr Glu Gln Ala Pro Leu Gly Leu Ile Pro Leu Ala Lys
        375                 380                 385

Ala Val Glu Gly Asp Ala Ser Ile Ala Pro Ala Ser Glu Leu Ile Gln
    390                 395                 400                 405

Tyr Arg Gln Tyr Ala Ala Met Asp Arg Ala Val Gln Leu Arg Pro Gly
                    410                 415                 420

Tyr Gly Phe Gly Leu Ala Met Tyr Ser Ser Arg Ile Gly Ser Phe Glu
                    425                 430                 435

Ala Ile Asn Ser Glu Asn Leu Arg Gly Trp Tyr Thr Ser Ala Gly Met
                440                 445                 450

Thr Ser Leu Tyr Asn Gly Asp Leu Gly His Tyr Ser Glu Asp Tyr Trp
        455                 460                 465
```

```
Pro Thr Val Asn Ala Tyr Arg Leu Pro Gly Thr Thr Val Leu Ser Gly
470                 475                 480                 485

Thr Ala Ala Ala Ser His Thr Ser Pro Asn Asn Trp Thr Gly Gly Thr
                490                 495                 500

Asp Met Gln Gly Leu Tyr Gly Val Ser Gly Met Asp Leu Lys Tyr Ala
            505                 510                 515

Ser Asn Ser Leu Ala Ala Arg Lys Ser Trp Phe Met Phe Asp Asp Glu
            520                 525                 530

Ile Val Ala Leu Gly Ala Gly Ile Ser Ser Ala Asp Gly Ile Pro Val
    535                 540                 545

Glu Thr Ile Ile Glu Asn Arg Arg Ile Gly Gly Ala Gly Asp Asn Ala
550                 555                 560                 565

Phe Leu Ala Asp Gly Ala Ala Met Pro Ala Glu Leu Gly Trp Ser Gly
                570                 575                 580

Thr Leu Glu Gly Val Arg Trp Ala His Leu Thr Gly Thr Ala Ala Gly
            585                 590                 595

Ala Asp Ile Gly Tyr Tyr Phe Pro Glu Pro Ala Ala Val His Ala Val
                600                 605                 610

Arg Glu Ala Arg Thr Gly Asn Trp Arg Gln Ile Asn Asn Arg Pro Val
615                 620                 625

Thr Pro Ala Ala Ser Val Thr Arg Asn Tyr Leu Thr Phe Trp Phe Asp
630                 635                 640                 645

His Gly Ala Asn Pro Thr Asn Ala Asp Tyr Gln Tyr Val Leu Leu Pro
                650                 655                 660

Asn Lys Ser Gly Ala Gln Val Ala Gly Tyr Ala Ala Asn Pro Asp Val
            665                 670                 675

Glu Val Leu Ala Asn Ser Pro Glu Val Gln Ala Val Lys Glu Ser Ser
            680                 685                 690

Leu Gly Ile Ile Gly Ala Asn Phe Trp Ser Asp Gly Val Arg Thr Val
    695                 700                 705

Asp Leu Ile Thr Val Asn Lys Lys Ala Ser Val Met Thr Arg Glu Thr
710                 715                 720                 725

Pro Gly Ala Ile Leu Asp Leu Ser Val Ser Asp Pro Thr Gln Val Asn
                730                 735                 740

Ala Gly Thr Ile Glu Ile Glu Leu Asn Arg Ala Ala Ser Gly Phe Thr
            745                 750                 755

Ala Asp Pro Gly Val Thr Val Thr Arg Leu Ser Pro Thr Ile Lys Leu
            760                 765                 770

Thr Val Gln Val Ala Gly Ala Lys Gly Arg Ser Phe Lys Ala Ser Phe
    775                 780                 785

Glu Leu Gly Glu Ala Ser Gly Pro Gly Pro Asp Pro Gly Pro Gly Pro
790                 795                 800                 805

Ser Glu Ile Ile Val Asp Asn Gly Asp Ala Ala Gly Val Thr Lys Ile
                810                 815                 820

Gly Ser Trp Lys Thr Gly Thr Val Gln Thr Asp Arg Tyr Gly Pro Asp
            825                 830                 835

Tyr Leu His Asp Asp Asn Thr Gly Lys Gly Lys Ser Val Arg Phe
            840                 845                 850

Thr Pro Asp Leu Pro Thr Ala Gly Thr Tyr Asp Val Tyr Met Met Trp
855                 860                 865

Pro Gln His Phe Asn Arg Ala Thr Asn Ile Pro Val Thr Ile Ala His
870                 875                 880                 885
```

```
Ala Gly Gly Thr Ala Thr Val Thr Ile Asp Gln Thr Val Ser Gly Gly
                890                 895                 900

Val Trp Asn Tyr Leu Gly Ser Tyr Ser Phe Asp Thr Ser Gly Gly
    905                 910                 915

Ser Val Thr Ile Ser Asn Ala Gly Thr Asn Gly Tyr Val Val Ala Asp
        920                 925                 930

Ala Val Lys Phe Glu Tyr Val Pro
    935                 940

<210> SEQ ID NO 25
<211> LENGTH: 1074
<212> TYPE: PRT
<213> ORGANISM: Artificial
<220> FEATURE:
<223> OTHER INFORMATION: Artificially Synthesized

<400> SEQUENCE: 25

Met Leu Lys Gln Gly Met Lys Arg Trp Thr Ser Val Cys Leu Ala Ile
1               5                   10                  15

Ile Met Phe Ser Leu Thr Phe Leu Asn Ala Gly Thr Val Pro Arg Ala
            20                  25                  30

Glu Ala Ser Asp Met Phe Asp Glu Leu Arg Glu Lys Tyr Ala Thr Met
        35                  40                  45

Leu Thr Gly Gly Thr Ala Tyr Ser Leu Ser Asp Pro Asp Ile Ala Ala
    50                  55                  60

Arg Val Ala Ser Ile Thr Thr Asn Ala Gln Thr Leu Trp Thr Ser Met
65                  70                  75                  80

Lys Lys Asp Ala Asn Arg Val Arg Leu Trp Asp Asn Ala Pro Leu Gly
                85                  90                  95

Asn Asp Ser Ala Ser Ile Thr Thr Ser Tyr Arg Gln Leu Ala Ala Met
            100                 105                 110

Ala Leu Ala Tyr Arg Thr Tyr Gly Ser Ser Leu Met Gly Asp Pro Asp
        115                 120                 125

Leu Arg Asp Asp Ile Ile Asp Gly Leu Asp Trp Ile Asn Thr Phe Gln
    130                 135                 140

His Gly Phe Cys Glu Gly Cys Ser Met Tyr Gln Asn Trp Trp His Trp
145                 150                 155                 160

Gln Ile Gly Gly Pro Ile Ala Leu Asn Glu Val Ile Ala Leu Met Tyr
                165                 170                 175

Asp Glu Leu Thr Gln Thr Gln Ile Asp Ser Tyr Ile Ala Ala Ile Asn
            180                 185                 190

Tyr Ala Gln Pro Ser Val Asn Met Thr Gly Ala Asn Arg Leu Trp Glu
        195                 200                 205

Ser Gln Val Ile Ala Leu Ala Gly Ile Asn Gly Lys Asn Gly Asp Lys
    210                 215                 220

Ile Ala His Ala Arg Asp Gly Leu Ser Ala Leu Leu Thr Tyr Val Val
225                 230                 235                 240

Gln Gly Asp Gly Phe Tyr Glu Asp Gly Ser Phe Val Gln His Ser Tyr
                245                 250                 255

Tyr Ser Tyr Asn Gly Gly Tyr Gly Leu Asp Leu Leu Lys Gly Ile Ala
            260                 265                 270

Asp Leu Thr Tyr Leu Leu His Asp Ser Asn Trp Glu Val Val Asp Pro
        275                 280                 285

Asn Lys Gln Asn Ile Phe Asn Trp Val Tyr Asp Ser Phe Glu Pro Phe
    290                 295                 300
```

-continued

```
Ile Tyr Asn Gly Asn Leu Met Asp Met Val Arg Gly Arg Glu Ile Ser
305                 310                 315                 320

Arg His Ala Arg Gln Ser Asn Val Val Gly Val Glu Ala Val Ala Ala
                325                 330                 335

Ile Leu Arg Leu Ser His Val Ala Pro Pro Ala Asp Ala Ala Ala Phe
            340                 345                 350

Lys Ser Met Val Lys His Trp Leu Gln Glu Gly Gly Ser Gln Phe
        355                 360                 365

Leu Gln Gln Ala Ser Ile Thr His Ile Leu Ser Ala Gln Asp Val Leu
    370                 375                 380

Asn Asp Ser Gly Ile Val Pro Arg Gly Glu Leu Glu Ala Tyr Arg Gln
385                 390                 395                 400

Phe Ala Gly Met Asp Arg Ala Leu Gln Leu Arg Gln Gly Tyr Gly Phe
                405                 410                 415

Gly Ile Ser Met Phe Ser Ser Arg Ile Gly Gly His Glu Ala Ile Asn
            420                 425                 430

Ala Glu Asn Asn Lys Gly Trp His Thr Gly Ala Gly Met Thr Tyr Leu
        435                 440                 445

Tyr Asn Asn Asp Leu Ser Gln Phe Asn Asp His Phe Trp Pro Thr Val
    450                 455                 460

Asn Ser Tyr Arg Leu Pro Gly Thr Thr Val Leu Arg Asp Thr Pro Gln
465                 470                 475                 480

Ala Ala Asn Thr Arg Gly Asp Arg Ser Trp Ala Gly Thr Asp Met
                485                 490                 495

Leu Gly Leu Tyr Gly Ile Thr Gly Met Glu Tyr His Ala Ile Gly Lys
            500                 505                 510

Ser Leu Thr Ala Lys Lys Ser Trp Phe Met Phe Asp Asp Glu Ile Val
        515                 520                 525

Ala Leu Gly Ala Asp Ile Thr Ser Gly Asp Gly Val Ala Val Glu Thr
    530                 535                 540

Ile Val Glu Asn Arg Lys Leu Asn Gly Ala Gly Asp Asn Ser Leu Thr
545                 550                 555                 560

Val Asn Gly Thr Ala Lys Pro Ala Thr Leu Gly Trp Ser Glu Thr Met
                565                 570                 575

Gly Thr Thr Ser Tyr Ala His Leu Gly Gly Ser Val Ala Asp Ser Asp
            580                 585                 590

Ile Gly Tyr Tyr Phe Pro Asp Gly Gly Ala Thr Leu His Ala Leu Arg
        595                 600                 605

Glu Ala Arg Thr Gly Asn Trp Arg Gln Ile Asn Ser Ala Gln Gly Ser
    610                 615                 620

Pro Asn Ala Pro His Thr Arg Asn Tyr Leu Thr Met Trp Leu Glu His
625                 630                 635                 640

Gly Val Asn Pro Ser Asn Gly Ala Tyr Ser Tyr Val Leu Leu Pro Asn
                645                 650                 655

Lys Thr Ser Ala Ala Thr Ala Ser Tyr Ala Ala Ser Pro Asp Ile Thr
            660                 665                 670

Ile Ile Glu Asn Ser Ser Ala Gln Ala Val Lys Glu Asn Gly Leu
        675                 680                 685

Asn Met Ile Gly Val Asn Phe Trp Asn Asn Glu Arg Lys Thr Ala Gly
    690                 695                 700

Gly Ile Thr Ser Asn Ala Lys Ala Ser Val Met Thr Arg Glu Thr Ala
705                 710                 715                 720

Ser Glu Leu Asn Val Ser Val Ser Asp Pro Thr Gln Ser Asn Val Gly
```

```
                     725                 730                 735
Met Ile Tyr Ile Glu Ile Asp Lys Ser Ala Thr Gly Leu Ile Ala Lys
                 740                 745                 750

Asp Asp Ala Val Thr Val Leu Gln Tyr Ser Pro Thr Ile Lys Phe Lys
                 755                 760                 765

Val Asp Val Asn Lys Ala Arg Gly Lys Ser Phe Lys Ala Ala Phe Ser
    770                 775                 780

Leu Thr Gly Ala Gln Gln Pro Asn Pro Ala Pro Ile Pro Ile Pro Asn
785                 790                 795                 800

Pro Tyr Glu Ala Glu Leu Leu Pro Ile Ser Ala Thr Lys Thr Pro
                805                 810                 815

Thr Leu Ser Asn Asp Ser Asn Ala Ser Gly Lys Lys Leu Gly Leu
                820                 825                 830

Asn Ser Ser Val Val Gly Asp Tyr Thr Glu Phe Ser Leu Asp Val Thr
                835                 840                 845

Gln Pro Gly Thr Tyr Asp Ile Ala Ala Lys Ile Met Lys Val Ser Asn
850                 855                 860

Asn Gly Ile Tyr Gln Phe Ser Ile Asn Gly Glu Pro Val Gly Asp Pro
865                 870                 875                 880

Val Asp Met Tyr Trp Asn Thr Ser Glu Ser Thr Lys Ser Phe Ser Pro
                885                 890                 895

Gly Ser Tyr Thr Phe Ser Glu Pro Gly Ser Tyr Leu Leu Arg Val Thr
                900                 905                 910

Val Thr Gly Lys His Pro Ser Ser Gly Tyr Lys Leu Met Leu Asp
                915                 920                 925

His Phe Thr Leu Glu Glu Ile Pro Val Ser Leu Pro Asn Pro Tyr Glu
930                 935                 940

Ala Glu Thr Leu Pro Ile His His Arg Thr Gln Thr Val Thr Ile Tyr
945                 950                 955                 960

Asn Asp Ser Asn Thr Ser Gly Gly Gln Arg Leu Gly Leu Asn His Lys
                965                 970                 975

Val Val Gly Asp Tyr Thr Glu Phe Ile Leu Asp Val Pro Gln Ala Gly
                980                 985                 990

Thr Tyr Asp Ile Thr Ala Arg Val Leu Lys Phe Ser Asp Asn Gly Ile
                995                 1000                1005

Tyr Gln Phe Ser Ile Asp Gly Asn Pro Val Gly Ala Pro Ile Asp
    1010                1015                1020

Thr Tyr Trp Asn Thr Ala Gly Tyr Ile Arg Asp Phe Thr Pro Gly
    1025                1030                1035

Ser Tyr Thr Phe Ser Glu Pro Gly Ser Tyr Leu Leu Arg Leu Thr
    1040                1045                1050

Ala Thr Gly Lys Asn Pro Ser Ala Ser Gly Leu Lys Ile Met Leu
    1055                1060                1065

Asp Tyr Ile Trp Leu Asp
    1070
```

DETERGENT COMPOSITIONS COMPRISING POLYPEPTIDES HAVING XANTHAN DEGRADING ACTIVITY

CROSS-REFERENCE TO RELATED APPLICATION

This application is a U.S. National-Stage entry under 35 U.S.C. § 371 based on International Application No. PCT/EP2016/071801, filed Sep. 15, 2016 which was published under PCT Article 2 1(2) and which claims priority to European Application No. 15185640.8, filed Sep. 17, 2015, which are all hereby incorporated in their entirety by reference.

REFERENCE TO A JOINT RESEARCH AGREEMENT

The embodiments claimed in the present application were made under a joint research agreement between Henkel AG & Co. KGaA and Novozymes A/S.

REFERENCE TO A SEQUENCE LISTING

This application contains a Sequence Listing in computer readable form, which is incorporated herein by reference.

TECHNICAL FIELD

The present disclosure relates to detergent compositions comprising polypeptides having xanthan degrading activity. In particular the disclosure relates to such detergent compositions comprising polypeptides within the glycosyl hydrolase family 5 (GH5) having xanthan degrading activity. The disclosure also relates to methods for producing said detergent compositions and to the use of said detergent compositions in cleaning applications.

BACKGROUND

Xanthan gum is a polysaccharide secreted by the bacterium *Xanthomonas campestris*. It is produced by the fermentation of glucose, sucrose, or lactose in an aqueous growth medium by *X. campestris*. After a fermentation period, the polysaccharide is precipitated from the growth medium with isopropyl alcohol, dried, and ground into a fine powder. Later, the powder is added to a liquid medium to form the gum.

Xanthan is composed of pentasaccharide subunits, forming a cellulose backbone with trisaccharide side chains composed of mannose-(beta1,4)-glucuronic-acid-(beta1,2)-mannose attached to alternate glucose residues in the backbone by alpha1,3 linkages. This biopolymer is of great commercial significance because of its superior pseudoplasticity, thixotropy, and viscosity.

In recent years xanthan gum has been widely used as an ingredient in many consumer products including foods (e.g., as thickening agent in salad dressings and dairy products) and cosmetics (e.g., as stabilizer and thickener in toothpaste and make-up to prevent ingredients from separating) and cosmetics (e.g., sun creams).

In addition, xanthan gum has found use in the oil industry where xanthan gum is used in large quantities to thicken drilling mud. These fluids serve to carry the solids cut by the drilling bit back to the surface. When the circulation stops, the solids still remain suspended in the drilling fluid. The widespread use of horizontal drilling has led to its expanded use. Xanthan gum is also added to self-consolidating concrete, including concrete poured underwater, to increase its viscosity.

The widespread use of xanthan gum has led to a desire to be able to degrade solutions or gels of xanthan gum. Complete enzymatic degradation of xanthan gum has till now required several enzymatic activities including xanthan lyase activity and endo-beta-1,4-glucanase activity. Xanthan lyases are enzymes that cleave the beta-D-mannosylalpha-beta-D-1,4-glucuronosyl bond of xanthan and have been described in the literature. Xanthan degrading enzymes are known in the art e.g., two xanthan lyases isolated from *Paenibacillus alginolyticus* XL-1.

Glycosyl hydrolases are enzymes that catalyze the hydrolysis of the glycosyl bond to release smaller sugars. There are over 100 classes of Glycosyl hydrolases which have been classified. The glycosyl hydrolase family 5 (GH5) includes endo-glucanases (EC 3.2.1.4), endo-beta-1,4-xylanase (EC 3.2.1.8); beta-glucosidase (EC 3.2.1.21); beta-mannosidase (EC 3.2.1.25). However, until now identification of xanthan degrading enzymes have not been reported in glycosyl hydrolase family 5.

The mature peptide in SEQ ID NO: 2 is 45% identical and the mature peptide in SEQ ID NO: 4 is 57% identical to a predicted endoglucanase from the genome of *Echinicola vietnamensis* (UNIPROT: L0FVA9).

The mature peptide in SEQ ID NO: 6 is 47% identical to an uncharacterized protein from the genome of *Barnesiella intestinihominis* (UNIPROT: K0WXE1).

The mature peptide in SEQ ID NO: 8 is 100% identical to an uncharacterized protein from the genome of *Pseudomonas stutzeri* (UNIPROT: M2V1S3).

BRIEF SUMMARY

A detergent composition is provided herein. The detergent composition includes a polypeptide of glycosyl hydrolase family 5 having xanthan degrading activity.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The disclosure provides new and improved detergent compositions comprising enzymes for the degradation of xanthan gum and methods for producing said detergent compositions and to the use of said detergent compositions in cleaning applications.

The present inventors have surprisingly discovered a new group of enzymes that have xanthan degrading activity—and which do not belong to any glycosyl hydrolase family previously known to comprise this enzymatic activity. The enzymes have no significant sequence similarity to any known enzyme having xanthan degrading activity.

The present disclosure provides detergent compositions comprising polypeptides having xanthan degrading activity, i.e., having activity on xanthan gum and/or having activity on xanthan gum pretreated with xanthan lyase.

Accordingly, the present disclosure provides a detergent composition comprising polypeptide of glycosyl hydrolase family 5 having xanthan degrading activity. More particularly, the present disclosure provides a detergent composition comprising polypeptide of glycosyl hydrolase family 5 having xanthan degrading activity, selected from the group consisting of:

(a) a polypeptide having at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100% sequence identity to the mature polypeptide of any of SEQ ID NO: 2, SEQ ID NO: 4, SEQ ID NO: 6 or SEQ ID NO: 8;

(b) a polypeptide encoded by a polynucleotide that hybridizes under medium stringency conditions with (i) the mature polypeptide coding sequence of any of SEQ ID NO: 1, SEQ ID NO: 3, SEQ ID NO: 5 or SEQ ID NO: 7, (ii), or the full-length complement of (i);

(c) a polypeptide encoded by a polynucleotide having at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100% sequence identity to the mature polypeptide coding sequence of any of SEQ ID NO: 1, SEQ ID NO: 3, SEQ ID NO: 5 or SEQ ID NO: 7;

(d) a variant of the mature polypeptide of any of SEQ ID NO: 2 SEQ ID NO: 4, SEQ ID NO: 6 or SEQ ID NO: 8 comprising a substitution, deletion, and/or insertion at one or more positions;

(e) a fragment of the polypeptide of (a), (b), (c), or (d) that has xanthan degrading activity; and (f) a polypeptide comprising the polypeptide of (a), (b), (c), (d), or (e) and a N-terminal and/or C-terminal His-tag.

The present disclosure also relates to methods of degrading xanthan gum using the detergent composition comprising the polypeptides.

Overview of Sequence Listing

SEQ ID NO: 1 is the DNA sequence of the EXa gene as isolated from an *Opitutaceae* sp.
SEQ ID NO: 2 is the amino acid sequence of the EXa GH5 polypeptide as deduced from SEQ ID NO: 1.
SEQ ID NO: 3 is the DNA sequence of the EXb gene as isolated from an environmental sample
SEQ ID NO: 4 is the amino acid sequence of the EXb GH5 polypeptide as deduced from SEQ ID NO: 3.
SEQ ID NO: 5 is the DNA sequence of the EXc gene as isolated from an environmental sample
SEQ ID NO: 6 is the amino acid sequence of the EXc GH5 polypeptide as deduced from SEQ ID NO: 5.
SEQ ID NO: 7 is the DNA sequence of the EXd gene as obtained from a public database (UNIPROT M2V1S3, originating from a strain of *Pseudomonas stutzeri* collected from a Galapagos Rift hydrothermal vent, Ecuador).
SEQ ID NO: 8 is the amino acid sequence of the EXd GH5 polypeptide as deduced from SEQ ID NO: 7.
SEQ ID NO: 9 is synth codon optimized DNA encoding the EXa GH5 polypeptide.
SEQ ID NO: 10 is synth codon optimized DNA encoding the EXb GH5 polypeptide.
SEQ ID NO: 11 is synth codon optimized DNA encoding the EXc GH5 polypeptide.
SEQ ID NO: 12 is synth codon optimized DNA encoding the EXd GH5 polypeptide.
SEQ ID NO: 13 is the EXa GH5 polypeptide+His affinity tag expressed in *E. coli*.
SEQ ID NO: 14 is the EXb GH5 polypeptide+His affinity tag expressed in *E. coli*.
SEQ ID NO: 15 the EXc GH5 polypeptide+His affinity tag expressed in *E. coli*.
SEQ ID NO: 16 is the EXb GH5 polypeptide+His affinity tag expressed in *B. subtilis*.
SEQ ID NO: 17 is the EXc GH5 polypeptide+His affinity tag expressed in *B. subtilis*.
SEQ ID NO: 18 is the EXd GH5 polypeptide+His affinity tag expressed in *B. subtilis*.
SEQ ID NO: 19 is the His affinity tag sequence.
SEQ ID NO: 20 is the amino acid sequence of the *Bacillus clausii* secretion signal.
SEQ ID NO: 21 is the amino acid sequence of a xanthan lyase XLa from a *Paenibacillus* sp (SEQ ID NO: 8 from WO2013167581).
SEQ ID NO: 22 is the amino acid sequence of a xanthan lyase XLb from a *Paenibacillus* sp (SEQ ID NO: 66 from WO2013167581).
SEQ ID NO: 23 is the amino acid sequence of a xanthan lyase XLc from a *Paenibacillus* sp (SEQ ID NO: 68 from WO2013167581).
SEQ ID NO: 24 is the amino acid sequence of a xanthan lyase XLd from a *Paenibacillus* sp (SEQ ID NO: 120 from WO2013167581).

| Identity Matrix for mature peptides | | | | |
| --- | --- | --- | --- | --- |
| | SEQ ID NO: 2 EXa | SEQ ID NO: 4 EXb | SEQ ID NO: 6 EXc | SEQ ID NO: 8 EXd |
| SEQ ID NO: 2 EXa | | 50 | 71 | 27 |
| SEQ ID NO: 4 EXb | | | 47 | 31 |
| SEQ ID NO: 6 EXc | | | | 27 |
| SEQ ID NO: 8 EXd | | | | |

The present disclosure provides detergent composition comprising GH5 polypeptides having xanthan degrading activity. The polypeptides do not belong to a GH family known to comprise enzymes, which degrade xanthan. In addition, the detergent composition comprising a combination of xanthan lyase and an enzyme of the disclosure having xanthan degrading activity shows a synergistic improved wash performance over using a detergent composition comprising either a xanthan lyase or a GH5 polypeptide alone having xanthan degrading activity.

Definitions

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Colour clarification: During washing and wearing loose or broken fibers can accumulate on the surface of the fabrics.

One consequence can be that the colours of the fabric appear less bright or less intense because of the surface contaminations. Removal of the loose or broken fibers from the textile will partly restore the original colours and looks of the textile. By the term "colour clarification", as used herein, is meant the partial restoration of the initial colours of textile.

Detergent Composition: The term "detergent composition", includes unless otherwise indicated, granular or powder-form all-purpose or heavy-duty washing agents, especially cleaning detergents; liquid, gel or paste-form all-purpose washing agents, especially the so-called heavy-duty liquid (HDL) types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, soap bars, mouthwashes, denture cleaners, car or carpet shampoos, bathroom cleaners; hair shampoos and hair-rinses; shower gels, foam baths; metal cleaners; as well as cleaning auxiliaries such as bleach additives and "stain-stick" or pre-treat types. The terms "detergent composition" and "detergent formulation" are used in reference to mixtures which are intended for use in a wash medium for the cleaning of soiled objects. In some embodiments, the term is used in reference to laundering fabrics and/or garments (e.g., "laundry detergents"). In alternative embodiments, the term refers to other detergents, such as those used to clean dishes, cutlery, etc. (e.g., "dishwashing detergents"). It is not intended that the present disclosure be limited to any particular detergent formulation or composition. The term "detergent composition" is not intended to be limited to compositions that contain surfactants. It is intended that in addition to the variants as contemplated herein, the term encompasses detergents that may contain, e.g., surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anticorrosion agents, enzyme inhibitors or stabilizers, enzyme activators, transferase(s), hydrolytic enzymes, oxido reductases, bluing agents and fluorescent dyes, antioxidants, and solubilizers.

Dish wash: The term "dish wash" refers to all forms of washing dishes, e.g., by hand or automatic dish wash. Washing dishes includes, but is not limited to, the cleaning of all forms of crockery such as plates, cups, glasses, bowls, all forms of cutlery such as spoons, knives, forks and serving utensils as well as ceramics, plastics, metals, china, glass and acrylics.

Dish washing composition: The term "dish washing composition" refers to all forms of compositions for cleaning hard surfaces. The present disclosure is not restricted to any particular type of dish wash composition or any particular detergent.

Enzyme Detergency benefit: The term "enzyme detergency benefit" is defined herein as the advantageous effect an enzyme may add to a detergent compared to the same detergent without the enzyme. Important detergency benefits which can be provided by enzymes are stain removal with no or very little visible soils after washing and or cleaning, prevention or reduction of redeposition of soils released in the washing process an effect that also is termed anti-redeposition, restoring fully or partly the whiteness of textiles, which originally were white but after repeated use and wash have obtained a greyish or yellowish appearance an effect that also is termed whitening. Textile care benefits, which are not directly related to catalytic stain removal or prevention of redeposition of soils are also important for enzyme detergency benefits. Examples of such textile care benefits are prevention or reduction of dye transfer from one fabric to another fabric or another part of the same fabric an effect that is also termed dye transfer inhibition or anti-backstaining, removal of protruding or broken fibers from a fabric surface to decrease pilling tendencies or remove already existing pills or fuzz an effect that also is termed anti-pilling, improvement of the fabric-softness, colour clarification of the fabric and removal of particulate soils which are trapped in the fibers of the fabric or garment. Enzymatic bleaching is a further enzyme detergency benefit where the catalytic activity generally is used to catalyze the formation of bleaching component such as hydrogen peroxide or other peroxides.

Fragment: The term "fragment" means a polypeptide having one or more (e.g., several) amino acids absent from the amino and/or carboxyl terminus of a mature polypeptide or domain; wherein the fragment has xanthan degrading activity.

Hard surface cleaning: The term "Hard surface cleaning" is defined herein as cleaning of hard surfaces wherein hard surfaces may include floors, tables, walls, roofs etc. as well as surfaces of hard objects such as cars (car wash) and dishes (dish wash). Dish washing includes but are not limited to cleaning of plates, cups, glasses, bowls, and cutlery such as spoons, knives, forks, serving utensils, ceramics, plastics, metals, china, glass and acrylics.

Improved wash performance: The term "improved wash performance" is defined herein as a (variant) enzyme (also a blend of enzymes, not necessarily only variants but also backbones, and in combination with certain cleaning composition etc.) displaying an alteration of the wash performance of a protease variant relative to the wash performance of the parent protease variant e.g. by increased stain removal. The term "wash performance" includes wash performance in laundry but also e.g. in dish wash.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance). An isolated substance may be present in a fermentation broth sample; e.g. a host cell may be genetically modified to express the polypeptide of the disclosure. The fermentation broth from that host cell will comprise the isolated polypeptide.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids from about 1 to about 802 of SEQ ID NO: 2. In a second aspect, the mature polypeptide is amino acids from about 1 to about 808 of SEQ ID NO: 4. In a third aspect, the mature polypeptide is amino acids from about 1 to about 800 of SEQ ID NO: 6. In a fourth aspect, the mature polypeptide is amino acids from about 1 to about 657 of SEQ ID NO: 8. It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

Mature polypeptide coding sequence: The term "mature polypeptide coding sequence" means a polynucleotide that encodes a mature polypeptide having xanthan degrading activity. In one aspect, the mature polypeptide coding sequence is nucleotides from about 109 to about 2514 of SEQ ID NO: 1. Nucleotides from about 1 to about 108 of SEQ ID NO: 1 encode a signal peptide. In one aspect, the mature polypeptide coding sequence is nucleotides from about 112 to about 2493 of SEQ ID NO: 3. Nucleotides from about 1 to about 111 of SEQ ID NO: 3 encode a signal peptide. In one aspect, the mature polypeptide coding sequence is nucleotides from about 106 to about 2505 of SEQ ID NO: 5. Nucleotides from about 1 to about 105 of SEQ ID NO: 5 encode a signal peptide. In one aspect, the mature polypeptide coding sequence is nucleotides from about 109 to about 2079 of SEQ ID NO: 7. Nucleotides from about 1 to about 108 of SEQ ID NO: 7 encode a signal peptide.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Sequence identity: The relatedness between two amino acid sequences or between two nucleotide sequences is described by the parameter "sequence identity".

For purposes of the present disclosure, the sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

$$(\text{Identical Residues} \times 100)/(\text{Length of Alignment} - \text{Total Number of Gaps in Alignment})$$

For purposes of the present disclosure, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

$$(\text{Identical Deoxyribonucleotides} \times 100)/(\text{Length of Alignment} - \text{Total Number of Gaps in Alignment})$$

Textile: The term "textile" means any textile material including yarns, yarn intermediates, fibers, non-woven materials, natural materials, synthetic materials, and any other textile material, fabrics made of these materials and products made from fabrics (e.g., garments and other articles). The textile or fabric may be in the form of knits, wovens, denims, non-wovens, felts, yarns, and towelling. The textile may be cellulose based such as natural cellulosics, including cotton, flax/linen, jute, ramie, sisal or coir or manmade cellulosics (e.g. originating from wood pulp) including viscose/rayon, ramie, cellulose acetate fibers (tricell), lyocell or blends thereof. The textile or fabric may also be non-cellulose based such as natural polyamides including wool, camel, cashmere, mohair, rabit and silk or synthetic polymer such as nylon, aramid, polyester, acrylic, polypropylen and spandex/elastane, or blends thereof as well as blend of cellulose based and non-cellulose based fibers. Examples of blends are blends of cotton and/or rayon/viscose with one or more companion material such as wool, synthetic fibers (e.g. polyamide fibers, acrylic fibers, polyester fibers, polyvinyl alcohol fibers, polyvinyl chloride fibers, polyurethane fibers, polyurea fibers, aramid fibers), and cellulose-containing fibers (e.g. rayon/viscose, ramie, flax/linen, jute, cellulose acetate fibers, lyocell). Fabric may be conventional washable laundry, for example stained household laundry. When the term fabric or garment is used it is intended to include the broader term textiles as well.

Textile care benefit: "Textile care benefits", which are not directly related to catalytic stain removal or prevention of redeposition of soils, are also important for enzyme detergency benefits. Examples of such textile care benefits are prevention or reduction of dye transfer from one textile to another textile or another part of the same textile an effect that is also termed dye transfer inhibition or anti-backstaining, removal of protruding or broken fibers from a textile surface to decrease pilling tendencies or remove already existing pills or fuzz an effect that also is termed anti-pilling, improvement of the textile-softness, colour clarification of the textile and removal of particulate soils which are trapped in the fibers of the textile. Enzymatic bleaching is a further enzyme detergency benefit where the catalytic activity generally is used to catalyze the formation of bleaching component such as hydrogen peroxide or other peroxides or other bleaching species.

Wash performance: The term "wash performance" is used as an enzyme's ability to remove stains present on the object to be cleaned during e.g. wash or hard surface cleaning. The improvement in the wash performance may be quantified by calculating the so-called intensity value (Int) as defined in 'Automatic Mechanical Stress Assay (AMSA) for laundry' herein. See also the wash performance test in Example 18 herein.

Whiteness: The term "Whiteness" is defined herein as a broad term with different meanings in different regions and for different customers. Loss of whiteness can e.g. be due to greying, yellowing, or removal of optical brighteners/hueing agents. Greying and yellowing can be due to soil redeposition, body soils, colouring from e.g. iron and copper ions or dye transfer. Whiteness might include one or several issues from the list below: colorant or dye effects; incomplete stain removal (e.g. body soils, sebum etc.); re-deposition (greying, yellowing or other discolorations of the object) (removed soils re-associates with other part of textile, soiled or unsoiled); chemical changes in textile during application; and clarification or brightening of colours.

Xanthan Lyase: The term "xanthan lyase" is defined herein as an enzyme that cleaves the beta-D-mannosyl-beta-D-1,4-glucuronosyl bonds in xanthan gum (EC 4.2.2.12). For purposes of the present disclosure, xanthan lyase activity is determined according to the procedure described in the Examples in the 'Xanthan lyase activity assay.

Xanthan degrading activity: The term "xanthan degrading activity" is defined herein as ability to cause viscosity reduction of a xanthan solution. Xanthan solution is highly viscous even at low polymer concentrations, and this viscosity is associated with the polymer degree of xanthan. Therefore, viscosity reduction can be used to monitor xanthan degradation. The viscosity reduction may be detected using the viscosity pressure assay described in Example 6.

Xanthan degrading activity includes activity towards intact xanthan as well as activity towards xanthan pretreated with xanthan lyase (modified xanthan gum—see Example 8).

Activity on xanthan gum: The term "GH5 polypeptide having activity on xanthan gum" or a "polypeptide having activity on xanthan gum and belonging to the GH5 class of glycosyl hydrolases" is defined as a polypeptide comprising a domain belonging to the GH5 class of glycosyl hydrolases, and having significant activity on xanthan gum. In one aspect of the disclosure a GH5 polypeptide having activity on xanthan gum may be a polypeptide having a sequence selected among SEQ ID NO: 2, SEQ ID NO: 4, SEQ ID NO: 6, and SEQ ID NO: 8.

Activity on xanthan gum pretreated with xanthan lyase: The term "GH5 polypeptide having activity on xanthan gum pretreated with xanthan lyase" or a "polypeptide having activity on xanthan gum pretreated with xanthan lyase and belonging to the GH5 class of glycosyl hydrolases" is defined as a polypeptide comprising a domain belonging to the GH5 class of glycosyl hydrolases, and having significant activity on xanthan gum pretreated with xanthan lyase (modified xanthan gum—see Example 8). In one aspect of the disclosure a GH5 polypeptide having activity on xanthan gum pretreated with xanthan lyase may be a polypeptide having a sequence selected among SEQ ID NO: 2, SEQ ID NO: 4, SEQ ID NO: 6, and SEQ ID NO: 8.

Detergent Compositions Comprising Polypeptides Having Xanthan Degrading Activity In an embodiment, the present disclosure relates to detergent compositions comprising polypeptides having a sequence identity to the mature polypeptide of any of SEQ ID NO: 2, 4, 6 and 8 of at least about 60%, e.g., at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100%, which have xanthan degrading activity. In one aspect, the polypeptides differ by up to 10 amino acids, e.g., 1, 2, 3, 4, 5, 6, 7, 8, 9, or 10, from the mature polypeptide of any of SEQ ID NO: 2, 4, 6 and 8.

In a particular embodiment the disclosure relates to detergent compositions comprising polypeptides having a sequence identity to the mature polypeptide of any of SEQ ID NO: 2, 4, 6 and 8 of at least about 60%, e.g., at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100%, and wherein the polypeptide has at least at least 70% of the xanthan degrading activity of the mature polypeptide of any of SEQ ID NO: 2, 4, 6 and 8.

In a particular embodiment the disclosure relates to detergent compositions comprising polypeptides having a sequence identity to the mature polypeptide of any of SEQ ID NO: 2, 4, 6 and 8 of at least about 60%, e.g., at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100%, and wherein the polypeptide has at least at least 75% of the xanthan degrading activity of the mature polypeptide of any of SEQ ID NO: 2, 4, 6 and 8.

In a particular embodiment the disclosure relates to detergent compositions comprising polypeptides having a sequence identity to the mature polypeptide of any of SEQ ID NO: 2, 4, 6 and 8 of at least about 60%, e.g., at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100%, and wherein the polypeptide has at least at least about 80% of the xanthan degrading activity of the mature polypeptide of any of SEQ ID NO: 2, 4, 6 and 8.

In a particular embodiment the disclosure relates to detergent compositions comprising polypeptides having a sequence identity to the mature polypeptide of any of SEQ ID NO: 2, 4, 6 and 8 of at least about 60%, e.g., at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100%, and wherein the polypeptide has at least at least about 85% of the xanthan degrading activity of the mature polypeptide of any of SEQ ID NO: 2, 4, 6 and 8.

In a particular embodiment the disclosure relates to detergent compositions comprising polypeptides having a sequence identity to the mature polypeptide of any of SEQ ID NO: 2, 4, 6 and 8 of at least about 60%, e.g., at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100%, and wherein the polypeptide has at least at least about 90% of the xanthan degrading activity of the mature polypeptide of any of SEQ ID NO: 2, 4, 6 and 8.

In a particular embodiment the disclosure relates to detergent compositions comprising polypeptides having a sequence identity to the mature polypeptide of any of SEQ ID NO: 2, 4, 6 and 8 of at least about 60%, e.g., at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100%, and wherein the polypeptide has at least at least about 95% of the xanthan degrading activity of the mature polypeptide of any of SEQ ID NO: 2, 4, 6 and 8.

In a particular embodiment the disclosure relates to detergent compositions comprising polypeptides having a sequence identity to the mature polypeptide of any of SEQ ID NO: 2, 4, 6 and 8 of at least about 60%, e.g., at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100%, and wherein the polypeptide has 100% of the xanthan degrading activity of the mature polypeptide of any of SEQ ID NO: 2, 4, 6 and 8.

In an embodiment, the polypeptide comprised in the detergent composition of present disclosure has been isolated. A polypeptide preferably comprises or consists of the amino acid sequence of any of SEQ ID NO: 2, 4, 6 and 8 or an allelic variant thereof; or is a fragment thereof having xanthan degrading activity. In another aspect, the polypeptide comprises or consists of the mature polypeptide of any of SEQ ID NO: 2, 4, 6 and 8. In another aspect, the polypeptide comprises or consists of amino acids from about 1 to about 802 of SEQ ID NO: 2, amino acids from about 1 to about 808 of SEQ ID NO: 4, amino acids from about 1 to about 800 of SEQ ID NO: 6, or amino acids from about 1 to about 657 of SEQ ID NO: 8.

In another embodiment, the present disclosure relates to a detergent compositions comprising a polypeptide having xanthan degrading activity encoded by a polynucleotide that hybridizes under very low stringency conditions, low stringency conditions, medium stringency conditions, medium-high stringency conditions, high stringency conditions, or very high stringency conditions with (i) the mature polypeptide coding sequence of SEQ ID NO: 1, (ii), or (iii) the full-length complement of (i) or (ii). In an embodiment, the polypeptide comprised in the detergent composition has been isolated.

For purposes of the present disclosure, hybridization indicates that the polynucleotide hybridizes to a labeled nucleic acid probe corresponding to (i) any of SEQ ID NO: 1, 3, 5, or 7; (ii) the mature polypeptide coding sequence of any of SEQ ID NO: 1, 3, 5, or 7; (iii) the full-length complement thereof; or (iv) a subsequence thereof; under very low to very high stringency conditions. Molecules to which the nucleic acid probe hybridizes under these conditions can be detected using, for example, X-ray film or any other detection means known in the art.

In another embodiment, the present disclosure relates to a detergent compositions comprising a polypeptide having xanthan degrading activity encoded by a polynucleotide having a sequence identity to the mature polypeptide coding sequence of any of SEQ ID NO: 1, 3, 5, or 7 of at least about 60%, e.g., at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100%. In a further embodiment, the polypeptide has been isolated.

In another embodiment, the present disclosure relates to detergent compositions comprising variants of the mature polypeptide of any of SEQ ID NO: 2, 4, 6 and 8 comprising a substitution, deletion, and/or insertion at one or more (e.g., several) positions. In an embodiment, the number of amino acid substitutions, deletions and/or insertions introduced into the mature polypeptide of any of SEQ ID NO: 2, 4, 6 and 8 is up to 10, e.g., 1, 2, 3, 4, 5, 6, 7, 8, 9, or 10. The amino acid changes may be of a minor nature, that is conservative amino acid substitutions or insertions that do not significantly affect the folding and/or activity of the protein; small deletions, typically of from about 1-30 amino acids; small amino- or carboxyl-terminal extensions, such as an amino-terminal methionine residue; a small linker peptide of up to from about 20-25 residues; or a small extension that facilitates purification by changing net charge or another function, such as a poly-histidine tag, an antigenic epitope or a binding domain. SEQ ID NO: 13, 14 and 15 show the polypeptides of the disclosure (SEQ ID NO: 2, 4 and 6) with an N-terminal poly histidine tag (His-tag). SEQ ID NO: 16, 17 and 18 show the polypeptides of the disclosure (SEQ ID NO: 4, 6 and 8) with an N-terminal poly histidine tag.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Sources of Polypeptides Having Xanthan Degrading Activity

A polypeptide having xanthan degrading activity as comprised in the detergent composition of the present disclosure may be obtained from microorganisms of any genus. For purposes of the present disclosure, the term "obtained from" as used herein in connection with a given source shall mean that the polypeptide encoded by a polynucleotide is produced by the source or by a strain in which the polynucleotide from the source has been inserted. In an aspect, the polypeptide is a polypeptide obtained from an *Opitutaceae* species.

Polynucleotides

The present disclosure also relates to polynucleotides encoding a polypeptide, as described herein. In an embodiment, the polynucleotide encoding the polypeptide of the present disclosure has been isolated.

Detergent Composition

In one embodiment of the present disclosure, the polypeptide of the present disclosure may be added to a detergent composition in an amount corresponding to from about 0.0001-200 mg of enzyme protein, such as from about 0.0005-100 mg of enzyme protein, preferably from about 0.001-30 mg of enzyme protein, more preferably from about 0.005-8 mg of enzyme protein, even more preferably from about 0.01-2 mg of enzyme protein per litre of wash liquor.

A composition for use in automatic dishwash (ADW), for example, may include from about 0.0001%-50%, such as from about 0.001%-20%, such as from about 0.01%-10%, such as from about 0.05-5% of enzyme protein by weight of the composition.

A composition for use in laundry powder, for example, may include from about 0.0001%-50%, such as from about 0.001%-20%, such as from about 0.01%-10%, such as from about 0.05%-5% of enzyme protein by weight of the composition.

A composition for use in laundry liquid, for example, may include from about 0.0001%-10%, such as from about 0.001-7%, such as from about 0.1%-5% of enzyme protein by weight of the composition.

The enzyme(s) of the detergent composition of the disclosure may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, for example, WO92/19709 and WO92/19708.

In certain markets different wash conditions and, as such, different types of detergents are used. This is disclosed in e.g. EP 1 025 240. For example, In Asia (Japan) a low detergent concentration system is used, while the United States uses a medium detergent concentration system, and Europe uses a high detergent concentration system.

In one embodiment, the disclosure is directed to detergent compositions comprising an enzyme of the present disclosure in combination with one or more additional cleaning composition components. The choice of additional components is within the skill of the artisan and includes conventional ingredients, including the exemplary non-limiting components set forth below.

The choice of components may include, for textile care, the consideration of the type of textile to be cleaned, the type and/or degree of soiling, the temperature at which cleaning is to take place, and the formulation of the detergent product. Although components mentioned below are categorized by general header according to a particular functionality, this is not to be construed as a limitation, as a component may comprise additional functionalities as will be appreciated by the skilled artisan.

In one embodiment, the disclosure is directed to an ADW (Automatic Dish Wash) composition comprising an enzyme of the present disclosure in combination with one or more additional ADW composition components. The choice of additional components is within the skill of the artisan and includes conventional ingredients, including the exemplary non-limiting components set forth below.

Surfactants

The detergent composition may comprise one or more surfactants, which may be anionic and/or cationic and/or non-ionic and/or semi-polar and/or zwitterionic, or a mixture thereof. In a particular embodiment, the detergent composition includes a mixture of one or more nonionic surfactants and one or more anionic surfactants. The surfactant(s) is typically present at a level of from about 0.1% to about 60% by weight, such as about 1% to about 40%, or about 3% to about 20%, or about 3% to about 10%. The surfactant(s) is chosen based on the desired cleaning application, and may include any conventional surfactant(s) known in the art.

When included therein the detergent will usually contain from about 1% to about 40% by weight of an anionic surfactant, such as from about 5% to about 30%, including from about 5% to about 15%, or from about 15% to about 20%, or from about 20% to about 25% of an anionic surfactant. Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof.

When included therein the detergent will usually contain from about 1% to about 40% by weight of a cationic surfactant, for example from about 0.5% to about 30%, in particular from about 1% to about 20%, from about 3% to about 10%, such as from about 3% to about 5%, from about 8% to about 12% or from about 10% to about 12%. Non-limiting examples of cationic surfactants include alkyldimethylethanolamine quat (ADMEAQ), cetyltrimethylammonium bromide (CTAB), dimethyldistearylammonium chloride (DSDMAC), and alkylbenzyldimethylammonium, alkyl quaternary ammonium compounds, alkoxylated quaternary ammonium (AQA) compounds, ester quats, and combinations thereof.

When included therein the detergent will usually contain from about 0.2% to about 40% by weight of a nonionic surfactant, for example from about 0.5% to about 30%, in particular from about 1% to about 20%, from about 3% to about 10%, such as from about 3% to about 5%, from about 8% to about 12%, or from about 10% to about 12%. Non-limiting examples of nonionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA), as well as products available under the trade names SPAN and TWEEN, and combinations thereof.

When included therein the detergent will usually contain from about 0% to about 10% by weight of a semipolar surfactant. Non-limiting examples of semipolar surfactants include amine oxides (AO) such as alkyldimethylamineoxide, N-(coco alkyl)-N,N-dimethylamine oxide and N-(tallow-alkyl)-N,N-bis(2-hydroxyethyl)amine oxide, and combinations thereof.

When included therein the detergent will usually contain from about 0% to about 10% by weight of a zwitterionic surfactant. Non-limiting examples of zwitterionic surfactants include betaines such as alkyldimethylbetaines, sulfobetaines, and combinations thereof.

Hydrotropes

A hydrotrope is a compound that solubilises hydrophobic compounds in aqueous solutions (or oppositely, polar substances in a non-polar environment). Typically, hydrotropes have both hydrophilic and a hydrophobic character (so-called amphiphilic properties as known from surfactants); however the molecular structure of hydrotropes generally do not favor spontaneous self-aggregation, see e.g. review by Hodgdon and Kaler (2007), Current Opinion in Colloid & Interface Science 12: 121-128. Hydrotropes do not display a critical concentration above which self-aggregation occurs as found for surfactants and lipids forming miceller, lamellar or other well defined meso-phases. Instead, many hydrotropes show a continuous-type aggregation process where the sizes of aggregates grow as concentration increases. However, many hydrotropes alter the phase behavior, stability, and colloidal properties of systems containing substances of polar and non-polar character, including mixtures of water, oil, surfactants, and polymers. Hydrotropes are classically used across industries from pharma, personal care, food, to technical applications. Use of hydrotropes in detergent compositions allow for example more concentrated formulations of surfactants (as in the process of compacting liquid detergents by removing water) without inducing undesired phenomena such as phase separation or high viscosity.

The detergent may contain from about 0-10% by weight, for example from about 0-5% by weight, such as from about 0.5 to about 5%, or from about 3% to about 5%, of a hydrotrope. Any hydrotrope known in the art for use in detergents may be utilized. Non-limiting examples of hydrotropes include sodium benzenesulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Builders and Co-Builders

The detergent composition may contain from about 0-65% by weight, such as from about 5% to about 50% of a detergent builder or co-builder, or a mixture thereof. In a dish wash detergent, the level of builder is typically from about 40-65%, particularly from about 50-65%. The builder and/or co-builder may particularly be a chelating agent that forms water-soluble complexes with Ca and Mg. Any builder and/or co-builder known in the art for use in detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), diethanolamine (DEA, also known as 2,2'-iminodiethan-1-ol), triethanolamine (TEA, also known as 2,2',2"-nitrilotriethan-1-ol), and (carboxymethyl)inulin (CMI), and combinations thereof.

The detergent composition may also contain from about 0-50% by weight, such as from about 5% to about 30%, of a detergent co-builder. The detergent composition may include a co-builder alone, or in combination with a builder, for example a zeolite builder. Non-limiting examples of co-builders include homopolymers of polyacrylates or copolymers thereof, such as poly(acrylic acid) (PAA) or copoly(acrylic acid/maleic acid) (PAA/PMA). Further non-limiting examples include citrate, chelators such as aminocarboxylates, aminopolycarboxylates and phosphonates, and alkyl- or alkenylsuccinic acid. Additional specific examples include 2,2',2"-nitrilotriacetic acid (NTA), ethylenediaminetetraacetic acid (EDTA), diethylenetriaminepentaacetic acid (DTPA), iminodisuccinic acid (IDS), ethylenediamine-N,N'-disuccinic acid (EDDS), methylglycinediacetic acid (MGDA), glutamic acid-N,N-diacetic acid (GLDA), 1-hydroxyethane-1,1-diphosphonic acid (HEDP), ethylenediaminetetra(methylenephosphonic acid) (EDTMPA), diethylenetriaminepentakis(methylenephosphonic acid) (DTMPA or DTPMPA), N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl)-aspartic acid (SMAS), N-(2-sulfoethyl)-aspartic acid (SEAS), N-(2-sulfomethyl)-glutamic acid (SMGL), N-(2-sulfoethyl)-glutamic acid (SEGL), N-methyliminodiacetic acid (MIDA), alpha-alanine-N,N-diacetic acid (α-ALDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA), N-(2-hydroxyethyl)ethylenediamine-N,N',N"-triacetic acid (HEDTA), diethanolglycine (DEG), diethylenetriamine penta(methylenephosphonic acid) (DTPMP), aminotris(methylenephosphonic acid) (ATMP), and combinations and salts thereof. Further exemplary builders and/or co-builders are described in, e.g., WO 09/102854, U.S. Pat. No. 5,977,053

Bleaching Systems

The detergent may contain from about 0-30% by weight, such as from about 1% to about 20%, of a bleaching system. Any bleaching system known in the art for use in detergents may be utilized. Suitable bleaching system components include bleaching catalysts, photobleaches, bleach activators, sources of hydrogen peroxide such as sodium percarbonate, sodium perborates and hydrogen peroxide-urea (1:1), preformed peracids and mixtures thereof. Suitable preformed peracids include, but are not limited to, peroxycarboxylic acids and salts, diperoxydicarboxylic acids, perimidic acids and salts, peroxymonosulfuric acids and salts, for example, Oxone®, and mixtures thereof. Non-limiting examples of bleaching systems include peroxide-based bleaching systems, which may comprise, for example, an inorganic salt, including alkali metal salts such as sodium salts of perborate (usually mono- or tetra-hydrate), percarbonate, persulfate, perphosphate, persilicate salts, in combination with a peracid-forming bleach activator. The term bleach activator is meant herein as a compound which reacts with hydrogen peroxide to form a peracid via perhydrolysis. The peracid thus formed constitutes the activated bleach. Suitable bleach activators to be used herein include those belonging to the class of esters, amides, imides or anhydrides. Suitable examples are tetraacetylethylenediamine (TAED), sodium 4-[(3,5,5-trimethylhexanoyl)oxy]benzene-1-sulfonate (ISONOBS), 4-(dodecanoyloxy)benzene-1-sulfonate (LOBS), 4-(decanoyloxy)benzene-1-sulfonate, 4-(decanoyloxy)benzoate (DOBS or DOBA), 4-(nonanoyloxy)benzene-1-sulfonate (NOBS), and/or those disclosed in WO98/17767. A particular family of bleach activators of interest was disclosed in EP624154 and particulary preferred in that family is acetyl triethyl citrate (ATC). ATC or a short chain triglyceride like triacetin has the advantage that it is environmentally friendly Furthermore acetyl triethyl citrate and triacetin have good hydrolytical stability in the product upon storage and are efficient bleach activators. Finally ATC is multifunctional, as the citrate released in the perhydrolysis reaction may function as a builder. Alternatively, the bleaching system may comprise peroxyacids of, for example, the amide, imide, or sulfone type. The bleaching system may also comprise peracids such as 6-(phthalimido)peroxyhexanoic acid (PAP). The bleaching system may also include a bleach catalyst. In some embodiments the bleach component may be an organic catalyst selected from the group consisting of organic catalysts having the following formulae:

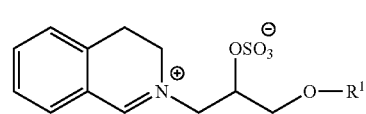

(i)

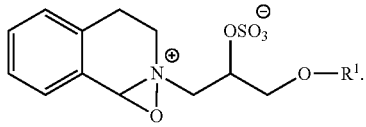

(iii) and mixtures thereof;
wherein each $R^1$ is independently a branched alkyl group containing from about 9 to about 24 carbons or linear alkyl group containing from about 11 to about 24 carbons, preferably each $R^1$ is independently a branched alkyl group containing from about 9 to about 18 carbons or linear alkyl group containing from about 11 to about 18 carbons, more preferably each $R^1$ is independently selected from the group consisting of 2-propylheptyl, 2-butyloctyl, 2-pentylnonyl, 2-hexyldecyl, dodecyl, tetradecyl, hexadecyl, octadecyl, isononyl, isodecyl, isotridecyl and isopentadecyl. Other exemplary bleaching systems are described, e.g. in WO2007/087258, WO2007/087244, WO2007/087259, EP1867708 (Vitamin K) and WO2007/087242. Suitable photobleaches may for example be sulfonated zinc or aluminium phthalocyanines.

Preferably the bleach component comprises a source of peracid in addition to bleach catalyst, particularly organic bleach catalyst. The source of peracid may be selected from (a) pre-formed peracid; (b) percarbonate, perborate or persulfate salt (hydrogen peroxide source) preferably in combination with a bleach activator; and (c) perhydrolase enzyme and an ester for forming peracid in situ in the presence of water in a textile or hard surface treatment step.

Polymers

The detergent may contain from about 0-10% by weight, such as from about 0.5-5%, to about 2-5%, to about 0.5-2% or to about 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or anti-foaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly(ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly(oxyethene terephthalate) (PET-POET), PVP, poly(vinylimidazole) (PVI), poly(vinylpyridine-N-oxide) (PVPO or PVPNO) and polyvinylpyrrolidone-vinylimidazole (PVPVI). Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated.

Fabric Hueing Agents

The detergent compositions of the present disclosure may also include fabric hueing agents such as dyes or pigments, which when formulated in detergent compositions can deposit onto a fabric when said fabric is contacted with a wash liquor comprising said detergent compositions and thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO2005/03274, WO2005/03275, WO2005/03276 and EP1876226 (hereby incorporated by reference). The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from about 0.0001 wt % to about 0.2 wt % fabric hueing agent, this may be especially preferred when the composition is in the form of a unit dose pouch. Suitable hueing agents are also disclosed in, e.g. WO 2007/087257 and WO2007/087243.

Additional Enzymes

The detergent additive as well as the detergent composition may comprise one or more additional enzymes such as a protease, a lipase, a cutinase, an amylase, a carbohydrase, a cellulase, a pectinase, a mannanase, an arabinase, a galactanase, a xylanase, an oxidase, e.g., a laccase, and/or a peroxidase and/or a xanthan lyase.

In general the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and WO99/001544.

Other cellulases are endo-beta-1,4-glucanase enzyme having a sequence of at least about 97% identity to the amino acid sequence of position from about 1 to about position 773 of SEQ ID NO:2 of WO 2002/099091 or a family 44 xyloglucanase, which a xyloglucanase enzyme having a sequence of at least 60% identity to positions 40-559 of SEQ ID NO: 2 of WO 2001/062903.

Commercially available cellulases include Celluzyme™, and Carezyme™ (Novozymes A/S) Carezyme Premium™ (Novozymes A/S), Celluclean™ (Novozymes A/S), Celluclean Classic™ (Novozymes A/S), Cellusoft™ (Novozymes A/S), Whitezyme™ (Novozymes A/S), Clazinase™, and Puradax HA™ (Genencor International Inc.), and KAC-500(B)™ (Kao Corporation).

Mannanases

Suitable mannanases include those of bacterial or fungal origin. Chemically or genetically modified mutants are included. The mannanase may be an alkaline mannanase of Family 5 or 26. It may be a wild-type from *Bacillus* or *Humicola*, particularly *B. agaradhaerens, B. licheniformis, B. halodurans, B. clausii*, or *H. insolens*. Suitable mannanases are described in WO 1999/064619. A commercially available mannanase is Mannaway (Novozymes A/S).

Xanthan Lyases

Suitable xanthan lyases include those of plant, bacterial or fungal origin. Chemically modified or protein engineered mutants are included. Examples of useful enzymes include the xanthan lyases disclosed in WO2013167581 and shown herein as SEQ ID NO:21, 22, 23 and 24.

Proteases

Suitable proteases include those of bacterial, fungal, plant, viral or animal origin e.g. vegetable or microbial origin. Microbial origin is preferred. Chemically modified or protein engineered mutants are included. It may be an alkaline protease, such as a serine protease or a metalloprotease. A serine protease may for example be of the S1 family, such as trypsin, or the S8 family such as subtilisin. A metalloproteases protease may for example be a thermolysin from e.g. family M4 or other metalloprotease such as those from M5, M7 or M8 families.

The term "subtilases" refers to a sub-group of serine protease according to Siezen et al., Protein Engng. 4 (1991) 719-737 and Siezen et al. Protein Science 6 (1997) 501-523. Serine proteases are a subgroup of proteases characterized by having a serine in the active site, which forms a covalent adduct with the substrate. The subtilases may be divided into 6 sub-divisions, i.e. the Subtilisin family, the Thermitase family, the Proteinase K family, the Lantibiotic peptidase family, the Kexin family and the Pyrolysin family.

Examples of subtilases are those derived from *Bacillus* such as *Bacillus lentus, B. alkalophilus, B. subtilis, B. amyloliquefaciens, Bacillus pumilus* and *Bacillus gibsonii* described in; U.S. Pat. No. 7,262,042 and WO09/021867, and subtilisin *lentus*, subtilisin Novo, subtilisin Carlsberg, *Bacillus licheniformis*, subtilisin BPN', subtilisin 309, subtilisin 147 and subtilisin 168 described in WO89/06279 and protease PD138 described in (WO93/18140). Other useful proteases may be those described in WO92/175177, WO01/016285, WO02/026024 and WO02/016547. Examples of trypsin-like proteases are trypsin (e.g. of porcine or bovine origin) and the *Fusarium* protease described in WO89/06270, WO94/25583 and WO05/040372, and the chymotrypsin proteases derived from *Cellumonas* described in WO05/052161 and WO05/052146.

A further preferred protease is the alkaline protease from *Bacillus lentus* DSM 5483, as described for example in WO95/23221, and variants thereof which are described in WO92/21760, WO95/23221, EP1921147 and EP1921148.

Examples of metalloproteases are the neutral metalloprotease as described in WO07/044993 (Genencor Int.) such as those derived from *Bacillus amyloliquefaciens*.

Examples of useful proteases are the variants described in: WO92/19729, WO96/034946, WO98/20115, WO98/20116, WO99/011768, WO01/44452, WO03/006602, WO04/03186, WO04/041979, WO07/006305, WO11/036263, WO11/036264, especially the variants with substitutions in one or more of the following positions: 3, 4, 9, 15, 27, 36, 57, 68, 76, 87, 95, 96, 97, 98, 99, 100, 101, 102, 103, 104, 106, 118, 120, 123, 128, 129, 130, 160, 167, 170, 194, 195, 199, 205, 206, 217, 218, 222, 224, 232, 235, 236, 245, 248, 252 and 274 using the BPN' numbering. More preferred the subtilase variants may comprise the mutations: S3T, V4I, S9R, A15T, K27R, *36D, V68A, N76D, N87S,R, *97E, A98S, S99G,D,A, S99AD, S101G,M,R S103A, V104I,Y,N, S106A, G118V,R, H120D,N, N123S, S128L, P129Q, S130A, G160D, Y167A, R170S, A194P, G195E, V199M, V205I, L217D, N218D, M222S, A232V, K235L, Q236H, Q245R, N252K, T274A (using BPN' numbering).

Suitable commercially available protease enzymes include those sold under the trade names Alcalase®, Duralase™, Durazym™, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Blaze®, Neutrase®, Everlase® and Esperase® (Novozymes A/S), those sold under the tradename Maxatase®, Maxacal®, Maxapem®, Purafect®, Purafect Prime®, Purafect MA®, Purafect Ox®, Purafect OxP®, Puramax®, Properase®, FN2®, FN3®, FN4®, Excellase®, Eraser®, Opticlean® and Optimase® (Danisco/DuPont), Axapem™ (Gist-Brocases N.V.), BLAP (sequence shown in FIG. 29 of U.S. Pat. No. 5,352,604) and variants hereof (Henkel AG) and KAP (*Bacillus alkalophilus* subtilisin) from Kao.

Lipases and Cutinases

Suitable lipases and cutinases include those of bacterial or fungal origin. Chemically modified or protein engineered mutant enzymes are included. Examples include lipase from *Thermomyces*, e.g. from *T. lanuginosus* (previously named *Humicola lanuginosa*) as described in EP258068 and EP305216, cutinase from *Humicola*, e.g. *H. insolens* (WO96/13580), lipase from strains of *Pseudomonas* (some of these now renamed to *Burkholderia*), e.g. *P. alcaligenes* or *P. pseudoalcaligenes* (EP218272), *P. cepacia* (EP331376), P. sp. strain SD705 (WO95/06720 & WO96/27002), *P. wisconsinensis* (WO96/12012), GDSL-type *Streptomyces* lipases (WO10/065455), cutinase from *Magnaporthe grisea* (WO10/107560), cutinase from *Pseudomonas mendocina* (U.S. Pat. No. 5,389,536), lipase from *Thermobifida fusca* (WO11/084412), *Geobacillus stearothermophilus* lipase (WO11/084417), lipase from *Bacillus subtilis* (WO11/084599), and lipase from *Streptomyces griseus* (WO11/150157) and *S. pristinaespiralis* (WO12/137147).

Other examples are lipase variants such as those described in EP407225, WO92/05249, WO94/01541, WO94/25578, WO95/14783, WO95/30744, WO95/35381, WO95/22615, WO96/00292, WO97/04079, WO97/07202, WO00/34450, WO00/60063, WO01/92502, WO07/87508 and WO09/109500.

Preferred commercial lipase products include Lipolase™, Lipex™; Lipolex™ and Lipoclean™ (Novozymes A/S), Lumafast (originally from Genencor) and Lipomax (originally from Gist-Brocades).

Still other examples are lipases sometimes referred to as acyltransferases or perhydrolases, e.g. acyltransferases with homology to *Candida antarctica* lipase A (WO10/111143), acyltransferase from *Mycobacterium smegmatis* (WO05/56782), perhydrolases from the CE 7 family (WO09/67279), and variants of the *M. smegmatis* perhydrolase in particular the S54V variant used in the commercial product Gentle Power Bleach from Huntsman Textile Effects Pte Ltd (WO10/100028).

Amylases

Suitable amylases which can be used together with the enzyme of the disclosure may be an alpha-amylase or a glucoamylase and may be of bacterial or fungal origin. Chemically modified or protein engineered mutants are included. Amylases include, for example, alpha-amylases obtained from *Bacillus*, e.g., a special strain of *Bacillus licheniformis*, described in more detail in GB 1,296,839.

Suitable amylases include amylases having SEQ ID NO: 2 in WO 95/10603 or variants having 90% sequence identity to SEQ ID NO: 3 thereof. Preferred variants are described in WO 94/02597, WO 94/18314, WO 97/43424 and SEQ ID NO: 4 of WO 99/019467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444.

Different suitable amylases include amylases having SEQ ID NO: 6 in WO 02/010355 or variants thereof having 90% sequence identity to SEQ ID NO: 6. Preferred variants of SEQ ID NO: 6 are those having a deletion in positions 181 and 182 and a substitution in position 193.

Other amylases which are suitable are hybrid alpha-amylase comprising residues from about 1-33 of the alpha-amylase derived from *B. amyloliquefaciens* shown in SEQ ID NO: 6 of WO 2006/066594 and residues from about 36-483 of the *B. licheniformis* alpha-amylase shown in SEQ ID NO: 4 of WO 2006/066594 or variants having 90% sequence identity thereof. Preferred variants of this hybrid alpha-amylase are those having a substitution, a deletion or an insertion in one of more of the following positions: G48, T49, G107, H156, A181, N190, M197, I201, A209 and Q264. Most preferred variants of the hybrid alpha-amylase comprising residues from about 1-33 of the alpha-amylase derived from *B. amyloliquefaciens* shown in SEQ ID NO: 6 of WO 2006/066594 and residues from about 36-483 of SEQ ID NO: 4 are those having the substitutions:
M197T;
H156Y+A181T+N190F+A209V+Q264S; or
G48A+T49I+G107A+H156Y+A181T+N190F+I201F+A209V+Q264S.

Further amylases which are suitable are amylases having SEQ ID NO: 6 in WO 99/019467 or variants thereof having 90% sequence identity to SEQ ID NO: 6. Preferred variants of SEQ ID NO: 6 are those having a substitution, a deletion or an insertion in one or more of the following positions: R181, G182, H183, G184, N195, I206, E212, E216 and K269. Particularly preferred amylases are those having deletion in positions R181 and G182, or positions H183 and G184.

Additional amylases which can be used are those having SEQ ID NO: 1, SEQ ID NO: 3, SEQ ID NO: 2 or SEQ ID NO: 7 of WO 96/023873 or variants thereof having about 90% sequence identity to SEQ ID NO: 1, SEQ ID NO: 2, SEQ ID NO: 3 or SEQ ID NO: 7. Preferred variants of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476, using SEQ ID 2 of WO 96/023873 for numbering. More preferred variants are those having a deletion in two positions selected from 181, 182, 183 and 184, such as 181 and 182, 182 and 183, or positions 183 and 184. Most preferred amylase variants of SEQ ID NO: 1, SEQ ID NO: 2 or SEQ ID NO: 7 are those having a deletion in positions 183 and 184 and a substitution in one or more of positions 140, 195, 206, 243, 260, 304 and 476.

Other amylases which can be used are amylases having SEQ ID NO: 2 of WO 08/153815, SEQ ID NO: 10 in WO 01/66712 or variants thereof having about 90% sequence identity to SEQ ID NO: 2 of WO 08/153815 or about 90% sequence identity to SEQ ID NO: 10 in WO 01/66712. Preferred variants of SEQ ID NO: 10 in WO 01/66712 are those having a substitution, a deletion or an insertion in one of more of the following positions: 176, 177, 178, 179, 190, 201, 207, 211 and 264.

Further suitable amylases are amylases having SEQ ID NO: 2 of WO 09/061380 or variants having about 90% sequence identity to SEQ ID NO: 2 thereof. Preferred variants of SEQ ID NO: 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO: 2 are those having the substitution in one of more of the following positions: Q87E,R, Q98R, S125A, N128C, T131I, T165I, K178L, T182G, M201L, F202Y, N225E,R, N272E,R, S243Q,A,E,D, Y305R, R309A, Q320R, Q359E, K444E and G475K and/or deletion in position R180 and/or S181 or of T182 and/or G183. Most preferred amylase variants of SEQ ID NO: 2 are those having the substitutions:
N128C+K178L+T182G+Y305R+G475K;
N128C+K178L+T182G+F202Y+Y305R+D319T+G475K;
S125A+N128C+K178L+T182G+Y305R+G475K; or
S125A+N128C+T131I+T165I+K178L+T182G+Y305R+G475K wherein the variants are C-terminally truncated and optionally further comprises a substitution at position 243 and/or a deletion at position 180 and/or position 181.

Further suitable amylases are amylases having SEQ ID NO: 1 of WO13184577 or variants having about 90% sequence identity to SEQ ID NO: 1 thereof. Preferred variants of SEQ ID NO: 1 are those having a substitution, a deletion or an insertion in one of more of the following positions: K176, R178, G179, T180, G181, E187, N192, M199, I203, S241, R458, T459, D460, G476 and G477. More preferred variants of SEQ ID NO: 1 are those having the substitution in one of more of the following positions: K176L, E187P, N192FYH, M199L, I203YF, S241QADN, R458N, T459S, D460T, G476K and G477K and/or deletion in position R178 and/or S179 or of T180 and/or G181. Most preferred amylase variants of SEQ ID NO: 1 are those having the substitutions:
E187P+I203Y+G476K
E187P+I203Y+R458N+T459S+D460T+G476K
wherein the variants optionally further comprises a substitution at position 241 and/or a deletion at position 178 and/or position 179.

Further suitable amylases are amylases having SEQ ID NO: 1 of WO10104675 or variants having 90% sequence identity to SEQ ID NO: 1 thereof. Preferred variants of SEQ ID NO: 1 are those having a substitution, a deletion or an insertion in one of more of the following positions: N21, D97, V128 K177, R179, S180, I181, G182, M200, L204, E242, G477 and G478. More preferred variants of SEQ ID NO: 1 are those having the substitution in one of more of the following positions: N21D, D97N, V128I K177L, M200L, L204YF, E242QA, G477K and G478K and/or deletion in position R179 and/or S180 or of I181 and/or G182. Most preferred amylase variants of SEQ ID NO: 1 are those having the substitutions:
N21D+D97N+V128I
wherein the variants optionally further comprises a substitution at position 200 and/or a deletion at position 180 and/or position 181.

Other suitable amylases are the alpha-amylase having SEQ ID NO: 12 in WO01/66712 or a variant having at least about 90% sequence identity to SEQ ID NO: 12. Preferred amylase variants are those having a substitution, a deletion or an insertion in one of more of the following positions of SEQ ID NO: 12 in WO01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particular preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions.

Other examples are amylase variants such as those described in WO2011/098531, WO2013/001078 and WO2013/001087.

Commercially available amylases are Duramyl™, Termamyl™, Fungamyl™, Stainzyme™, Stainzyme Plus™, Natalase™, Liquozyme X and BAN™ (from Novozymes A/S), and Rapidase™, Purastar™/Effectenz™, Powerase, Preferenz S1000, Preferenz S100 and Preferenz S110 (from Genencor International Inc./DuPont).

Peroxidases/Oxidases

A peroxidase as contemplated herein is a peroxidase enzyme comprised by the enzyme classification EC 1.11.1.7, as set out by the Nomenclature Committee of the International Union of Biochemistry and Molecular Biology (IUBMB), or any fragment derived therefrom, exhibiting peroxidase activity.

Suitable peroxidases include those of plant, bacterial or fungal origin. Chemically modified or protein engineered mutants are included. Examples of useful peroxidases include peroxidases from *Coprinopsis*, e.g., from *C. cinerea* (EP 179,486), and variants thereof as those described in WO 93/24618, WO 95/10602, and WO 98/15257.

A peroxidase as contemplated herein also include a haloperoxidase enzyme, such as chloroperoxidase, bromoperoxidase and compounds exhibiting chloroperoxidase or bromoperoxidase activity. Haloperoxidases are classified according to their specificity for halide ions. Chloroperoxidases (E.C. 1.11.1.10) catalyze formation of hypochlorite from chloride ions.

In an embodiment, the haloperoxidase of the disclosure is a chloroperoxidase. Preferably, the haloperoxidase is a vanadium haloperoxidase, i.e., a vanadate-containing haloperoxidase. In a preferred method of the present disclosure the vanadate-containing haloperoxidase is combined with a source of chloride ion.

Haloperoxidases have been isolated from many different fungi, in particular from the fungus group dematiaceous hyphomycetes, such as *Caldariomyces*, e.g., *C. fumago*, *Alternaria*, *Curvularia*, e.g., *C. verruculosa* and *C. inaequalis*, *Drechslera*, *Ulocladium* and *Botrytis*.

Haloperoxidases have also been isolated from bacteria such as *Pseudomonas*, e.g., *P. pyrrocinia* and *Streptomyces*, e.g., *S. aureofaciens*.

In an preferred embodiment, the haloperoxidase is derivable from *Curvularia* sp., in particular *Curvularia verruculosa* or *Curvularia inaequalis*, such as *C. inaequalis* CBS 102.42 as described in WO 95/27046; or *C. verruculosa* CBS 147.63 or *C. verruculosa* CBS 444.70 as described in WO 97/04102; or from *Drechslera hartlebii* as described in WO 01/79459, *Dendryphiella salina* as described in WO 01/79458, *Phaeotrichoconis crotalarie* as described in WO 01/79461, or *Geniculosporium* sp. as described in WO 01/79460.

An oxidase as contemplated herein include, in particular, any laccase enzyme comprised by the enzyme classification EC 1.10.3.2, or any fragment derived therefrom exhibiting laccase activity, or a compound exhibiting a similar activity, such as a catechol oxidase (EC 1.10.3.1), an o-aminophenol oxidase (EC 1.10.3.4), or a bilirubin oxidase (EC 1.3.3.5).

Preferred laccase enzymes are enzymes of microbial origin. The enzymes may be derived from plants, bacteria or fungi (including filamentous fungi and yeasts).

Suitable examples from fungi include a laccase derivable from a strain of *Aspergillus, Neurospora*, e.g., *N. crassa*, *Podospora, Botrytis, Collybia, Fomes, Lentinus, Pleurotus, Trametes*, e.g., *T. villosa* and *T. versicolor, Rhizoctonia*, e.g., *R. solani, Coprinopsis*, e.g., *C. cinerea, C. comatus, C. friesii*, and *C. plicatilis, Psathyrella*, e.g., *P. condelleana, Panaeolus*, e.g., *P. papilionaceus, Myceliophthora*, e.g., *M. thermophila, Schytalidium*, e.g., *S. thermophilum, Polyporus*, e.g., *P. pinsitus, Phlebia*, e.g., *P. radiata* (WO 92/01046), or *Coriolus*, e.g., *C. hirsutus* (JP 2238885).

Suitable examples from bacteria include a laccase derivable from a strain of *Bacillus*.

A laccase derived from *Coprinopsis* or *Myceliophthora* is preferred; in particular a laccase derived from *Coprinopsis cinerea*, as disclosed in WO 97/08325; or from *Myceliophthora thermophila*, as disclosed in WO 95/33836.

The detergent enzyme(s) may be included in a detergent composition by adding separate additives containing one or more enzymes, or by adding a combined additive comprising all of these enzymes. A detergent additive of the disclosure, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Non-dusting granulates may be produced, e.g. as disclosed in U.S. Pat. Nos. 4,106,991 and 4,661,452 and may optionally be coated by methods known in the art. Examples of waxy coating materials are polyethyleneglycol (PEG) with mean molar weights of from about 1000 to about 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

Adjunct Materials

Any detergent components known in the art for use in detergents may also be utilized. Other optional detergent components include anti-corrosion agents, anti-shrink agents, anti-soil redeposition agents, anti-wrinkling agents, bactericides, binders, corrosion inhibitors, disintegrants/disintegration agents, dyes, enzyme stabilizers (including boric acid, borates, CMC, and/or polyols such as propylene glycol), fabric conditioners including clays, fillers/processing aids, fluorescent whitening agents/optical brighteners, foam boosters, foam (suds) regulators, perfumes, soil-suspending agents, softeners, suds suppressors, tarnish inhibitors, and wicking agents, either alone or in combination. Any ingredient known in the art for use in detergents may be utilized. The choice of such ingredients is well within the skill of the artisan.

Dispersants

The detergent compositions of the present disclosure can also contain dispersants. In particular powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

Dye Transfer Inhibiting Agents

The detergent compositions of the present disclosure may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent Whitening Agent

The detergent compositions of the present disclosure will preferably also contain additional components that may tint articles being cleaned, such as fluorescent whitening agent or optical brighteners. Where present the brightener is preferably at a level of from about 0.01% to about 0.5%. Any fluorescent whitening agent suitable for use in a laundry detergent composition may be used in the composition of the present disclosure. The most commonly used fluorescent whitening agents are those belonging to the classes of diaminostilbene-sulfonic acid derivatives, diarylpyrazoline derivatives and bisphenyl-distyryl derivatives. Examples of the diaminostilbene-sulfonic acid derivative type of fluorescent whitening agents include the sodium salts of: 4,4'-bis-(2-diethanolamino-4-anilino-s-triazin-6-ylamino) stilbene-2,2'-disulfonate, 4,4'-bis-(2,4-dianilino-s-triazin-6-ylamino) stilbene-2,2'-disulfonate, 4,4'-bis-(2-anilino-4-(N-methyl-N-2-hydroxy-ethylamino)-s-triazin-6-ylamino) stilbene-2, 2'-disulfonate, 4,4'-bis-(4-phenyl-1,2,3-triazol-2-yl)stilbene-2,2'-disulfonate and sodium 5-(2H-naphtho[1,2-d][1,2,3] triazol-2-yl)-2-[(E)-2-phenylvinyl]benzenesulfonate.

Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4-anilino-s-triazin-6-ylamino) stilbene-2,2'-disulfonate. Tinopal CBS is the disodium salt of 2,2'-bis-(phenyl-styryl)-disulfonate. Also preferred are fluorescent whitening agents is the commercially available Parawhite KX, supplied by Paramount Minerals and Chemicals, Mumbai, India. Other fluorescers suitable for use in the disclosure include the 1-3-diaryl pyrazolines and the 7-alkylaminocoumarins.

Suitable fluorescent brightener levels include lower levels of from about 0.01, from about 0.05, from about 0.1 or even from about 0.2 wt % to upper levels of from about 0.5 or even from about 0.75 wt %.

Soil Release Polymers

The detergent compositions of the present disclosure may also include one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers are amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore random graft co-polymers are suitable soil release polymers. Suitable graft co-polymers are described in more detail in WO 2007/138054, WO 2006/108856 and WO 2006/113314 (hereby incorporated by reference). Other soil release polymers are substituted polysaccharide structures especially substituted cellulosic structures such as modified cellulose deriviatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-Redeposition Agents

The detergent compositions of the present disclosure may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Rheology Modifiers

The detergent compositions of the present disclosure may also include one or more rheology modifiers, structurants or thickeners, as distinct from viscosity reducing agents. The rheology modifiers are selected from the group consisting of non-polymeric crystalline, hydroxy-functional materials, polymeric rheology modifiers which impart shear thinning characteristics to the aqueous liquid matrix of a liquid detergent composition. The rheology and viscosity of the detergent can be modified and adjusted by methods known in the art, for example as shown in EP 2169040.

Formulation of Detergent Products

The detergent composition of the disclosure may be in any convenient form, e.g., a bar, a homogenous tablet, a tablet having two or more layers, a pouch having one or more compartments, a regular or compact powder, a granule, a paste, a gel, or a regular, compact or concentrated liquid.

Pouches can be configured as single or multicompartments. It can be of any form, shape and material which is suitable for hold the composition, e.g. without allowing the release of the composition to release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxypropyl methyl cellulose (HPMC). Preferably the level of polymer in the film for example PVA is at least about 60%. Preferred average molecular weight will typically be from about 20,000 to about 150,000. Films can also be of blended compositions comprising hydrolytically degradable and water soluble polymer blends such as polylactide and polyvinyl alcohol (known under the Trade reference M8630 as sold by MonoSol LLC, Indiana, USA) plus plasticisers like glycerol, ethylene glycerol, propylene glycol, sorbitol and mixtures thereof. The pouches can comprise a solid laundry cleaning composition or part components and/or a liquid cleaning composition or part components separated by the water soluble film. The compartment for liquid components can be different in composition than compartments containing solids: US2009/0011970 A1.

Detergent ingredients can be separated physically from each other by compartments in water dissolvable pouches or in different layers of tablets. Thereby negative storage interaction between components can be avoided. Different dissolution profiles of each of the compartments can also give rise to delayed dissolution of selected components in the wash solution.

A liquid or gel detergent, which is not unit dosed, may be aqueous, typically containing at least about 20% by weight and up to about 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from about 0-30% organic solvent.

A liquid or gel detergent may be non-aqueous.

Laundry Soap Bars

The enzymes of the disclosure may be added to laundry soap bars and used for hand washing laundry, fabrics and/or textiles. The term laundry soap bar includes laundry bars, soap bars, combo bars, syndet bars and detergent bars. The types of bar usually differ in the type of surfactant they contain, and the term laundry soap bar includes those containing soaps from fatty acids and/or synthetic soaps. The laundry soap bar has a physical form which is solid and not a liquid, gel or a powder at room temperature. The term solid is defined as a physical form which does not significantly change over time, i.e. if a solid object (e.g. laundry soap bar) is placed inside a container, the solid object does not change to fill the container it is placed in. The bar is a solid typically in bar form but can be in other solid shapes such as round or oval.

The laundry soap bar may contain one or more additional enzymes, protease inhibitors such as peptide aldehydes (or hydrosulfite adduct or hemiacetal adduct), boric acid, borate, borax and/or phenylboronic acid derivatives such as 4-formylphenylboronic acid, one or more soaps or synthetic surfactants, polyols such as glycerine, pH controlling compounds such as fatty acids, citric acid, acetic acid and/or formic acid, and/or a salt of a monovalent cation and an organic anion wherein the monovalent cation may be for example $Na^+$, $K^+$ or $NH_4^+$ and the organic anion may be for example formate, acetate, citrate or lactate such that the salt of a monovalent cation and an organic anion may be, for example, sodium formate.

The laundry soap bar may also contain complexing agents like EDTA and HEDP, perfumes and/or different type of fillers, surfactants e.g. anionic synthetic surfactants, builders, polymeric soil release agents, detergent chelators, stabilizing agents, fillers, dyes, colorants, dye transfer inhibitors, alkoxylated polycarbonates, suds suppressors, structurants, binders, leaching agents, bleaching activators, clay soil removal agents, anti-redeposition agents, polymeric dispersing agents, brighteners, fabric softeners, perfumes and/or other compounds known in the art.

The laundry soap bar may be processed in conventional laundry soap bar making equipment such as but not limited to: mixers, plodders, e.g a two stage vacuum plodder, extruders, cutters, logo-stampers, cooling tunnels and wrappers. The disclosure is not limited to preparing the laundry soap bars by any single method. The premix of the disclosure may be added to the soap at different stages of the process. For example, the premix containing a soap, the enzyme of the disclosure, optionally one or more additional enzymes, a protease inhibitor, and a salt of a monovalent cation and an organic anion may be prepared and the mixture is then plodded. The enzyme of the disclosure and optional additional enzymes may be added at the same time as the protease inhibitor for example in liquid form. Besides the mixing step and the plodding step, the process may further comprise the steps of milling, extruding, cutting, stamping, cooling and/or wrapping.

Formulation of Enzyme in Co-Granule

The enzyme comprised in the detergent compositions of the disclosure may be formulated as a granule for example as a co-granule that combines one or more enzymes. Each enzyme will then be present in more granules securing a more uniform distribution of enzymes in the detergent. This also reduces the physical segregation of different enzymes due to different particle sizes. Methods for producing multi-enzyme co-granulates for the detergent industry are disclosed in the IP.com disclosure IPCOM000200739D.

Another example of formulation of enzymes by the use of co-granulates are disclosed in WO 2013/188331, which relates to a detergent composition comprising (a) a multi-enzyme co-granule; (b) less than 10 wt zeolite (anhydrous basis); and (c) less than 10 wt phosphate salt (anhydrous basis), wherein said enzyme co-granule comprises from about 10 to about 98 wt % moisture sink component and the composition additionally comprises from about 20 to about 80 wt % detergent moisture sink component.

WO 2013/188331 also relates to a method of treating and/or cleaning a surface, preferably a fabric surface comprising the steps of (i) contacting said surface with the detergent composition as claimed and described herein in an aqueous wash liquor, (ii) rinsing and/or drying the surface.

The multi-enzyme co-granule may comprise an enzyme of the disclosure and (a) one or more enzymes selected from the group consisting of first-wash lipases, cleaning cellulases, xyloglucanases, perhydrolases, peroxidases, lipoxygenases, laccases and mixtures thereof; and (b) one or more enzymes selected from the group consisting of hemicellulases, proteases, care cellulases, cellobiose dehydrogenases, xylanases, phospholipases, esterases, cutinases, pectinases, mannanases, pectate lyases, keratinases, reductases, oxidases, phenoloxidases, ligninases, pullulanases, tannases, pentosanases, lichenases glucanases, arabinosidases, hyaluronidase, chondroitinase, amylases, and mixtures thereof.

Use in Degrading Xanthan Gum

Xanthan gum is used as an ingredient in many consumer products including foods and cosmetics as well as in the oil and drilling industry. Therefore, enzymes having xanthan degrading activity can be applied in improved cleaning processes, such as the easier removal of stains containing xanthan gum, as well as the degradation of xanthan gum, which is often used in the oil and drilling industry. Thus, the present disclosure is directed to the use of the detergent composition of the disclosure to degrade xanthan gum. The detergent composition of present disclosure can also comprise a combination of an enzyme as described herein and a xanthan lyase. The use of such a detergent composition to degrade xanthan gum is also envisaged.

Degradation of xanthan gum may be measured using the viscosity reduction assay as described herein on xanthan gum. Xanthan degrading activity may alternatively be measured as reducing ends on xanthan gum using the colorimetric assay developed by Lever (1972), Anal. Biochem. 47: 273-279, 1972.

Use in Detergents

The present disclosure is directed to the use of the detergent compositions of the disclosure in cleaning processes such as the laundering of textiles and fabrics (e.g. household laundry washing and industrial laundry washing), as well as household and industrial hard surface cleaning, such as dish wash.

An embodiment is the use of a detergent composition comprising a combination of the enzymes as described herein together with xanthan lyases in cleaning processes such as the laundering of textiles and fabrics (e.g. household laundry washing and industrial laundry washing), as well as household and industrial hard surface cleaning, such as dish wash.

The disclosure also relates to methods for degrading xanthan gum on the surface of a textile or hard surface, such as dish wash, comprising applying a detergent composition comprising one or more enzymes as described herein to xanthan gum. The disclosure further relates to methods for degrading xanthan gum on the surface of a textile or hard surface, such as dish wash, comprising applying a detergent composition comprising one or more xanthan lyases to xanthan gum. An embodiment is a method for degrading xanthan gum on the surface of a textile or hard surface, such as dish wash, comprising applying a detergent composition comprising one or more enzymes as described herein together with one or more xanthan lyase to xanthan gum. An embodiment is the detergent composition comprising one or more detergent components as described above.

The present disclosure is further described by the following examples that should not be construed as limiting the scope of the disclosure.

EXAMPLES

Activity Assays
Xanthan Lyase Activity Assay 0.8 mL 100 mM HEPES buffer, pH 6.0 was mixed with 0.2 mL Xanthan gum (5 mg/mL) dissolved in water in a 1 mL 1 cm cuvette. The cuvette was inserted into a spectrophotometer (Agilent G1103A 8453A, CA, USA) with temperature control set at 40° C. The solution was pre-incubated for 10 min and 0.1 mL sample was added and the solution was mixed by aspiring and dispensing the solution for at least 5 times using a pipette. Total reaction volume was 1.1 mL. Absorbance at 235 nm was collected for 10 min using a 30 sec measuring interval. Initial activity was calculated by using the software (UV-Visible Chemstation Rev A.10.01 [81], Agilent).

Example 1: Strain and DNA

The DNA in SEQ ID NO: 1 encoding the GH5 polypeptide EXa of SEQ ID NO: 2 was obtained from an *Opitutaceae* species isolated from an environmental soil sample collected in Denmark.

The DNA SEQ ID NO: 3 encoding the GH5 polypeptide EXb of SEQ ID NO: 4 was isolated from an environmental sample collected in Denmark.

The DNA SEQ ID NO: 5 encoding the GH5 polypeptide EXc of SEQ ID NO: 5 was isolated from an environmental sample collected in Denmark.

The DNA SEQ ID NO: 7 encoding the GH5 polypeptide EXd of SEQ ID NO: 8 was obtained from the public database (UNIPROT M2V1S3) but originates from a strain of *Pseudomonas stutzeri* collected from a Galapagos Rift hydrothermal vent, Ecuador.

Codon optimized synthetic DNA encoding the mature peptide sequences of the four polypeptides were prepared (SEQ ID NO: 9; SEQ ID NO: 10, SEQ ID NO: 11; SEQ ID NO: 12).

Example 2: Cloning and Expression of GH5 Polypeptides

The GH5 encoding genes were either cloned by conventional techniques from the strains indicated above or from the synthetic DNA and inserted into a suitable plasmid as described below.

Example 2a: Cloning and Expression of GH5 Polypeptides in *E. coli*

The mature peptide encoding part of the GH5 endoglucanase genes, SEQ ID NO: 1, 3, 5 and 7 was inserted with an N-terminal poly histidine tag with an extra proline and arginine (HHHHHHPR) (SEQ ID NO: 19) after the methionine in the *E. coli* pET-32a(+) vector from Novagen with standard recombinant techniques. The expression plasmid containing the insert was purified from an *E. coli* transformant harboring the plasmid and transformed into *E. coli* Xjb (DE3) host cells (from Zymo Research). A fresh clone of *E. coli* Xjb (DE3) containing the pET32-GH5 vector, was grown overnight in Terrific Broth containing 100 ug/ml ampicillin. Next day, a fresh 500 ml culture was inoculated with 1 ml overnight culture and cells were cultured (37° C., 250 rpm) to an optical density (OD600) between 6-8. Protein expression was induced by 1 mM isopropylthio-D-galactosidase (IPTG) and 6 mM arabinose for 4.5 hours at 20° C. After continued culture, cells were harvested by centrifugation and lysed by Bugbuster® (Novagen). The soluble fraction was used for polyhistidine tag purification of the GH5 polypeptides SEQ ID NO: 13, 14 and 15 as described in example 4.

Example 2b: Cloning and Expression of GH5 Polypeptides in *Bacillus subtilis*

The synthetic codon optimized genes SEQ ID NO: 10, 11 and 12 were cloned into the *Bacillus* expression vector described in WO 2012/025577. The genes were expressed by replacing the native secretion signal sequence with the *Bacillus clausii* secretion signal MKKPLGKIVASTAL-LISVAFSSSIASA (SEQ ID NO: 20) with an extra affinity tag sequence (HHHHHHPR) (SEQ ID NO: 19) at the C-terminal of the signal peptide, to facilitate the purification process. This resulted in a recombinant mature polypeptide with a His tag at the front of the N-terminal of the mature wild type sequence (SEQ ID NO: 16, 17 and 18).

One clone with the correct recombinant gene sequence was selected and the corresponding plasmid was integrated by homologous recombination into the Bacillus subtilis host cell genome (pectate lyase locus) and the gene construct was expressed under the control of a triple promoter system as described in WO99/43835. The gene coding for chloramphenicol acetyltransferase was used as a marker (as described in Diderichsen et al., 1993, Plasmid 30:312-315).

Chloramphenicol resistant transformants were analyzed by PCR to verify the correct size of the amplified fragment. A recombinant B. subtilis clone containing the integrated expression construct was selected and cultivated on a rotary shaking table in 500 mL baffled Erlenmeyer flasks each containing 100 ml yeast extract-based media. The clone was cultivated for 5 days at 30° C. The enzyme containing supernatants were harvested and the enzyme purified as described in Example 5.

Example 3: Purification of Wild Type GH5 Polypeptide from the Natural Opitutaceae Strain The Opitutaceae strain was cultivated on a rotary shaking table in 500 mL baffled Erlenmeyer flasks each containing 100 ml mineral solution with 0.5% xanthan gum. The strain was cultivated for 20 days at 30° C. A total of 2.0 L supernatant was harvested by centrifugation and was filtered using a 0.2 μm bottle top filter (Nalgene Nunc). The broth was concentrated to 300 mL using ultra-filtration (Sartorius) with 30 kDa cut-off. Equal volume of 3.2 M ammonium sulphate in 40 mM Tris-HCl, pH 7.9 was slowly added with continuous stirring. The sample was filtered using Whatman glass filters (1.7 μm-0.7 μm) to remove larger particles. The sample was applied on a 20 mL Phenyl-sepharose high performance column (GE Healthcare) pre-equilibrated with 1.6 M ammonium sulphate in 20 mM Tris-HCl, pH 7.9 (equilibration buffer). Unbound protein was eluted by two column volumes of equilibration buffer. Elution was done by a 12 column volume linear gradient from 1.6 M to 0.0 M ammonium sulphate in 20 mM Tris-HCl, pH 7.9. A last elution step of 4 column volume with equilibration buffer was used to elute tightly bound protein. The absorbance at 280 nm was recorded during the entire purification. Protein containing fractions identified by the absorbance at 280 nm in the chromatogram were analyzed by SDS-PAGE (Nu-PAGE, Invitrogen). Fractions judged as pure were pooled. The sample was concentration from 30 to 4 mL using Macrosep ultra filtration device with 3 kDa cut-off (Pall). The protein concentration was determined by measuring the absorbance at 280 nm using the calculated extinction coefficient where 1 mg/mL equaled 1.89 absorbance units.

Example 4: Purification of Recombinant GH5 Polypeptide Produced in E. coli 200 mL lysed cells (grown as example 2a) were filtered through Fast PES 0.2 μm bottle-top filters to remove debris and unbroken cells. 200 mL of equilibration buffer (20 mM Tris-HCl, pH 7.5+500 mM NaCl) was added to the crude protein solution. A 20 mL HisPrep column loaded with $Ni^{2+}$ was equilibrated with equilibration buffer until a stable UV baseline was obtained. The absorbance at 280 nm was continuously monitored throughout the purification. Crude protein was loaded on the column using a flow rate of 4 mL/min. Unbound protein was removed by washing the column with equilibration buffer until a stable UV baseline was obtained. Elution was carried out by a two-step linear gradient using 20 mM Tris-HCl, pH 7.5+500 mM NaCl+500 mM Imidazole (elution buffer). First elution gradient was 10 column volumes 0 to 40% elution buffer followed by 4 column volumes from 40% to 100%. Peaks absorbing at 280 nm were analyzed by SDS-PAGE (NuPAGE, Invitrogen). Fractions containing protein with the correct apparent molecular weight were pooled. The pool was desalted and buffer exchanged using a Sephadex G-25 super fine desalting column equilibrated with 20 mM Tris-HCl, pH 8.0. The pool was applied on a 20 mL Source 15Q column pre-equilibrated with 20 mM Tris-HCl, pH 8.0. Unbound protein was washed out using 20 mM Tris-HCl, pH 8.0 until a stable UV baseline was obtained. Elution was done by a 10 column volume linear NaCl gradient from 0 to 500 mM NaCl in 20 mM Tris-HCl, pH 8.0. Protein containing fractions were analyzed by SDS-PAGE and fractions judged as pure were pooled. Protein concentration was measured using absorbance at 280 nm using a calculated extinction coefficient where 1 mg/mL corresponded to 1.86 absorbance units.

Example 5: Purification of Recombinant GH5 Polypeptide Produced in B. subtilis All His-tagged enzymes were purified by immobilized metal chromatography (IMAC) using $Ni^{2+}$ as the metal ion on 5 mL HisTrap Excel columns (GE Healthcare Life Sciences). The purification was done at pH 8 and the bound proteins were eluted with imidazole. The purity of the purified enzymes was checked by SDS-PAGE and the concentration of each enzyme determined by Abs 280 nm after a buffer exchange.

Example 6: Xanthan Degrading Activity of GH5 Polypeptide and Xanthan Lyase on Xanthan Gum by Measurement of Viscosity Reduction The viscosity reduction measurements were performed using the viscosity pressure assay described in WO2011/107472 and following the method described in WO2013167581. Results presented are the average of three measurements and are shown in table 1 and 2 below.

A sample size of was 400 μL was used. The hydrolysis conditions were as follows: 30° C., either 0.25% or 0.5% xanthan gum (XG) in 50 mM MES buffer+0.01% triton x-100 pH 7.0 or 100 mM CHES buffer+0.01% triton x-100 pH10. Enzyme was added upon thermal equilibration. Prior to use all enzymes were buffer changed to the MES buffer using NAP 5 columns (GE Healthcare).

The purified enzyme preparations of Example 5 were used for the analysis at a concentration of 31.25 mg/L.

TABLE 1

Viscosity measurements (Pa) of EXa (SEQ ID NO: 13) and/or Xanthan Lyase (SEQ ID NO: 21) on 0.5% xanthan gum at pH 7.

| | T = 0 minutes | T = 30 minutes | T = 1 hour | T = 2 hours | T = 3 hours | T = 4 hours |
|---|---|---|---|---|---|---|
| Water (control) | 430 ± 44 | 504 ± 50 | 470 ± 75 | 483 ± 86 | 466 ± 60 | 504 ± 82 |
| Xanthan gum (control) | 1703 ± 132 | 1738 ± 26 | 1837 ± 122 | 1803 ± 64 | 1739 ± 84 | 1757 ± 21 |
| Xanthan gum + EXa SEQ ID NO: 13 | 1586 ± 101 | 1154 ± 38 | 1270 ± 67 | 1230 ± 36 | 1156 ± 49 | 1184 ± 44 |
| Xanthan gum + XLa SEQ ID NO: 21 | 1963 ± 93 | 1884 ± 67 | 1890 ± 84 | 1840 ± 131 | 1886 ± 50 | 1950 ± 25 |
| Xanthan gum + EXa SEQ ID NO: 13 + XLa SEQ ID NO: 21 | 1370 ± 197 | 861 ± 23 | 973 ± 59 | 840 ± 62 | 916 ± 47 | 904 ± 79 |

The results presented above show that the GH5 polypeptide alone and in combination with xanthan lyase can degrade the xanthan gum present in the media at pH 7, thus leading to viscosity reduction. A synergistic effect is obtained with combination of GH5 and xanthan lyase.

TABLE 2

Viscosity measurements (Pa) of EXa (SEQ ID NO: 13) and/or Xanthan Lyase (SEQ ID NO: 23) on 0.5% xanthan gum at pH 10

| | T = 0 | T = 0.5 hours | T = 1 hours | T = 2 hours | T = 3.5 hours |
|---|---|---|---|---|---|
| Water | 370 ± 10 | 454 ± 15 | 519 ± 60 | 411 ± 29 | 554 ± 180 |
| Xanthan gum (XG) control | 1740 ± 151 | 1734 ± 21 | 1819 ± 67 | 1795 ± 29 | 1898 ± 75 |
| XG + EXa SEQ ID NO: 13 | 1676 ± 50 | 1324 ± 58 | 1223 ± 12 | 1251 ± 31 | 1318 ± 62 |
| XG + XLc SEQ ID NO: 23 | 2046 ± 112 | 1811 ± 82 | 1773 ± 64 | 1781 ± 92 | 1704 ± 67 |
| XG + EXa SEQ ID NO: 13 + XLc SEQ ID NO: 23 | 1573 ± 227 | 1057 ± 21 | 1153 ± 12 | 1161 ± 40 | 1188 ± 89 |

The results presented above show that the GH5 polypeptide in alone or combination with xanthan lyase can degrade the xanthan gum present in the media at pH 10, thus leading to viscosity reduction.

TABLE 3

Viscosity measurements (Pa) of EXa (SEQ ID NO: 13), EXd (SEQ ID NO: 18) and/or Xanthan Lyase (XLa, SEQ ID NO: 21) on 0.5% xanthan gum at pH 7.

| | T = 0 | T = 0.5 hours | T = 1 hours | T = 2 hours | T = 3 hours |
|---|---|---|---|---|---|
| Water control | 440 | 410 | 333 | 413 | 469 |
| Xanthan gum (XG) control | 1626 | 1590 | 1546 | 1566 | 1659 |
| XG + EXa SEQ ID NO: 13 | 1220 | 1080 | 1046 | 1040 | 1079 |
| XG + EXa SEQ ID NO: 13 + XLa SEQ ID NO: 21 | 1263 | 850 | 786 | 793 | 815 |
| XG + EXd SEQ ID NO: 18 | 1476 | 1406 | 1313 | 1283 | 1245 |
| XG + EXd SEQ ID NO: 18 + XLa SEQ ID NO: 21 | 1490 | 1056 | 1023 | 933 | 912 |

The results presented above show that the GH5 polypeptide alone and in combination with xanthan lyase can degrade the xanthan gum present in the media at pH 7, thus leading to viscosity reduction.

TABLE 4

Viscosity measurements (Pa) of EXa, EXb, EXc recombinantly expressed in E.coli (SEQ ID NO: 13; SEQ ID NO: 14, SEQ ID NO: 15) and/or Xanthan Lyase (XLb, SEQ ID NO: 22) on 0.5% xanthan gum at pH 7. T = 00 is before addition of enzyme and T = 0 is right after.

|  | T = 00 | T = 0 | T = 30 min | T = 1 hr | T = 2 hrs | T = 3 hrs | T = 4 hrs |
|---|---|---|---|---|---|---|---|
| Water | 541 ± 21 | 544 ± 119 | 519 ± 142 | 545 ± 70 | 399 ± 80 | 422 ± 114 | 326 ± 25 |
| Xanthan gum control | 1878 ± 20 | 1444 ± 15 | 1599 ± 91 | 1571 ± 64 | 1605 ± 38 | 1586 ± 40 | 1566 ± 32 |
| XG + XLb SEQ ID NO: 22 | 1898 ± 26 | 1511 ± 12 | 1522 ± 56 | 1505 ± 20 | 1579 ± 80 | 1516 ± 21 | 1559 ± 38 |
| XG + EXb SEQ ID NO: 14 | 1884 ± 31 | 1281 ± 55 | 1202 ± 120 | 1145 ± 52 | 1132 ± 70 | 1096 ± 60 | 1116 ± 114 |
| XG + EXc SEQ ID NO: 15 | 1931 ± 45 | 1444 ± 80 | 1122 ± 36 | 1108 ± 42 | 1105 ± 45 | 1019 ± 10 | 1059 ± 15 |
| XG + EXa SEQ ID NO: 13 | 1891 ± 12 | 1441 ± 38 | 1102 ± 17 | 1051 ± 25 | 1005 ± 6 | 969 ± 26 | 1036 ± 25 |
| XG + EXb SEQ ID NO: 14 + XLb SEQ ID NO: 22 | 1918 ± 61 | 1121 ± 6 | 862 ± 17 | 731 ± 31 | 689 ± 25 | 652 ± 40 | 576 ± 40 |
| XG + EXc SEQ ID NO: 15 + XLb SEQ ID NO: 22 | 1911± | 1111± | 935± | 848± | 832± | 822± | 789± |
| XG + EXa SEQ ID NO: 13 + XLb SEQ ID NO: 22 | 1934 ± 31 | 1198 ± 36 | 855 ± 40 | 831 ± 40 | 785 ± 23 | 909 ± 26 | 819 ± 64 |

The results presented above show that the GH5 polypeptides EXa, EXb and EXc alone and in combination with xanthan lyase can degrade the xanthan gum present in the media at pH 7, thus leading to viscosity reduction. A synergistic effect is obtained with combination of GH5 polypeptide and xanthan lyase.

TABLE 5

Viscosity measurements (Pa) of EXa, recombinantly expressed in E. coli (SEQ ID NO: 13) and EXb and EXc recombinantly expressed in B. subtilis (SEQ ID NO: 16 and SEQ ID NO: 17) and/or Xanthan Lyase (XLb, SEQ ID NO: 22) on 0.5% xanthan gum at pH 7. T = 00 is before addition of enzyme and T = 0 is right after.

|  | T = 00 | T = 0 | T = 30 min | T = 1 hour | T = 2 hours | T = 3 hours | T = 4 hours |
|---|---|---|---|---|---|---|---|
| Water | 441 ± 25 | 421 ± 40 | 646 ± 44 | 535 ± 59 | 599 ± 74 | 492 ± 15 | 494 ± 32 |
| Xanthan gum(XG) | 2027 ± 23 | 1707 ± 35 | 1949 ± 59 | 1785 ± 116 | 1746 ± 75 | 1726 ± 10 | 1867 ± 6 |
| XG + EXa SEQ ID NO: 13 | 2054 ± 44 | 1514 ± 17 | 1299 ± 21 | 1112 ± 57 | 1089 ± 45 | 1046 ± 0 | 1027 ± 6 |
| XG + EXb SEQ ID NO: 16 | 2067 ± 15 | 1527 ± 81 | 1393 ± 12 | 1229 ± 53 | 1159 ± 12 | 1136 ± 0 | 1134 ± 6 |
| XG + EXc SEQ ID NO: 17 | 2061 ± 31 | 1501 ± 55 | 1416 ± 44 | 1175 ± 6 | 1183 ± 78 | 1169 ± 40 | 1147 ± 15 |
| XG + EXa SEQ ID NO: 13 + XLb SEQ ID NO: 22 | 2061 ± 6 | 1274 ± 17 | 1063 ± 47 | 812 ± 59 | 769 ± 46 | 729 ± 15 | 671 ± 26 |
| XG + EXb SEQ ID NO: 20 + XLb SEQ ID NO: 22 | 2074 ± 26 | 1411 ± 65 | 1079 ± 15 | 945 ± 92 | 809 ± 12 | 796 ± 10 | 781 ± 10 |
| XG + EXc SEQ ID NO: 17 + XLb SEQ ID NO: 22 | 2094 ± 30 | 1491 ± 25 | 1166 ± 0 | 959 ± 46 | 889 ± 40 | 846 ± 0 | 847 ± 57 |
| XG + XLb SEQ ID NO: 22 | 2097 ± 49 | 1794 ± 62 | 1863 ± 23 | 1685 ± 15 | 1653 ± 10 | 1679 ± 6 | 1667 ± 29 |
| XG + EXa SEQ ID NO: 13 + XLa SEQ ID NO: 21 | 2131 ± 15 | 1227 ± 81 | 1143 ± 81 | 789 ± 62 | 739 ± 25 | 716 ± 44 | 677 ± 55 |
| XG + EXb SEQ ID NO: 16 + XLa SEQ ID NO: 21 | 2104 ± 79 | 1324 ± 17 | 1096 ± 44 | 795 ± 31 | 803 ± 26 | 792 ± 21 | 767 ± 12 |

TABLE 5-continued

Viscosity measurements (Pa) of EXa, recombinantly expressed in *E. coli* (SEQ ID NO: 13) and EXb and EXc recombinantly expressed in *B. subtilis* (SEQ ID NO: 16 and SEQ ID NO: 17) and/or Xanthan Lyase (XLb, SEQ ID NO: 22) on 0.5% xanthan gum at pH 7. T = 00 is before addition of enzyme and T = 0 is right after.

| | T = 00 | T = 0 | T = 30 min | T = 1 hour | T = 2 hours | T = 3 hours | T = 4 hours |
|---|---|---|---|---|---|---|---|
| XG + EXc SEQ ID NO: 17 + XLa SEQ ID NO: 21 | 2107 ± 12 | 1241 ± 50 | 1163 ± 32 | 802 ± 15 | 826 ± 15 | 846 ± 0 | 894 ± 15 |
| XG + XLa SEQ ID NO: 21 | 2134 ± 20 | 1741 ± 57 | 1933 ± 29 | 1639 ± 30 | 1659 ± 23 | 1666 ± 17 | 1637 ± 12 |

The results presented above show that the GH5 polypeptides EXa, EXb and EXc alone and in combination with xanthan lyase can degrade the xanthan gum present in the media at pH 7, thus leading to viscosity reduction. A synergistic effect is obtained with combination of GH5 polypeptide and xanthan lyase.

TABLE 6

Viscosity measurements (Pa) of EXa, EXb, EXc recombinantly expressed in *E. coli* (SEQ ID NO: 13; SEQ ID NO: 14 or SEQ ID NO: 15) and/or Xanthan Lyase (XLc, SEQ ID NO: 23 or SEQ ID NO: 24) on 0.5% xanthan gum at pH 10. T = 00 is before addition of enzyme and T = 0 is right after.

| | T = 00 | T = 0 | T = 30' | T = 1 hr | T = 2 hrs | T = 3 hrs |
|---|---|---|---|---|---|---|
| Water | 429 ± 66 | 502 ± 110 | 504 ± 50 | 434 ± 29 | 478 ± 42 | 479 ± 26 |
| Xanthan gum (XG) | 1932 ± 31 | 1485 ± 81 | 1678 ± 12 | 1641 ± 70 | 1642 ± 38 | 1592 ± 92 |
| XG + EXa SEQ ID NO: 13 | 1992 ± 138 | 1332 ± 6 | 1254 ± 21 | 1147 ± 51 | 1192 ± 35 | 1215 ± 31 |
| XG + EXb SEQ ID NO: 14 | 1989 ± 85 | 1415 ± 50 | 1351 ± 66 | 1321 ± 17 | 1358 ± 51 | 1252 ± 21 |
| XG + EXc SEQ ID NO: 17 | 1892 ± 45 | 1442 ± 100 | 1408 ± 21 | 1341 ± 50 | 1332 ± 31 | 1262 ± 51 |
| XG + EXa SEQ ID NO: 13 + XLc SEQ ID NO: 23 | 1899 ± 69 | 1429 ± 62 | 1084 ± 76 | 1131 ± 17 | 1092 ± 25 | 1112 ± 40 |
| XG + EXb SEQ ID NO: 14 + XLc SEQ ID NO: 23 | 2019 ± 62 | 1465 ± 132 | 1144 ± 23 | 1121 ± 53 | 1108 ± 81 | 1012 ± 59 |
| XG + EXc SEQ ID NO: 15 + XLc SEQ ID NO: 23 | 2085 ± 80 | 1602 ± 38 | 1344 ± 15 | 1321 ± 10 | 1262 ± 55 | 1319 ± 10 |
| XG + XLc SEQ ID NO: 23 | 2005 ± 47 | 1702 ± 75 | 1588 ± 6 | 1524 ± 67 | 1588 ± 60 | 1569 ± 36 |
| XG + EXa SEQ ID NO: 13 + XLd SEQ ID NO: 24 | 1959 ± 72 | 1462 ± 110 | 1158 ± 38 | 1144 ± 40 | 1148 ± 72 | 1005 ± 45 |
| XG + EXb SEQ ID NO: 14 + XLd SEQ ID NO: 24 | 1975 ± 25 | 1442 ± 35 | 1211 ± 26 | 1177 ± 15 | 1192 ± 72 | 1182 ± 67 |
| XG + EXc SEQ ID NO: 15 + XLd SEQ ID NO: 24 | 1925 ± 133 | 1422 ± 95 | 1238 ± 12 | 1274 ± 58 | 1208 ± 81 | 1215 ± 67 |
| XG + XLd SEQ ID NO: 24 | 1839 ± 40 | 1525 ± 61 | 1488 ± 21 | 1447 ± 42 | 1432 ± 15 | 1425 ± 76 |

The results presented above show that the GH5 polypeptides GH5, EXb and EXc in combination with xanthan lyase can degrade the xanthan gum present in the media at pH 10, thus leading to viscosity reduction.

TABLE 7

Viscosity measurements (Pa) of GH5 polypeptide purified from supernatant of the Opitutaceae sp strain and/or Xanthan Lyase (XLa, SEQ ID NO: 21) on 0.25% xanthan gum at pH 7

| | T = 0 | T = 0.5 hour | T = 1 hour | T = 2 hours | T = 3 hours |
|---|---|---|---|---|---|
| Water | 471 ± 99 | 390 ± 46 | 423 ± 61 | 433 ± 64 | 438 ± 36 |
| Xanthan gum (XG) | 898 ± 12 | 880 ± 40 | 900 ± 17 | 820 ± 40 | 908 ± 50 |
| XG + EXa SEQ ID NO: 1 | 856 ± 34 | 743 ± 46 | 723 ± 34 | 672 ± 38 | 644 ± 55 |
| XG + XLa SEQ ID NO: 21 | 908 ± 29 | 865 ± 22 | 860 ± 35 | 857 ± 32 | 856 ± 61 |
| XG + EXa SEQ ID NO: 1 + XLa SEQ ID NO: 21 | 800 ± 28 | 597 ± 30 | 612 ± 31 | 577 ± 45 | 648 ± 89 |

Example 8: Xanthan Degrading Activity of GH5 Polypeptide and Xanthan Lyase on Xanthan Gum by Measurement of Viscosity Reduction The viscosity measurements were performed using the viscosity pressure assay described in WO2011/107472. 150 µL of each 1 mL hydrolysis or control was the sample size. Results presented are the average of four measurements and are shown in table 8 and 9 below.

Modified xanthan gum was prepared by an adaption of Nankai et al. 1999. "Microbial system for polysaccharide depolymerization: enzymatic route for xanthan depolymerization by *Bacillus* sp strain GL1." Applied and Environmental Microbiology 65(6): 2520-2526.

2.5 g of xanthan gum (CP Kelco) was wetted with 5 mL of 96% ethanol in a 2 L beaker. 500 mL of 100 mM ACES buffer pH 7.00 was added and the solution stirred at ambient temperature for 2 h. 250 µl of xanthan lyase (*Bacillus* sp., Megazyme) was added and the solution incubated for 20 h at 50° C. The sample was then cooled by placing the beaker on ice. After hydrolysis was 1400 mL of ice cold 96% ethanol was added to the 500 mL sample, under stirring. Precipitation occurs, and after approximately 5 min the ethanol was decanted removing the pyruvated mannose residues. The sample was vacuum filtered and transferred to a glass plate. The glasses were dried at 50° C. for 20 h. The sample was collected, weighed, and grinded.

The hydrolysis conditions were as follows: 40° C., 0.35% xanthan gum (XG) in 50 mM HEPES buffer+0.01% triton X-100 pH 7.0. The modified xanthan gum powder (mXG) was prepared as described above and a 0.7% solution was prepared using the same procedure as outlined for XG. Enzyme was added upon thermal equilibration. The initial viscosity is measured prior to enzyme addition, after thermal equilibration. Controls are the same with buffer added instead of enzyme. Buffer was monitored to determine the ultimate end point of a total hydrolysis.

TABLE 8

Viscosity measurements (Pa). EXc SEQ ID NO: 17 and XLb (SEQ ID NO: 22). Each enzyme dosed in 1.5 ppm. pH 7.0

| Time (Minutes) | 0 | 15 | 30 | 45 | 60 | 75 | 90 |
|---|---|---|---|---|---|---|---|
| Buffer 50 mM HEPES Control | 645 | 610 | 521 | 502 | 620 | 632 | 600 |
| Xanthan Gum + Buffer Control | 2140 | 2075 | 1948 | 2092 | 2033 | 2077 | 2005 |

TABLE 8-continued

Viscosity measurements (Pa). EXc SEQ ID NO: 17 and XLb (SEQ ID NO: 22). Each enzyme dosed in 1.5 ppm. pH 7.0

| Time (Minutes) | 0 | 15 | 30 | 45 | 60 | 75 | 90 |
|---|---|---|---|---|---|---|---|
| Xanthan Gum + EXc | 2120 | 1295 | 991 | 957 | 935 | 1112 | 917 |
| Xanthan Gum + EXc + Xanthan Lyase | 1977 | 808 | 811 | 837 | 773 | 807 | 777 |
| Xanthan Gum + Xanthan lyase | 1972 | 1853 | 1838 | 1802 | 1750 | 1737 | 1677 |
| Modified Xanthan Gum + Buffer Control | 2262 | 2100 | 2143 | 2134 | 2118 | 2150 | 2097 |
| Modified Xanthan Gum + EXc | 2217 | 1225 | 1173 | 1157 | 1130 | 1155 | 1130 |

Example 9: Wash Performance of GH5 Polypeptide and Xanthan Lyase

The wash performance of the GH5 enzyme was assessed in laundry wash experiments using a Mini wash assay, which is a test method where soiled textile is continuously lifted up and down into the test solution and subsequently rinsed. The wash experiment was conducted under the experimental conditions specified in Table 10.

The textiles were subsequently air-dried and the wash performance was measured as the brightness of the color of the textiles. Brightness can be expressed as the Remission (R), which is a measure for the light reflected or emitted from the test material when illuminated with white light. The Remission (R) of the textiles was measured at 460 nm using a Zeiss MCS 521 VIS spectrophotometer. The measurements were done according to the manufacturer's protocol.

The performance of the new enzyme (combination) was compared to the performance of detergent alone (blank). An enzyme (combination) is considered to exhibit improved wash performance, if it performs better than the detergent alone (i.e. $R_{ENZYME} > R_{BLANK}$) (see Table 13 and 14).

TABLE 10

Experimental setup of Mini wash assay

| | |
|---|---|
| Detergent | Liquid Model detergent A or Model detergent T (see Table 11 and 12) |
| Detergent dose | 3.33 g/l |
| pH | "as is" in the current detergent solution and was not adjusted |
| Water hardness | 16°dH, adjusted by adding $CaCl_2*2H_2O$, $MgCl_2*6H_2O$ and $NaHCO_3$ (5:1:3) to milli-Q water. |
| Enzymes | EXc (SEQ ID NO: 17), xanthan lyase (XLb, SEQ ID NO: 22 or XLc SEQ ID NO: 23) |
| Enzyme dosage | Dosage of GH5: 0.05 mg EP/L (enzyme protein), 0.10 mg EP/L, 0.2 mg EP/L, 0.5 mg EP/L, 1.0 mg EP/L; experiments with combinations of GH5 and XL were conducted with a fixed concentration of 1.0 mg EP/L XL |
| Volume of test solution | 50 ml |
| Test material | Xanthan Gum with carbon black DN-31D textile swatches (23 × 3 cm). The test material was obtained from Center for Testmaterials BV, P.O. Box 120, 3133 KT Vlaardingen, the Netherlands, and WFK Testgewebe GmbH, Christenfeld 10, D-41379 Bruggen, Germany |
| Temperature | 40° C. |
| Wash time | 30 min |
| Rinse time | 5 min |
| Test system | Soiled textile continuously lifted up and down into the test solutions, 50 times per minute (up-time 0.4 sec, down-time 0.4 sec, lift time 0.4 sec). The test solutions are kept in 125 ml glass beakers. After wash of the textiles are continuously lifted up and down into tap water, 50 times per minute (up-time 0.4 sec, down-time 0.4 sec, lift time 0.4 sec). |

TABLE 11

Composition of Model Detergent A (Liquid)[1)]

| Detergent ingredients | Wt % |
|---|---|
| Linear alkylbenzenesulfonic acid (LAS) (Marlon AS3) | 13 |
| Sodium alkyl(C12)ether sulfate (AEOS) (STEOL CS-370 E) | 10 |
| Coco soap (Radiacid 631) | 2.75 |
| Soy soap (Edenor SJ) | 2.75 |
| Alcohol ethoxylate (AEO) (Bio-Soft N25-7) | 11 |
| Sodium hydroxide | 2 |
| Ethanol | 3 |
| Propane-1,2-diol (MPG) | 6 |
| Glycerol | 2 |
| Triethanolamine (TEA) | 3 |
| Sodium formate | 1 |
| Sodium citrate | 2 |
| Diethylenetriaminepentakis(methylenephosphonic acid) (DTMPA) | 0.2 |
| Polycarboxylate polymer (PCA) (Sokalan CP-5) | 0.2 |
| Water | Up to 100 |

[1)]The pH of the detergent was adjusted to pH 8 with sodium hydroxide or citric acid.

TABLE 12

Composition of Model detergent T (powder)

| Detergent ingredients | Wt % |
|---|---|
| LAS, sodium salt | 11.72 |
| AS, sodium salt | 2.0 |
| Soap, sodium salt | 2.15 |
| AEO | 3.0 |
| Soda ash | 14.98 |
| Hydrous sodium silicate | 3.12 |
| Zeolite A | 18.75 |
| HEDP-Na4 | 0.15 |
| Sodium citrate | 2.0 |
| PCA, copoly(acrylic acid/maleic acid), sodium salt | 1.65 |
| SRP | 0.5 |
| Sodium sulfate | 13.53 |
| Sodium percarbonate | 22.20 |
| TAED | 3.25 |
| Foam regulator | 1.0 |

TABLE 13

Remission (R) values obtained in Mini Wash using EXc with and without xanthan lyase (XLb) in liquid model A detergent

| Enzyme dosage | No enzyme | EXc | EXc + xanthan lyase |
|---|---|---|---|
| 0.05 mg EP/L | 29.5 | 32.8 | 35.1 |
| 0.1 mg EP/L | 29.5 | 33.6 | 35.4 |
| 0.2 mg EP/L | 29.5 | 34.3 | 35.9 |
| 0.5 mg EP/L | 29.5 | 35.1 | 36.7 |
| 1.0 mg EP/L | 29.5 | 35.4 | 37.3 |

TABLE 14

Remission (R) values obtained in Mini Wash using EXc with and without Xanthan Lyase (XLc) in powder model T detergent

| Enzyme dosage | No enzyme | EXc | EXc + xanthan lyase |
|---|---|---|---|
| 0.05 mg EP/L | 29.8 | 29.7 | 29.7 |
| 0.1 mg EP/L | 29.8 | 29.8 | 29.8 |
| 0.2 mg EP/L | 29.8 | 30.0 | 30.0 |
| 0.5 mg EP/L | 29.8 | 30.6 | 30.9 |
| 1.0 mg EP/L | 29.8 | 31.0 | 31.2 |

Example 10: Wash Performance of Combinations of a GH5 Polypeptide and Xanthan Lyase was Tested on Specific Stains The wash performance of variants in liquid and powder detergents was determined by using the following standardized stains, all obtainable from CFT (Center for Test materials) B.V., Vlaardingen, Netherlands:
A: Fluid make-up: product no. PCS17
B: Fluid make-up: product no. CS17

For the tests in liquid detergents, a liquid washing agent with the following composition was used as base formulation (all values in weight percent): 0 to 0.5% xanthan gum, 0.2 to 0.4% antifoaming agent, 6 to 7% glycerol, 0.3 to 0.5% ethanol, 0 to 7% FAEOS (fatty alcohol ether sulfate), 10 to 28% nonionic surfactants, 0.5-1% boric acid, 1 to 2% sodium citrate (dihydrate), 2 to 4% soda, 0 to 16% coconut fatty acid, 0.5% HEDP (1-hydroxyethane-(1,1-diphosphonic acid)), 0 to 0.4% PVP (polyvinylpyrrolidone), 0 to 0.05% optical brighteners, 0 to 0.001% dye, remainder deionized water.

Based on this base formulation, detergent was prepared by adding the respective enzyme combination as indicated in table 15. As a reference, the detergent composition without addition of the enzyme combinations was used.

The dosing ratio of the liquid washing agent was 4.7 grams per liter of washing liquor and the washing procedure was performed for 60 minutes at a temperature of 40° C., the water having a water hardness between 15.5 and 16.5° (German degrees of hardness).

For the tests in solid detergents, a European premium detergent was used as base formulation.

The whiteness, i.e. the brightening of the stains, was determined photometrically as an indication of wash performance. A Minolta CM508d spectrometer device was used, which was calibrated beforehand using a white standard provided with the unit.

The results obtained are the difference values between the remission units obtained with the detergents and the remission units obtained with the detergent containing the enzyme combinations. A positive value therefore indicates an improved wash performance due to the enzyme combinations present in the detergent. It is evident from table 15 that enzyme combinations as contemplated herein show improved wash performance.

TABLE 15

Wash performance in liquid detergent

| Enzyme combination | | A | B |
|---|---|---|---|
| XLb SEQ ID NO: 22 + EXc SEQ ID NO: 17 | Diff | 3.3 | 6.4 |
| | HSD | 2.4 | 1.2 |

TABLE 16

Wash performance in solid detergent

| Enzyme combination | | B |
|---|---|---|
| XLb SEQ ID NO: 22 + EXc SEQ ID NO: 17 | Diff | 1.9 |
| | HSD | 1.2 |

Example 11: Wash Performance of GH5 Polypeptides with and without Xanthan Lyase In this example wash performance of GH5 polypeptides was evaluated in a liquid model detergent A washed in the Automatic Mechanical Stress Assay (AMSA) at 20° C. or 40° C. The wash performance of the enzymes was evaluated either alone or in combination with a Xanthan Lyase. The wash conditions used are specified in Table 17 below.

TABLE 17

Wash conditions used in the example 11:

| | |
|---|---|
| Detergent | Liquid model detergent A |
| Detergent conc. | 3.3 g/L |
| pH | "as is" in the current detergent solution and was not adjusted |
| Temperature | 20° C. or 40° C. |
| Dosages in AMSA-plate | 140 μL detergent per slot; 20 μL enzyme per slot |
| Water hardness | 16°dH, adjusted by adding $CaCl_2*2H_2O$, $MgCl_2*6H_2O$ and $NaHCO_3$ (5:1:3) to milli-Q water |
| Enzymes | EXb (SEQ ID NO: 16); EXc (SEQ ID NO: 17), xanthan lyase (XLb, SEQ ID NO: 22) |
| Enzyme dosage | EXb and EXc concentrations: 0.7, 1.5, 20, 125 ppb XLb concentration: 400 ppb |
| Test solution volume | 160 micro L |
| Wash time | 20 minutes |
| Stain/swatch | Mayonnaise with carbon black C-S-05 S from CFT, Center for Testmaterials BV. |

The enzyme and wash liquid were dosed into the AMSA plate and washed according to conditions listed in Table 17. After wash the fabric was flushed in tap water and air-dried.

The performance of the enzyme was subsequently measured as the brightness of the colour of the textile samples. Brightness was measured as the intensity of the light reflected from the textile sample when illuminated with white light. Intensity was measured with a professional flatbed scanner EPSON EXPRESSION 10000XL with specially designed software that extracted the intensity value from the scanned imagine through standard vector calculations.

The performance of the enzyme (or combination of enzymes) was compared to the performance of detergent alone (blank) or detergent with the Xanthan lyase (XL). An enzyme (or combination of enzymes) was considered to exhibit improved wash performance if it performed better than the detergent alone (i.e., $R_{ENZYME} > R_{BLANK}$) (see Tables 18, 19, 20 and 21).

TABLE 18

Intensity and delta intensity of GH5 polypeptides EXb (SEQ ID NO: 16) and EXc (SEQ ID NO: 17) tested in AMSA at 20° C. in model detergent A.

| | Intensity | | | | Delta intensity | | | |
|---|---|---|---|---|---|---|---|---|
| | Concentration [ppb] | | | | | | | |
| | 0.7 | 1.5 | 20 | 125 | 0.7 | 1.5 | 20 | 125 |
| Blank | 210.4 | 210.4 | 210.4 | 210.4 | | | | |
| EXb (SEQ ID NO: 16) | 210.8 | 212.8 | 217.2 | 217.8 | 0.4 | 2.4 | 6.8 | 7.5 |
| EXc (SEQ ID NO: 17) | 212.0 | 214.4 | 216.5 | 218.4 | 1.6 | 4.1 | 6.2 | 8.0 |

TABLE 19

Intensity and delta intensity of GH5 polypeptides EXb (SEQ ID NO: 16) and EXc (SEQ ID NO: 17) tested in AMSA at 40° C. in model detergent A.

| | Intensity | | | | Delta intensity | | | |
|---|---|---|---|---|---|---|---|---|
| | Concentration [ppb] | | | | | | | |
| | 0.7 | 1.5 | 20 | 125 | 0.7 | 1.5 | 20 | 125 |
| Blank | 220.0 | 220.0 | 220.0 | 220.0 | | | | |
| EXb (SEQ ID NO: 16) | 221.9 | 222.9 | 229.4 | 230.2 | 1.9 | 3.0 | 9.4 | 10.2 |
| EXc (SEQ ID NO: 17) | 223.2 | 225.4 | 228.3 | 229.0 | 3.3 | 5.4 | 8.3 | 9.0 |

TABLE 20

Intensity and delta intensity of GH5 polypeptides EXb (SEQ ID NO: 16) and EXc (SEQ ID NO: 17) with Xanthan lyase (XLb (SEQ ID NO: 22) tested in AMSA at 20° C. in model detergent A.

| | Intensity | | | | Delta intensity | | | |
|---|---|---|---|---|---|---|---|---|
| | Concentration [ppb] | | | | | | | |
| | 0.7 | 1.5 | 20 | 125 | 0.7 | 1.5 | 20 | 125 |
| Blank with XLb (SEQ ID NO: 22) | 214.0 | 214.0 | 214.0 | 214.0 | | | | |
| EXb (SEQ ID NO: 16 with XLb (SEQ ID NO: 22) | 213.0 | 215.3 | 220.4 | 223.7 | −1.0 | 1.3 | 6.4 | 9.7 |
| EXc (SEQ ID NO: 17) with XLb (SEQ ID NO: 22) | 212.4 | 215.1 | 220.2 | 221.4 | −1.6 | 1.1 | 6.2 | 7.4 |

TABLE 21

Intensity and delta intensity of GH5 polypeptides EXb (SEQ ID NO: 16) and EXc (SEQ ID NO: 17) with Xanthan lyase (XLb (SEQ ID NO: 22) tested in AMSA at 40° C. in model detergent A.

| | Intensity | | | | Delta intensity | | | |
|---|---|---|---|---|---|---|---|---|
| | Concentration [ppb] | | | | | | | |
| | 0.7 | 1.5 | 20 | 125 | 0.7 | 1.5 | 20 | 125 |
| Blank with XLb (SEQ ID NO: 22) | 220.6 | 220.6 | 220.6 | 220.6 | | | | |
| EXb (SEQ ID NO: 16 with XLb (SEQ ID NO: 22) | 222.0 | 225.0 | 231.0 | 232.6 | 1.3 | 4.4 | 10.3 | 12.0 |
| EXc (SEQ ID NO: 17) with XLb (SEQ ID NO: 22) | 222.3 | 223.9 | 230.1 | 231.5 | 1.7 | 3.2 | 9.5 | 10.9 |

The results in above tables show that the GH5 polypeptides, e.g., EXb and EXc, have an improved wash performance both when evaluated alone or in combination with the Xanthan Lyase, e.g., XLb.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A detergent composition comprising a polypeptide of glycosyl hydrolase family 5 having xanthan degrading activity, wherein the polypeptide is selected from the group of:
   (a) a polypeptide having at least about 90% sequence identity to the mature polypeptide of SEQ ID NO: 6 and comprising a substitution, deletion, and/or insertion at one or more positions as compared to the mature polypeptide of SEQ ID NO: 6;
   (b) a polypeptide encoded by a polynucleotide that hybridizes with (i) a polypeptide coding sequence that has at least about 90% sequence identity to the mature polypeptide coding sequence of SEQ ID NO: 5 and that comprises a substitution, deletion, and/or insertion at one or more positions as compared to the mature polypeptide coding sequence of SEQ ID NO: 5 or (ii) the full-length complement of (i), wherein the polynucleotide has at least about 90% sequence identity to the mature polypeptide coding sequence of SEQ ID NO: 5 and comprises a substitution, deletion, and/or insertion at one or more positions as compared to the mature polypeptide coding sequence of SEQ ID NO: 5;

(c) a polypeptide encoded by a polynucleotide that has at least about 90% sequence identity to the mature polypeptide coding sequence of SEQ ID NO: 5 and that comprises a substitution deletion, and/or insertion at one or more positions as compared to the mature polypeptide coding sequence of SEQ ID NO: 5;

(d) a variant of the mature polypeptide of SEQ ID NO: 6 comprising a substitution, deletion, and/or insertion at one or more positions, wherein the variant has at least about 90% sequence identity to the mature polypeptide of SEQ ID NO: 6;

(e) a fragment of the polypeptide of (a), (b), (c), or (d) that has at least about 90% sequence identity to the mature polypeptide of SEQ ID NO: 6 and that comprises a substitution, deletion, and/or insertion at one or more positions as compared to the mature polypeptide of SEQ ID NO: 6; and (f) a polypeptide comprising the polypeptide of (a), (b), (c), (d), or (e) and a N-terminal and/or C-terminal His-tag.

2. A detergent composition comprising a polypeptide of glycosyl hydrolase family 5 having xanthan degrading activity, wherein the polypeptide is selected from the group of:

(a) a polypeptide having at least about 90% sequence identity to the mature polypeptide of SEQ ID NO: 2 and comprising a substitution, deletion, and/or insertion at one or more positions as compared to the mature polypeptide of SEQ ID NO: 2;

(b) a polypeptide encoded by a polynucleotide that hybridizes with (i) a polypeptide coding sequence that has at least about 90% sequence identity to the mature polypeptide coding sequence of SEQ ID NO: 1 and that comprises a substitution, deletion, and/or insertion at one or more positions as compared to the mature polypeptide coding sequence of SEQ ID NO: 1 or (ii) the full-length complement of (i), wherein the polynucleotide has at least about 90% sequence identity to the mature polypeptide coding sequence of SEQ ID NO: 1 and comprises a substitution, deletion, and/or insertion at one or more positions as compared to the mature polypeptide coding sequence of SEQ ID NO: 1;

(c) a polypeptide encoded by a polynucleotide that has at least about 90% sequence identity to the mature polypeptide coding sequence of SEQ ID NO: 1 and that comprises a substitution, deletion, and/or insertion at one or more positions as compared to the mature polypeptide coding sequence of SEQ ID NO: 1;

(d) a variant of the mature polypeptide of SEQ ID NO: 2 comprising a substitution, deletion, and/or insertion at one or more positions, wherein the variant has at least about 90% sequence identity to the mature polypeptide of SEQ ID NO: 2;

(e) a fragment of the polypeptide of (a), (b), (c), or (d) that has at least about 90% sequence identity to the mature polypeptide of SEQ ID NO: 2 and that comprises a substitution, deletion, and/or insertion at one or more positions as compared to the mature polypeptide of SEQ ID NO: 2; and (f) a polypeptide comprising the polypeptide of (a), (b), (c), (d), or (e) and a N-terminal and/or C-terminal His-tag.

3. A detergent composition comprising a polypeptide of glycosyl hydrolase family 5 having xanthan degrading activity, wherein the polypeptide is selected from the group of:

(a) a polypeptide having at least about 90% sequence identity to the mature polypeptide of SEQ ID NO: 4 and comprising a substitution, deletion, and/or insertion at one or more positions as compared to the mature polypeptide of SEQ ID NO: 4;

(b) a polypeptide encoded by a polynucleotide that hybridizes with (i) a polypeptide coding sequence that has at least about 90% sequence identity to the mature polypeptide coding sequence of SEQ ID NO: 3 and that comprises a substitution, deletion, and/or insertion at one or more positions as compared to the mature polypeptide coding sequence of SEQ ID NO: 3 or (ii) the full-length complement of (i), wherein the polynucleotide has at least about 90% sequence identity to the mature polypeptide coding sequence of SEQ ID NO: 3 and comprises a substitution, deletion, and/or insertion at one or more positions as compared to the mature polypeptide coding sequence of SEQ ID NO: 3;

(c) a polypeptide encoded by a polynucleotide that has at least about 90% sequence identity to the mature polypeptide coding sequence of SEQ ID NO: 3 and that comprises a substitution, deletion, and/or insertion at one or more positions as compared to the mature polypeptide coding sequence of SEQ ID NO: 3;

(d) a variant of the mature polypeptide of SEQ ID NO: 4 comprising a substitution, deletion, and/or insertion at one or more positions, wherein the variant has at least about 90% sequence identity to the mature polypeptide of SEQ ID NO: 4;

(e) a fragment of the polypeptide of (a), (b), (c), or (d) that has at least about 90% sequence identity to the mature polypeptide of SEQ ID NO: 4 and that comprises a substitution, deletion, and/or insertion at one or more positions as compared to the mature polypeptide of SEQ ID NO: 4; and (f) a polypeptide comprising the polypeptide of (a), (b), (c), (d), or (e) and a N-terminal and/or C-terminal His-tag.

4. The detergent composition of claim 1, wherein the polypeptide has at least about 90% sequence identity to the mature polypeptide of SEQ ID NO: 6 and comprises a substitution, deletion, and/or insertion at one or more positions as compared to the mature polypeptide of SEQ ID NO: 6.

5. The detergent composition of claim 1, wherein the polypeptide is encoded by a polynucleotide that hybridizes with (i) the polypeptide coding sequence that has at least about 90% sequence identity to the mature polypeptide coding sequence of SEQ ID NO: 5 and that comprises a substitution, deletion, and/or insertion at one or more positions as compared to the mature polypeptide coding sequence of SEQ ID NO: 1, or, (ii) the full-length complement of (i), wherein the polynucleotide has at least about 90% sequence identity to the mature polypeptide coding sequence of SEQ ID NO: 5 and comprises a substitution, deletion, and/or insertion at one or more positions as compared to the mature polypeptide coding sequence of SEQ ID NO: 5.

6. The detergent composition of claim 1, wherein the polypeptide is encoded by a polynucleotide that has at least about 90% sequence identity to the mature polypeptide coding sequence of SEQ ID NO: 5 and that comprises a substitution, deletion, and/or insertion at one or more positions as compared to the mature polypeptide coding sequence of SEQ ID NO: 5.

7. The detergent composition of claim 1, wherein the polypeptide is a variant of the mature polypeptide of SEQ ID NO: 6 comprising a substitution, deletion, and/or insertion at one or more positions, and wherein the variant has at least about 90% sequence identity to the mature polypeptide of SEQ ID NO: 6.

8. The detergent composition of claim 1, wherein the polypeptide is a fragment of SEQ ID NO: 6 that has at least about 90% sequence identity to the mature polypeptide of SEQ ID NO: 6 and that comprises a substitution, deletion, and/or insertion at one or more positions as compared to the mature polypeptide of SEQ ID NO: 6.

9. The detergent composition of claim 1, further comprising a polypeptide having xanthan lyase activity.

10. The detergent composition of claim 9, wherein the polypeptide having xanthan lyase activity is a polypeptide having the amino acid sequence of any one of SEQ ID NOS: 21, 22, 23 or 24.

11. The detergent composition according to claim 1, wherein the composition is in form of a bar, a homogenous tablet, a tablet having two or more layers, a pouch having one or more compartments, a regular or compact powder, a granule, a paste, a gel, or a regular, compact or concentrated liquid.

12. The detergent composition of claim 1 further comprising one or more additional enzymes selected from the group of protease, lipase, cutinase, amylase, carbohydrase, cellulase, pectinase, mannanase, arabinase, galactanase, xylanase, oxidase, xanthanase, laccase, peroxidase, and combinations thereof.

13. The detergent composition of claim 1, wherein the composition is a laundry detergent composition or a dishwashing composition.

14. The detergent composition of claim 1, wherein the detergent composition is utilized in a cleaning process.

15. The detergent composition of claim 14, wherein the cleaning process is laundry.

16. The detergent composition of claim 15, wherein the cleaning process is hard surface cleaning.

17. The detergent composition of claim 1, wherein the detergent composition is utilized for degrading xanthan gum.

18. The detergent composition of claim 17, wherein the detergent composition has an enzyme detergency benefit.

* * * * *